(12) United States Patent
Yoon et al.

(10) Patent No.: US 6,306,860 B1
(45) Date of Patent: Oct. 23, 2001

(54) 2,5-PYRIDINEDICARBOXYLIC ACID DERIVATIVES

(75) Inventors: Sung Joon Yoon, Seoul; Sang Wook Lee, Kyungki-do; Hyeong Su Sim, Seoul; Yong Kyun Park, Kyungki-do; Wang Yong Yang, Kyungki-do; Jong Woo Kim, Kyungki-do; Jae Jin Han, Kyungki-do; Je In Yoon, Kyungki-do; Sang Jin Park, Seoul; Hee Jeoung Park; Dong Hyuk Sin, both of Kyungki-do; Hwan Bong Chang, Ichon, all of (KR)

(73) Assignee: Dong Wha Pharm. Inc. Co., Ltd., Seoul (KR)

( * ) Notice: Subject to any disclaimer, the term of this patent is extended or adjusted under 35 U.S.C. 154(b) by 0 days.

(21) Appl. No.: 09/674,844

(22) PCT Filed: May 1, 1999

(86) PCT No.: PCT/KR99/00213

§ 371 Date: Nov. 7, 2000

§ 102(e) Date: Nov. 7, 2000

(87) PCT Pub. No.: WO99/58526

PCT Pub. Date: Nov. 18, 1999

(30) Foreign Application Priority Data

| May 13, 1998 | (KR) | 98-17153 |
| May 28, 1998 | (KR) | 98-19555 |
| Jul. 14, 1998 | (KR) | 98-28258 |

(51) Int. Cl.$^7$ ............... C07D 401/14; C07D 401/06; C07D 405/14; C07D 409/14; A61K 31/497
(52) U.S. Cl. ............... 514/253.13; 544/364; 544/365; 544/121; 514/235.8
(58) Field of Search ............... 544/364, 365, 544/121; 514/253.13, 235.8

(56) References Cited

U.S. PATENT DOCUMENTS 5,364,873 * 11/1994 Bickel et al. ............ 514/354

FOREIGN PATENT DOCUMENTS

| 24 27 503 | 1/1976 | (DE) . |
| 37 03 963 | 8/1988 | (DE) . |
| 0 563 732 | 10/1993 | (EP) . |
| 0 563 734 | 10/1993 | (EP) . |
| 1994-0001886 | 2/1994 | (KR) . |
| 1996-072384 | 12/1996 | (KR) . |
| 1997-036589 | 7/1997 | (KR) . |
| WO 96/06082 | 2/1996 | (WO) . |
| WO 97/26880 | 7/1997 | (WO) . |
| WO 98/03503 | 1/1998 | (WO) . |
| WO 98/54140 | 12/1998 | (WO) . |

* cited by examiner

*Primary Examiner*—Mark L. Berch
*Assistant Examiner*—Kahsay Habte
(74) *Attorney, Agent, or Firm*—McGuireWoods LLP

(57) ABSTRACT

Anti-viral agents of formula (1) have been identified. Their preparation method is described. These 2,5-pyridinedicarboxylic acid derivatives or their pharmaceutically acceptable salts are useful in countering the proliferation of viruses such as hepatitis B virus and human immunodeficiency virus.

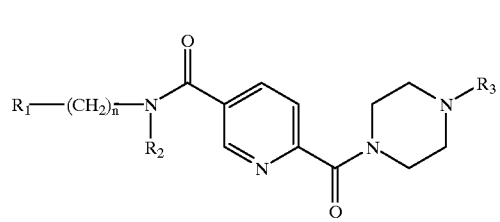

(1)

15 Claims, No Drawings

2,5-PYRIDINEDICARBOXYLIC ACID DERIVATIVES

BACKGROUND OF THE INVENTION

1. Field of the Invention

The present invention relates to novel 2,5-pyridinedicarboxylic acid derivatives and more particularly, to novel 2,5-pyridinedicarboxylic acid derivatives of the following formula 1 and its pharmaceutically acceptable salts as anti-viral agents, having inhibitory activities against the proliferation of virus such as hepatitis B virus and human immunodeficiency virus, including its preparing method:

Formula 1

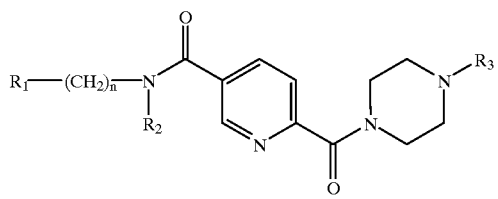

wherein, $R_1$ represents hydroxy group, straight or branched alkyl group of 1 to 6 carbon atoms, cycloalkyl group of 3 to 6 carbon atoms unsubstituted or substituted with alkyl group of 1 to 3 carbon atoms, alkyl group of 1 to 3 carbon atoms substituted with cycloalkyl group of 3 to 6 carbon atoms, straight or branched hydroxyalkyl group of 1 to 6 carbon atoms, straight or branched dihydroxyalkyl group of 3 to 6 carbon atoms, straight or branched alkoxy group of 1 to 4 carbon atoms, hydroxyalkoxy group of 2 to 4 carbon atoms, straight or branched alkoxyalkyl group of 2 to 6 carbon atoms, dialkoxyalkyl group of 3 to 6 carbon atoms, dialkylamino group of 2 to 4 carbon atoms, acetylamino group, vinyl group, or saturated or unsaturated five or six membered heterocyclic ring having 1 to 3 hetero-atoms selected from the group consisting of nitrogen, oxygen and sulfur; hence, the heterocycle is unsubstituted or substituted with same or different 1~3 substituents selected from the group consisting of alkyl group of 1 to 3 carbon atoms, alkoxy group of 1 to 3 carbon atoms, hydroxyalkyl group of 1 to 3 carbon atoms, phenyl group, carbamoyl group and hydroxy group;

$R_2$ represents hydrogen atom, phenyl group, straight or branched alkyl group of 1 to 4 carbon atoms, straight or branched hydroxyalkyl group of 2 to 4 carbon atoms, or alkoxyalkyl group of 2 to 4 carbon atoms;

$R_3$ represents 3-amino-2-pyridyl group

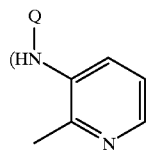

wherein, Q is hydrogen atom or straight or branched alkyl group of 1 to 4 carbon atoms), or 2-hydroxyethyl group;

n is an integer of 0 or 1~4;

meantime, the above $R_1$ that belong to branched hydroxyalkyl group may represent (R)- or (S)-type stereospecificity.

2. Description of the Related Art

About 300 million people around the world are infected with hepatitis caused by Hepatitis B virus (hereinafter referred to as "HBV") as a main pathogen, being accompanied by acute or chronic hepatitis. In severe cases, it is reported that HBV is involved in transforming hepatitis into hepatic cirrhosis hepatocellular carcinoma. In spite of the fact that intensive research have focused on the correlation of liver disease associated with HBV and its molecular biological characteristics, some hepatitis B vaccines and diagnostic reagents have been developed but any effective drug for treating hepatitis B does not exist. Recently, results of some studies have indicated that some nucleoside compounds such as Lamivudine and Famvir, which have been known for AIDS or herpes zoster, are effective in suppressing the proliferation of HBV. However, it has been well known that further development of nucleoside compounds are restricted because of high treatment cost, adverse reaction, and toxicity.

Under such circumstances, there is an urgent need for the development of effective hepatitis B drug as non-nucleoside compound and in parallel with this trend, some patents related to quinolone compound [European Patent Publication Nos. 563732 and 563734] and iridoids compound [Korean Patent Unexamined Publication No. 94-18863] have been reported to have anti-HBV activities but with no significant development progress has been noticeable.

Meantime, the present applicant has filed patent application related to novel terephthalamide derivatives with anti-viral activities as a non-nucleoside compound [Korean Pat. Appln. Nos. 96-72384 and 97-36589].

SUMMARY OF THE INVENTION

The novel 2,5-pyridinedicarboxylic acid derivatives of the present invention have unique chemical structure as non-nucleoside compounds, and show the anti-viral activities against HBV as well as human immunodeficiency virus (hereinafter referred to as "HIV"). Although HBV is different from HIV, they have the same replication processes, which are the reverse transcription from viral RNA and the digestion of RNA part of RNA-DNA hybrid intermediates. Since the novel 2,5-pyridinedicarboxylic acid derivatives according to the present invention of the formula 1 have mechanism to inhibit reverse transcription, it can be developed as anti-HBV or anti-HIV agents.

Therefore, an object of the present invention is to provide novel 2,5-pyridinedicarboxylic acid derivatives and its pharmaceutically acceptable salts which suppress very effectively the proliferation of various viruses such as HBV and HIV, including its preparing method.

DETAILED DESCRIPTION OF THE INVENTION

The present invention is related to novel 2,5-pyridinedicarboxylic acid derivatives of the following formula 1 and its pharmaceutically acceptable salts.

Formula 1

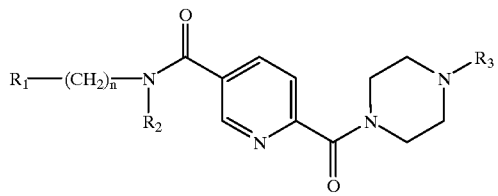

Formula 1a

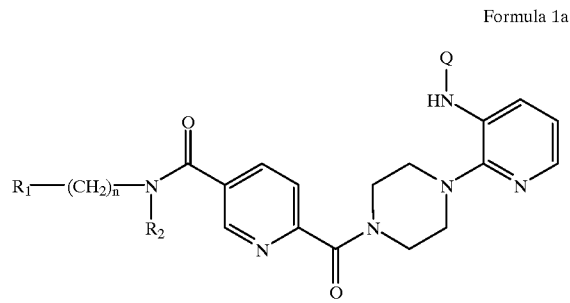

wherein, $R_1$, $R_2$, Q and n are the same as defined above, respectively.

Formula 1b

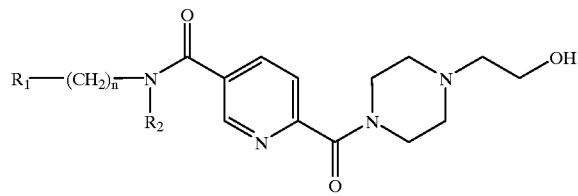

wherein, $R_1$, $R_2$ and n are the same as defined above, respectively.

wherein, $R_1$ represents hydroxy group, straight or branched alkyl group of 1 to 6 carbon atoms, cycloalkyl group of 3 to 6 carbon atoms unsubstituted or substituted with alkyl group of 1 to 3 carbon atoms, alkyl group of 1 to 3 carbon atoms substituted with cycloalkyl group of 3 to 6 carbon atoms, straight or branched hydroxyalkyl group of 1 to 6 carbon atoms, straight or branched dihydroxyalkyl group of 3 to 6 carbon atoms, straight or branched alkoxy group of 1 to 4 carbon atoms, hydroxyalkoxy group of 2 to 4 carbon atoms, straight or branched alkoxyalkyl group of 2 to 6 carbon atoms, dialkoxyalkyl group of 3 to 6 carbon atoms, dialkylamino group of 2 to 4 carbon atoms, acetylamino group, vinyl group, or saturated or unsaturated five or six membered heterocyclic ring having 1 to 3 hetero-atoms selected from the group consisting of nitrogen, oxygen and sulfur; hence, the heterocycle is unsubstituted or substituted with same or different 1~3 substituents selected from the group consisting of alkyl group of 1 to 3 carbon atoms, alkoxy group of 1 to 3 carbon atoms, hydroxyalkyl group of 1 to 3 carbon atoms, phenyl group, carbamoyl group and hydroxy group;

$R_2$ represents hydrogen atom, phenyl group, straight or branched alkyl group of 1 to 4 carbon atoms, straight or branched hydroxyalkyl group of 2 to 4 carbon atoms, or alkoxyalkyl group of 2 to 4 carbon atoms;

$R_3$ represents 3-amino-2-pyridyl group

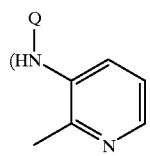

wherein, Q is hydrogen atom or straight or branched alkyl group of 1 to 4 carbon atoms), or 2-hydroxyethyl group;

n is an integer of 0 or 1~4;

meantime, the above $R_1$ that belong to branched hydroxyalkyl group may represent (R)- or (S)-type stereospecificity.

The present invention is explained in more detail as set forth hereunder:

The preferred 2,5-pyridinedicarboxylic acid derivatives of the above formula 1 according to the present invention are represented by the following formula 1a or 1b:

The more preferred compounds according to the present invention are represented by the formula 1a; wherein $R_1$, $R_2$, Q and n are as the follows:

In case where $R_1$ is hydroxy group, branched hydroxyalkyl group of 3 to 5 carbon atoms, or branched dihydroxyalkyl group of 3 to 5 carbon atoms; $R_2$ is hydrogen atom, methyl group, ethyl group, 2-hydroxyethyl group or phenyl group; and n is 0, 2 or 3;

in case where $R_1$ is straight or branched alkyl group of 2 to 4 carbon atoms, cyclopropyl group, cyclopentyl group, methoxy group, ethoxy group, 2-hydroxyethoxy group, branched alkoxyalkyl group of 4 to 5 carbon atoms, dialkoxyalkyl group of 3 to 5 carbon atoms or dialkylamino group of 2 to 4 carbon atoms; $R_2$ is hydrogen atom, methyl group, ethyl group, isopropyl group or 2-methoxyethyl group; n is an integer of 0 or 1~3;

in case where $R_1$ is five or six membered saturated heterocycle selected from the group consisting of dioxolan, tetrahydrofuran, tetrahydrofuranone, tetrahydrothiophenone, pyrrolidinone, morpholine, piperidine and pyrrolidine; $R_2$ is hydrogen atom, methyl group or ethyl group; n is an integer of 0 or 1~3;

in case where $R_1$ is five or six membered heteroaryl group selected from the group consisting of pyrazole, isoxazole, thiazole, thiadiazole, imidazole, furan, thiophene, triazole, pyridine, pyrimidine and pyrazine, and in this case, heteroaryl group is unsubstituted or substituted with same or different 1~3 sustituents which are selected from the group consisting of methyl group, ethyl group, phenyl group, methoxy group, ethoxy group, carbamoyl group, hydroxy group and hydroxymethyl group; $R_2$ is hydrogen atom; n is an integer of 0 or 1~3.

In the above cases, Q represents hydorgen atom, ethyl, isopropyl or isobutyl group.

The more preferred compounds of the formula 1b according to the present invention are as follows:

R$_2$ is hydrogen atom; R$_1$ is straight or branched alkyl group of 2 to 4 carbon atoms or straight or branched alkoxyalkyl group of 2 to 5 carbon atoms; and n is 0.

Futher, 2,5-pyridinedicarboxylic acid derivatives of the above formula 1 according to the present invention may form its pharmaceutically acceptable acid-addition salts with acid in accordance with some ordinary methods in the art to which the present invention pertains. For example, acid-addition salts may include inorganic acids such as hydrochloric acid, hydrobromic acid, phosphoric acid and sulfuric acid, or organic acids such as formic acid, acetic acid, propionic acid, oxalic acid, citric acid, maleic acid, succinic acid, fumaric acid, tartaric acid, trifluoroacetic acid, benzoic acid and methanesulfonic acid.

Meantime, 2,5-pyridinedicarboxylic acid derivatives of the above formula 1 according to the present invention may be used as clinically useful anti-hepatitis B and anti-AIDS agents, since it has potent effects against the proliferation of HBV and HIV.

Therefore, the present invention includes pharmaceutical compositions containing 2,5-pyridinedicarboxylic acid derivatives of the above formula 1 and its pharmaceutically acceptable salts as active ingredients.

When pharmaceutical compositions of the present invention is intended for clinical application, it may be formulated in to dosage forms containing some exipients commonly used in pharmaceutical field. For example, oral preparations (e.g., tablets, capsules, troches, liquids and suspensions); injectables (e.g., injectable solutions or suspension, or injectable powder which can be immediately use by adding water for injection prior to inject). The pharmaceutical preparations may be administered orally or parenterally (e.g., intravenously, subcutaneously, intraperitoneally or topically).

Further the clinical dose of 2,5-pyridinedicarboxylic acid derivatives of the above formula 1 may be appropriately determined range of 10~500 mg, preferably in the range of 50~300 mg. These preparations may be administered at certain intervals of several times (preferably 1–6 times) in accordance with medical or pharmacist's direction.

The present invention also includes a process of preparing 2,5-pyridinedicarboxylic acid derivatives of the formula 1. The representative process of preparing 2,5-pyridinedicarboxylic acid derivatives of the formula 1 is the following reaction scheme 1.

The following reaction scheme 1 is a process for directly preparing 2,5-pyridinedicarboxylic acid derivatives of the formula 1 by reacting nicotinic acid ester derivatives of the following formula 2 and amine compounds of the following formula 3.

Scheme 1

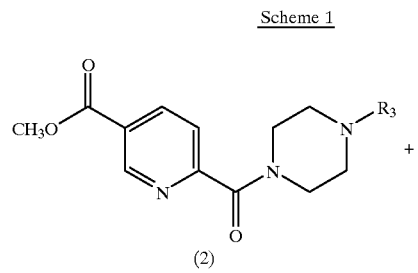

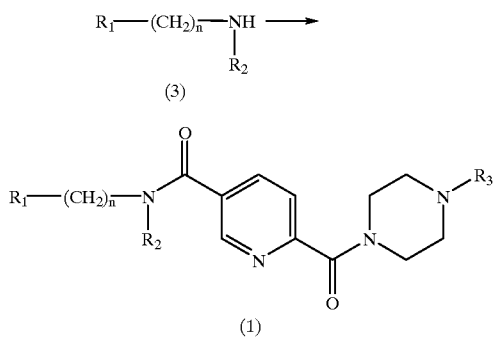

wherein, R$_1$, R$_2$, R$_3$ and n are the same as defined above, respectively.

According to the reaction scheme 1, The reaction is carried out under direct nucleophilic substitution between amine compounds of the formula 3 and methyl ester group of nicotinic acid ester derivatives of the formula 2. The nucleophilic substitution reaction requires more vigorous reaction condition, since the reactivity of the ester group is relatively lower than that of acid anhydride derivative or acid chloride derivative used in the following Scheme 2. The nucleophilic substitution reaction is completed at 40~90° C. within 20 hours in the presence of alcohol solvents (e.g., methanol, ethanol, propanol, isopropanol or butanol) or organic solvents (e.g., acetonitrile, N,N-dimethylformamide, N,N-dimethylacetamide, N-methylpyrrolidone, chloroform, tetrahydrofuran, dioxane or dioxolane).

In particular, 2,5-pyridinedicarboxylic acid derivatives of the formula 1 (wherein, R$_3$ is 3-amino-2-pyridyl group) can be prepared by the following reaction scheme 2 or 3.

The following reaction scheme 2 is a schematic diagram showing a process of preparing 2,5-pyridinedicarboxylic acid derivatives of the formula 1a as desired compounds (wherein, R$_3$ is a 3-amino-2-pyridyl group) by reacting of the formula 2a, reactive intermediate of nicotinic acid derivative and amine compounds of the formula 3:

Scheme 2

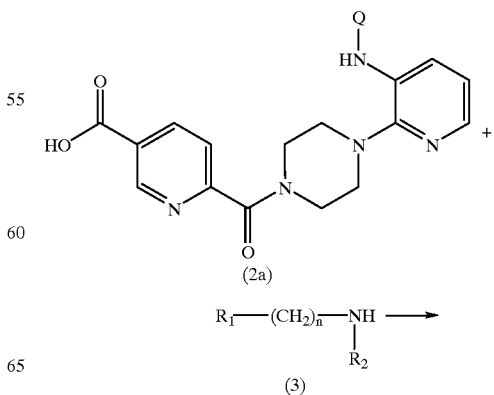

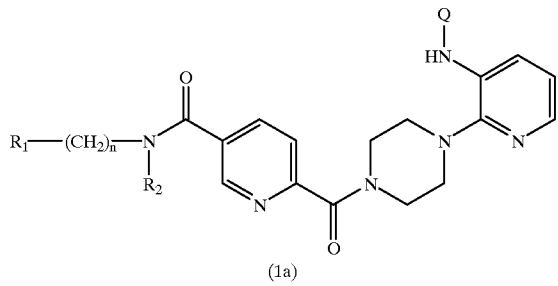

wherein, $R_1$, $R_2$ and Q are the same as defined above, respectively.

The process for preparing 2,5-pyridinedicarboxylic acid derivatives of the present invention according to the scheme 2 is explained in more detail as set forth hereunder.

First, nicotinic acid derivatives of the formula 2a are reacted with acid chloride compound such as pivaloyl chloride to form acid anhydride derivatives with good reactivity, or reacted with thionyl chloride to form acid chloride derivatives with high reactivity; then, the intermediates are reacted with amine compounds of the formula 3 to obtain 2,5-pyridinedicarboxylic acid derivatives of the above formula 1a as desired products.

These reactions may be performed in the presence of general tertiary organic bases (e.g., triethylamine, N,N-diisopropylethylamine, N-methylmorpholine, N-methylpiperidine, 4-dimethylaminopyridine, N,N-dimethylaniline, 2,6-lutidine or pyridine) using 1~1.5 equivalent of amine compounds of the formula 3, or using excess of amine compounds of the formula 3 in the absence of tertiary organic base.

Otherwise, 2,5-pyridinedicarboxylic acid derivatives of the formula 1a as desired products may be also prepared as follows: nicotinic acid derivatives of the Formula 2a are reacted with 1-hydroxybenzotriazole(HOBT) in the presence of 1,3-dicyclohexylcarbodimide(DCC) to form active ester with good reactivity, and are reacted with amine compounds of the formula 3. This reaction is completed at 5° C.~40° C. within 8 hours. In these reactions, it is preferred to use a single solvent or a co-solvent selected from chloroform, methylene chloride, acetonitrile, tetrahydrofuran, dioxane, dioxolane, N,N-dimethylformamide, N,N-dimethylacetamide and N-methylpyrrolidone.

Another process of preparing 2,5-pyridinedicarboxylic acid derivatives (wherein, $R_3$ is a 3-amino-2-pyridyl group) as desired products of the present invention is illustrated in the following reaction scheme 3.

The following reaction scheme 3 relates to a process, wherein nicotinic acid ester derivatives containing a nitro-pyridyl group of the following formula or nicotinic acid derivatives of the following formula 5 are reacted with amine compounds of the following formula 3 to give intermediates of the following formula 6, and then, the intermediates are further reduced.

Scheme 3

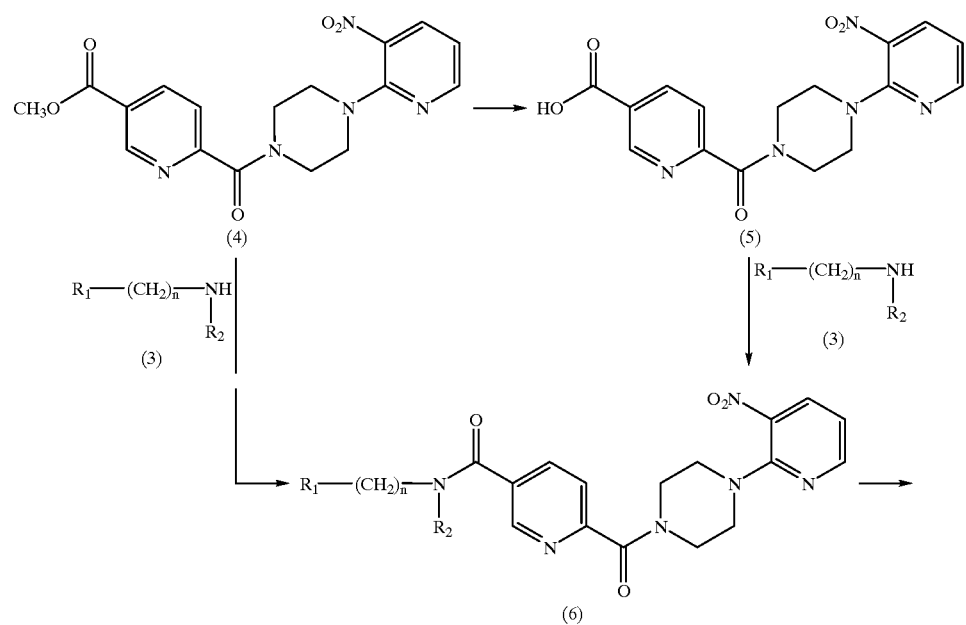

-continued

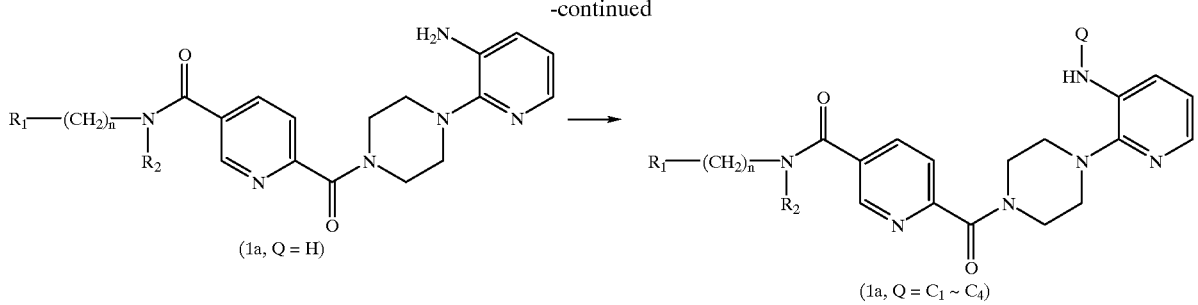

(1a, Q = H)

(1a, Q = C₁ ~ C₄)

wherein $R_1$, $R_2$, Q and n are the same as defined above, respectively.

The process of preparing 2,5-pyridinedicarboxylic acid derivatives of the present invention according to the reaction scheme 3 is explained in more detail as set forth hereunder.

The nicotinic acid derivatives are obtained by hydrolysis of nicotinic acid ester derivatives of the formula 4. In this reaction, a co-solvent containing lower alcohol (e.g., methanol, ethanol or isopropanol) and water is used. The hydrolysis is completed at less than 40° C. within 3 hours in the presence of strong alkali such as sodium hydroxide or potassium hydroxide. The nicotinic acid derivatives of the formula 5, so obtained, are reacted with acid chloride compound such as pivaloyl chloride to form acid anhydride derivatives with good reactivity, or reacted with thionyl chloride to form acid chloride derivatives with high reactivity; then, the intermediates are reacted with amine compounds of the formula 3 to obtain compounds of the formula 6. These reactions are completed at 0° C.~30° C. within 6 hours in the presence of general tertiary organic bases (e.g., triethylamine, N,N-diisopropylethylamine, N-methylmorpholine, N-methylpiperidine, 4-dimethylaminopyridine, N,N-dimethylaniline, 2,6-lutidine or pyridine).

Otherwise, nicotinic acid derivatives of the formula 5 are reacted with 1-hydroxybenzotriazole (HOBT) in the presence of 1,3-dicyclohexylcarbodimide (DCC) to form active ester with good reactivity, and is reacted with amine compounds of the formula 3 to obtain compounds of the formula 6. This reaction is completed at 5° C.~40° C. within 8 hours. In these reactions to prepare compounds of the formula 6, it is preferred to use a single solvent or a co-solvent selected from chloroform, methylene chloride, acetonitrile, tetrahydrofuran, dioxane, dioxolane, N,N-dimethylformamide, N,N-dimethylacetamide and N-methylpyrrolidone.

Further, another process for preparing compounds of the formula 6 is the direct reaction between nicotinic acid ester derivatives of the formula 4, the precursor of the nicotinic acid derivatives of the formula 5 in reaction scheme 3, and amine compounds of the formula 3. This process has an advantage to shorten one step in the manufacturing process. This reaction is carried out under direct nucleophilic substitution between amine compounds of the formula 3 and methyl ester group of nicotinic acid ester derivatives of the formula 4. The nucleophilic substitution reaction requires more stronger reaction condition, since the reactivity of the ester group is relatively lower than that of the activated acid derivatives of the formula 4. The nucleophilic substitution reaction is completed at 40~90° C. within 20 hours in the presence of alcohol solvents (e.g., methanol, ethanol, propanol, isopropanol or butanol) or organic solvents (e.g., acetonitrile, N,N-dimethylformamide, N,N-dimethylacetamide, N-methylpyrrolidone, chloroform, tetrahydrofuran, dioxane or dioxolane).

The compounds of the formula 6 are reduced by catalytic hydrogenation to give compounds of the Formula 1a (Q: hydrogen atom). Such reduction may be well carried out under high-pressure condition using hydrogen gas in the presence of small amounts of activated metal catalysts such as Raney-nickel or palladium on activated carbon, being widely used in the reductive reaction. Various solvents such as methanol, ethanol, methylene chloride, chloroform or ethyl acetate may be used in this reaction.

Further, the compounds (Q: hydrogen atom) of the formula 1a, so obtained, are under reductive alkylation with acetaldehyde, acetone or isobutyraldehyde in the presence of selective reducing agents such as sodium cyanoborohydride under acidic conditions to form desired products of the formula 1a (Q: straight or branched alkyl group of 1 to 4 carbon atoms). This reaction may be carried out in the presence of organic acid such as acetic acid. Usually, lower alcohol solvents such as methanol or ethanol are used.

The amine compounds of the formula 3, used in reaction schemes 1, 2 and 3 are reagents intended for introducing the substituents $R_1$ and $R_2$ into 2,5-pyridinedicarboxylic acid derivatives of the formula 1 as desired products. A person having ordinary skill in the art to which the present invention pertains may easily use some appropriate amine compounds, selected by required substitutes.

Meantime, nicotinic acid derivatives of the formula 2a and nicotinic acid ester derivatives of the formula 2b used as each starting material in the reaction schemes 1 and 2 associated with the process of preparing 2,5-pyridinedicarboxylic acid derivatives of the formula 1, respectively, can be prepared by the following reaction schemes 4 or 5, prior to use.

The following reaction scheme 4 illustrates the process of preparing each compound of the formula 2b and formula 2a, respectively, using 5-(methoxycarbonyl)-2-pyridinecarboxylic acid of the following formula 7 and 1-(3-nitro-2-pyridyl)piperazine of the following formula 8 as starting materials.

Scheme 4

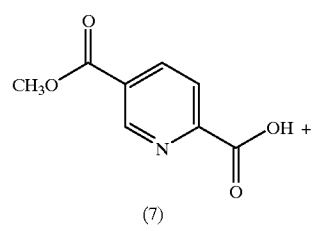

(7)

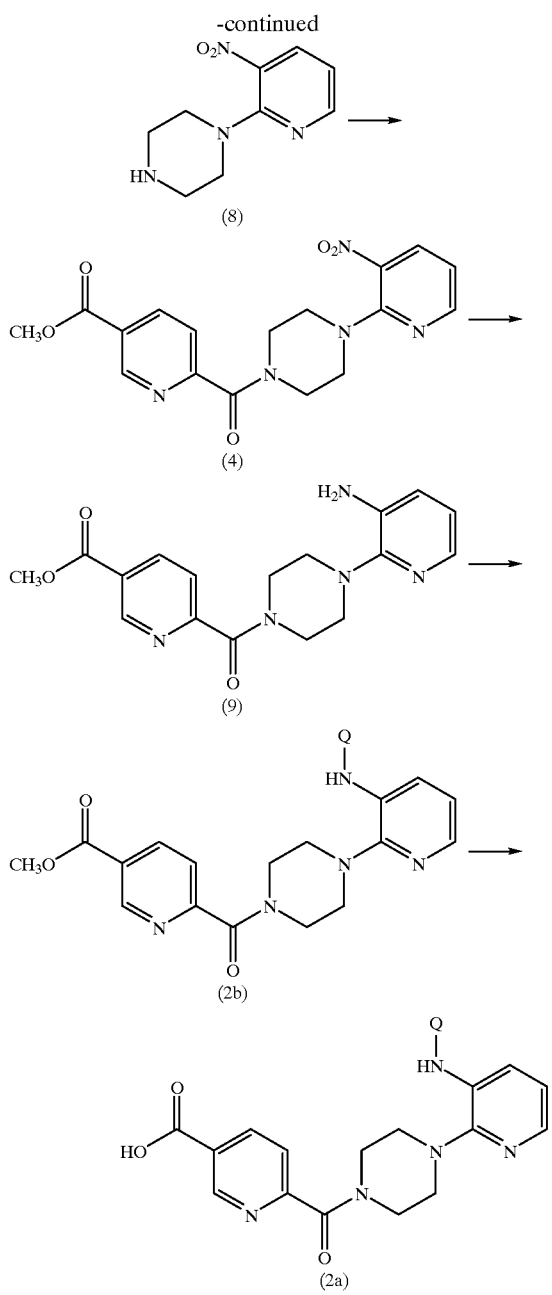

wherein Q is the same as defined above.

5-(Methoxycarbonyl)-2-pyridinecarboxylic acid of the formula 7 as a starting material in reaction scheme 4 may be easily prepared by known process [Nippon Kagaku Kaishi 1967, Vol. 88, 553~556] from 2,5-pyridinedicarboxylic acid (=isocinchomeronic acid) which can be purchased for very cheap price. Also, 1-(3-nitro-2-pyridyl)piperazine of the following formula 8 in reaction scheme 4 may be easily prepared by well known process U. Med. Chem., 1994, Vol. 37, 999~1014] from 2-chloro-3-nitropyridine and piperazine. The process for preparing this starting material is explained in detail in the preparation examples of specifications concerning novel terephthalamide derivatives, which has been disclosed in two patents already filed in Korea by the inventor et al. [Korean Pat. Appln. Nos. 96-72384 and 97-36589].

According to the reaction scheme 4,5-(methoxycarbonyl)-2-pyridinecarboxylic acid of the formula 7 is reacted with acid chloride compound such as pivaloyl chloride to form acid anhydride derivative with good reactivity; then, the intermediate is reacted with 1-(3-nitro-2-pyridyl)piperazine of the formula 8 to obtain nitcotinic acid ester derivative containing a nitropyridyl group of the formula 4. This reaction is completed at 0° C.~30° C. within 6 hours in the presence of general tertiary organic bases (e.g., triethylamine, N,N-diisopropylethylamine, N-methylmorpholine, N-methylpiperidine, 4-dimethylaminopyridine, N,N-dimethylaniline, 2,6-lutidine or pyridine). It is preferred to use a single solvent or a co-solvent selected from chloroform, methylene chloride, acetonitrile, tetrahydrofuran, dioxane, dioxolane, N,N-dimethylformamide, N,N-dimethylacetamide and N-methylpyrrolidone, etc..

The compound of the formula 4 so obtained, is reduced to form derivative containing aminopyridyl group of the formula 9.

Such reduction is well carried out under high-pressure condition using hydrogen gas in the presence of small amounts of activated metal catalysts such as Raney-nickel or palladium on activated carbon, being widely used in the reductive reaction. Various solvents such as methanol, ethanol, methylene chloride, chloroform or ethyl acetate may be used in this reaction.

Further, derivative containing aminopyridyl group of the formula 9, so obtained, is under reductive alkylation with acetaldehyde, acetone or isobutyraldehyde in the presence of selective reducing agents such as sodium cyanoborohydride under acidic condition to form nicotinic acid ester derivatives containing alkylaminopyridyl group of the formula 2b. Such reaction may be carried out well in the presence of some organic acid such as acetic acid. Usually, lower alcoholic solvents such as methanol or ethanol are used.

The nicotinic acid derivatives of 2a are obtained by hydrolysis of nicotinic acid ester derivatives of the formula 2b. In this reaction, a co-solvent containing lower alcohol (e.g., methanol, ethanol or isopropanol) and water is used. The hydrolysis is completed at below 40° C. within 3 hours.

The following reaction scheme 5 illustrates the process of preparing each compound of the formula 2b and formula 2a, respectively, using 5-(methoxycarbonyl)-2-pyridinecarboxylic acid of the following formula 7 and 1-[3-(alkylamino)-2-pyridyl]piperazine of the following formula 10 as starting materials.

Scheme 5

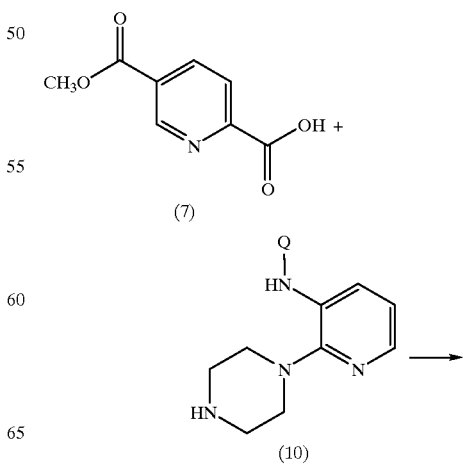

13
-continued

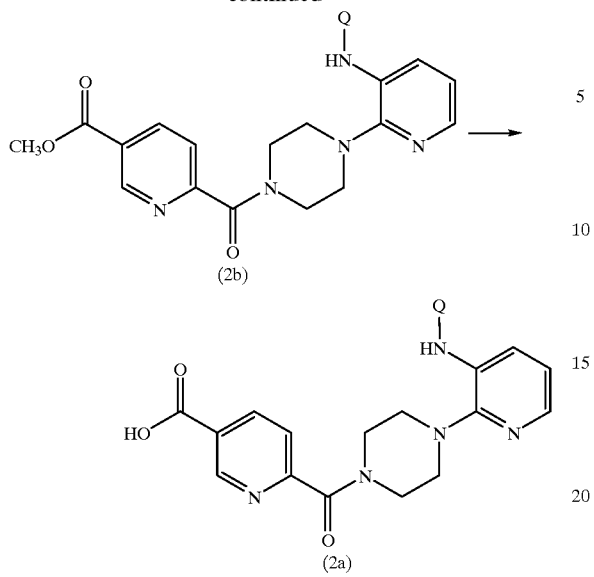

wherein, Q is the same as defined above.

The compound of the formula 7 as a starting material in reaction scheme 5 may be prepared in accordance with Scheme 4. Also, 1-[3-(alkylamino)-2-pyridyl]piperazine of the formula 10 as another starting material in reaction scheme 5 may be prepared by known 4-step processes U. Med. Chem., 1994, Vol. 37, 999~1014] from 1-(3-nitro-2-pyridyl)piperazine of the formula 8, as described in reaction scheme 4. The process for preparing these starting materials are explained in detail in the preparation examples of specifications concerning novel terephthalamide derivatives, which has been disclosed in the patent disclosure already filed in Korea by the inventor et al. [Korean Pat. Appln. No. 96-72384].

According to the reaction scheme 5, 5-(methoxycarbonyl)-2-pyridinecarboxylic acid of the formula 7 is reacted with some acid chloride compound such as pivaloyl chloride to form acid anhydride derivative with good reactivity; then, the intermediate is reacted with 1-[3-(alkylamino)-2-pyridyl]piperazine of the formula 10 to obtain a compound of the formula 2b. This reactions is completed at 0° C.~30° C. within 6 hours in the presence of general tertiary organic bases (e.g., triethylamine, N,N-diisopropylethylamine, N-methylmorpholine, N-methylpiperidine, 4-dimethylaminopyridine, N,N-dimethylaniline, 2,6-lutidine or pyridine). In this reaction, it is preferred to use a single solvent or a co-solvent selected from chloroform, methylene chloride, acetonitrile, tetrahydrofuran, dioxane, dioxolane, N,N-dimethylformamide, N,N-dimethylacetamide and N-methylpyrrolidone.

The nicotinic acid ester derivatives of the formula 2b, so obtained, is hydrolyzed in accordance with reaction scheme 4 to obtain nicotinic acid derivatives of the formula 2a .

Meantime, the nicotinic acid ester derivative of the formula 2c used as a starting material in the reaction scheme 1 can be prepared by the following The following reaction scheme 6 illustrates the process for preparing 6-[1-(2-hydroxyethyl)piperazin-4-yl-carbonyl]nicotinic acid methyl ester of the formula 2c by the reaction between 5-(methoxycarbonyl)-2-pyridinecarboxylic acid of the following formula 7 and 1-(2-hydroxyethyl)piperazine of the following formula 11.

14
Scheme 6

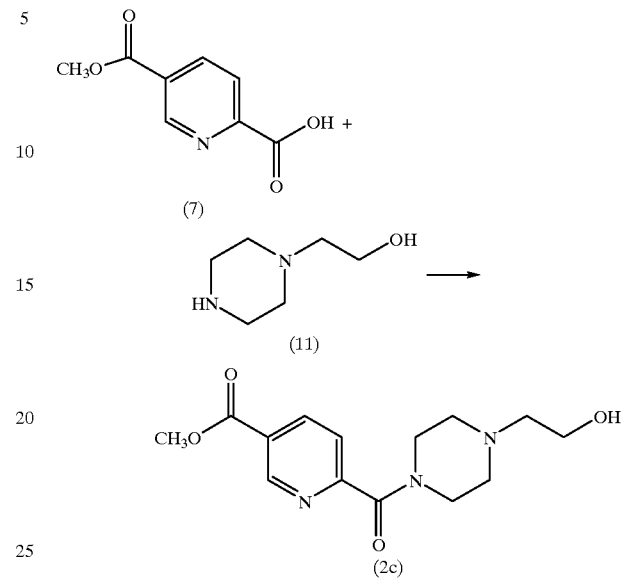

The compound of the formula 7 as a starting material in the reaction scheme 6 may be prepared in accordance with reaction scheme 4. Also, 1-(2-hydroxyethyl)piperazine of the formula 11 as another starting material in reaction scheme 6 may be easily purchased as commercial reagent.

The process described in reaction scheme 6 is explained in more detail as set forth hereunder.

5-(Methoxycarbonyl)-2-pyridinecarboxylic acid of the formula 7 is reacted with acid chloride compound such as pivaloyl chloride to form acid anhydride derivative with good reactivity; then, is reacted with 1-(2-hydroxyethyl) piperazine of the formula 11 to obtain 6-[1-(2-hydroxyethyl) piperazin-4-yl-carbonyl]nicotinic acid methyl ester of the formula 2c. This reaction is completed at 0° C.~30° C. within 6 hours in the presence of general tertiary organic bases (e.g., triethylamine, N,N-diisopropylethylamine, N-methylmorpholine, N-methylpiperidine, 4-dimethylaminopyridine, N,N-dimethylaniline, 2,6-lutidine or pyridine).

Otherwise, 5-(methoxycarbonyl)-2-pyridinecarboxylic acid of the formula 7 is reacted with 1-hydroxybenzotriazole (HOBT) in the presence of 1,3-dicyclohexylcarbodimide (DCC) to form active ester with good reactivity; then, is reacted with 1-(2-hydroxyethyl)piperazine of the formula 11 to obtain 6-[1-(2-hydroxyethyl)piperazin-4-yl-carbonyl] nicotinic acid methyl ester of the formula 2c. This reaction is completed at 5° C.~40° C. within 8 hours. It is preferred to use a single solvent or co-solvents selected from chloroform, methylene chloride, acetonitrile, tetrahydrofuran, dioxane, dioxolane, N,N-dimethylformamide, N,N-dimethylacetamide and N-methylpyrrolidone, etc..

As described above, this invention is explained based on the following examples including preparation examples in more detail but is not limited by these examples.

PREPARATION EXAMPLE 1

Preparation of 6-[1-(3-nitro-2-pyridyl)piperazin-4-yl-carbonyl]nicotinic acid methyl ester 5-(Methoxycarbonyl)-2-pyridinecarboxylic acid (20 g) was added in methylene chloride (200 ml), and then, dissolved with the addition of triethylamine (17 ml). The mixture was cooled, pivaloyl chloride (14.5 ml) was added at 0° C.~5° C. and stirred at 5° C. for 2 hours. 1-(3-Nitro-2-pyridyl)piperazine (23 g) and triethylamine (18 ml) were added to the solution in order and the mixture was reacted at 5° C.~10° C. for 2 hours. The reaction mixture was washed with aqueous sodium bicarbonate and water each twice and then, the separated organic layer was concentrated under reduced pressure. The concentrated residue was treated with ethanol for crystallization and water was added, then the precipitate was filtered. The crude product was recrystallized with ethanol and ether, filtered and dried to give a desired compound of 35.3 g (yield: 86%).

m.p.: 129~130° C.

$^1$H-NMR(CDCl$_3$), ppm: δ3.47(m, 2H), 3.61(m, 2H), 3.75 (m, 2H), 3.96(m, 5H), 6.83(m, 1H), 7.78(m, 1H), 8.18(m, 1H), 8.35(m, 1H), 8.41(m, 1H), 9.16(m, 1H)

PREPARATION EXAMPLE 2

Preparation of 6-[1-(3-amino-2-pyridyl)piperazin-4-yl-carbonyl]nicotinic acid methyl ester 6-[1-(3-Nitro-2-pyridyl)piperazin-4-yl-carbonyl]nicotinic acid methyl ester (6 g) obtained from preparation example 1 was dissolved in methanol (120ml) about 1 ml of Raney-nickel (50% slurry in water) was added and the mixture was filled with hydrogen gas and reduced at 50~60 psi for 4 hours. After completion of the reaction, reaction mixture was filtered through celite and concentrated under reduced pressure. Isopropanol (40 ml) was added to the concentrated residue, stirred, filtered, washed and dried to give a desired compound of 4.97 g (yield: 90%).

m.p.: 175~177° C.

$^1$H-NMR(CDCl$_3$), ppm: δ3.12(m, 2H), 3.21(m, 2H), 3.67 (m, 2H), 3.81(m, 2H), 3.96(m, 5H), 6.84(m, 1H), 6.94(m, 1H), 7.76(m, 2H), 8.37(m, 1H), 9.16(m, 1H)

PREPARATION EXAMPLE 3

Preparation of 6-[1-[3-(isopropylamino)-2-pyridyl]piperazin-4-yl-carbonyl]nicotinic acid methyl ester Method 1

6-[1-(3-Amino-2-pyridyl)piperazin-4-yl-carbonyl]nicotinic acid methyl ester (4 g), so obtained from preparation example 2, was added to methanol (80 ml) and with the successive addition of acetone (2 ml), acetic acid (5 ml) and sodium cyanoborohydride (2.5 g) at 10° C. The mixture was stirred at room temperature for 3 hours. Aqueous 3N-sodium hydroxide was added to the mixture for neutralization (pH=~7.5), followed by the slow addition of excess of water for precipitation. After 2-hours stirring, the precipitate was filtered, washed with water and isopropanol, and dried to give a desired compound of 3.73 g (yield: 83%).

Method 2

5-(Methoxycarbonyl)-2-pyridinecarboxylic acid (5 g) was added in methylene chloride (70 ml) and then dissolved with the addition of triethylamine (4.3ml). The mixture was cooled, pivaloyl chloride (3.6 ml) was added at 0° C.~5° C., and the mixture was stirred at 5° C. for 2 hours. Then, 1-[3-(isopropylamino)-2-pyridyl]piperazine (5.8 g) and triethylamine (4.5 ml) were added to the solution, and the mixture was stirred at 5° C.~10° C. for 2 hours. The reaction solution was washed with aqueous sodium bicarbonate and water twice and then, separated organic layer was concentrated under reduced pressure. The concentrated residue was treated with ether for crystallization, stirred and filtered. The residue was recrystallized with isopropanol, filtered and dried to give a desired compound of 7.87 g (yield: 78%).

m.p.: 93~94° C.

$^1$H-NMR(CDCl$_3$), ppm: δ1.21(d, 6H), 3.09(m, 2H), 3.16 (m, 2H), 3.52(m, 1H), 3.69(m, 2H), 3.95(m, 5H), 4.13(m, 1H), 6.82(m, 1H), 6.92(m, 1H), 7.71(m, 2H), 8.39(m, 1H), 9.17(m, 1H)

PREPARATION EXAMPLE 4

Preparation of 6-[1-[3-(ethylamino)-2-pyridyl]piperazin-4-yl-carbonyl]nicotinic acid methyl ester 6-[1-(3-amino-2-pyridyl)piperazin-4-yl-carbonyl]nicotinic acid methyl ester (5 g) was added to methanol (100 ml) and with the addition of acetic acid (4 ml) and acetaldehyde (1.2 ml) at 5° C.~10° C., the mixture was stirred for 30 minutes. With the addition of sodium cyanoborohyride (1 g), the mixture was stirred at 15° C. for 2 hours. Sodium cyanoborohydride (1 g) was added again, and the mixture was further stirred for 1 hour. Water (50 ml) and 3N-sodium hydroxide solution were added to the mixture for neutralization (pH 7.5) and then, methanol was concentrated under reduced pressure. After the mixture was extracted with chloroform, the separated organic layer was concentrated under reduced pressure. The residue was treated with ether for crystallization and recrystallized with ethyl acetate and hexane. The product was filtered and dried to give a desired compound of 4.1 g (yield: 76%).

m.p.: 80~81° C.

$^1$H-NMR(CDCl$_3$), ppm: δ1.29(t, 3H), 3.13(m, 4H), 3.20 (m, 2H), 3.70(m, 2H), 3.96(m, 5H), 4.17(m, 1H), 6.87(m, 1H), 6.95(m, 1H), 7.72(m, 2H), 8.38(m, 1H), 9.17(m, 1H)

PREPARATION EXAMPLE 5

Preparation of 6-[1-[3-(isobutylamino)-2-pyridyl]piperazin-4-yl-carbonyl]nicotinic acid methyl ester By the same procedure as described in the preparation example 4, synthesis was carried out starting with 6-[1-(3-amino-2-pyridyl)piperazin-4-yl-carbonyl]nicotinic acid methyl ester and using isobutyrlaldehyde. Then, the product was recrystallized with ethanol and hexane to give a desired compound.

Yield: 71% m.p.: 82~84° C.

$^1$H-NMR(CDCl$_3$), ppm: δ1.01(d, 6H), 1.90(m, 1H), 2.87 (m, 2H), 3.07(m, 2H), 3.16(m, 2H), 3.68(m, 2H), 3.91(m, 5H), 4.32(s, 1H), 6.79(m, 1H), 6.90(m, 1H), 7.66(m, 1H), 7.71(m, 1H), 8.38(m, 1H), 9.17(s, 1H)

PREPARATION EXAMPLE 6

Preparation of 6-[1-[3-(isopropylamino)-2-pyridyl]piperazin-4-yl-carbonyl]nicotinic acid 6-[1-[3-(Isopropylamino)-2-pyridyl]piperazin-4-yl-carbonyl]nicotinic acid methyl ester (3 g) was dissolved in methanol (30 ml) and with the addition of aqueous 1N sodium hydroxide (16 ml), the mixture was hydrolyzed at 25°C. for 2 hours. 2N hydrochloric acid was slowly added to the mixture for neutralization (pH=~5), followed by the slow addition of excess of water to precipitate. After 2-hours stirring, the precipitate was filtered, washed with water and dried to give a desired compound of 2.63 g (yield: 91%).

m.p.: 211~214° C.

$^1$H-NMR(CDCl$_3$), ppm: δ1.23(d, 6H), 3.16(m, 2H), 3.36 (m, 2H), 3.57(m, 1H), 3.70(m, 2H), 3.96(m, 2H), 6.96(m, 1H), 7.07(m, 1H), 7.79(m, 1H), 8.00(m, 1H), 8.50(m, 1H), 9.31(m, 1H)

PREPARATION EXAMPLE 7

Preparation of 6-[1-[3-(ethylamino)-2-pyridyl]piperazin-4-yl-carbonyl]nicotinic acid 6-[1-[3-(Ethylamino)-2-pyridyl]piperazin-4-yl-carbonyl] nicotinic acid methyl ester (3 g) was dissolved in methanol (18 ml) and with the addition of aqueous 1N-sodium hydroxide (18 ml), the mixture was hydrolyzed at 30° C. for 2 hours. 3N-hydrochloric acid was slowly added to the mixture for neutralization (pH=5~6), followed by the addition of isopropanol (25 ml) and the slow addition of excess of water to precipitate. After 2-hours stirring at 20° C., the precipitate was filtered, washed with water and dried to give a desired compound of 2.48 g (yield: 86%).

m.p.: 155~157° C.

$^1$H-NMR(DMSO-d$_6$), ppm: δ1.17(t, 3H), 2.84(m, 2H), 2.98(m, 4H), 3.52(m, 2H), 3.86(m, 2H), 6.94(m, 2H), 7.54 (m, 1H), 7.71(m, 1H), 8.38(m, 1H), 9.06(m, 1H), 13.58(s, 1H)

PREPARATION EXAMPLE 8

Preparation of 6-[1-[3-(isobutylamino)-2-pyridyl]piperazin-4-yl-carbonyl]nicotinic acid By the same procedure as described in the preparation example 7, synthesis was carried out starting with 6-[1-[3-(isobutylamino)-2-pyridyl]piperazin-4-yl-carbonyl] nicotinic acid methyl ester.

Yield: 92% m.p.: 160~163° C.

$^1$H-NMR(CDCl$_3$), ppm: δ1.01(d, 6H), 1.92(m, 1H), 2.92 (m, 2H), 3.18(m, 2H), 3.33(m, 2H), 3.70(m, 2H), 3.96(m, 2H), 6.92(m, 1H), 7.03(m, 1H), 7.75(m, 1H), 7.98(m, 1H), 8.49(m, 1H), 9.31(s, 1H)

PREPARATION EXAMPLE 9

Preparation of 6-[1-(3-amino-2-pyridyl)piperazin-4-yl-carbonyl]nicotinic acid

6-[1-(3-Amino-2-pyridyl)piperazin-4-yl-carbonyl] nicotinic acid methyl ester (3 g) was dissolved in methanol (25 ml) and with the addition of aqueous 1N-sodium hydroxide (20 ml), the mixture was stirred at 25° C. for 2 hours. With the slow addition of 3N-hydrochloric acid for neuturalization (pH=~5), water (25 ml) was slowly added to the mixture for precipitate. After a 1-hour stirring, the precipitate was filtered, washed with water and dried to give a desired compound of 2.53 g (yield: 88%).

m.p.: 137~140° C.

$^1$H-NMR(TFA-d$_1$), ppm: δ3.68(m, 4H), 4.08(m, 2H), 4.31(m, 2H), 7.45(m, 1H), 7.81(m, 2H), 8.54(m, 1H), 9.41 (m, 1H), 9.67(m, 1H)

PREPARATION EXAMPLE 10

Preparation of 6-[1-(3-nitro-2-pyridyl)piperazin-4-yl-carbonyl]nicotinic acid

6-[1-(3-Nitro-2-pyridyl)piperazin-4-yl-carbonyl]nicotinic acid methyl ester (10 g) was dissolved in methanol (75 ml) and with the addition of aqueous 1N-sodium hydroxide (75 ml), the mixture was stirred at 30° C for 2 hours. With the slow addition of 3N-hydrochloric acid for neutralization (pH=~5), water (110 ml) was slowly added to the mixture for precipitate. After 2-hours stirring, the precipitate was filtered, washed with water and dried to give a desired compound of 8.66 g (yield: 90%).

m.p.: 185~187° C.

$^1$H-NMR(DMSO-d$_6$), ppm: δ3.37(m, 2H), 3.52(m, 4H), 3.78(m, 2H), 6.94(m, 1H), 7.75(m, 1H), 8.28(m, 1H), 8.39 (m, 2H), 9.06(m, 1H), 13.61(s, 1H)

PREPARATION EXAMPLE 11

Preparation of 6-[1-(2-hydroxyethyl)piperazin-4-yl-carbonyl]nicotinic acid methyl ester Method 1

5-(Methoxycarbonyl)-2-pyridinecarboxylic acid (50 g) was added to methylene chloride (550 ml) and with the addition of triethylamine (42.5 ml), the mixture was dissolved. After being cooled, pivaloyl chloride (36 ml) was added to the mixture at 0° C.~5° C. and stirred at 5° C. for 2 hours. The mixture of 1-(2-hydroxyethyl)piperazine (37 g) and N,N-diisopropylethylamine (48 ml) were added to the mixture at 5° C and the mixture was reacted at 5° C.~10° C. for 2 hours. The solution was washed with aqueous sodium bicarbonate and water twice. The separated organic layer was dried over magnesium sulfate and concentrated under reduced pressure. The concentrated residue was treated with ether for crystallization and recrystallized with ethyl acetate and isopropyl ether to give a desired compound of 57.5 g (yield: 71%).

m.p.: 95~96° C.

$^1$H-NMR(CDCl$_3$), ppm: δ2.65(m, 4H), 2.72(m, 2H), 3.67 (m, 4H), 3.77(m, 2H), 3.96(s, 3H), 7.72(d, 1H), 8.38(m, 1H), 9.16(d, 1H)

Method 2

5-(Methoxycarbonyl)-2-pyridinecarboxylic acid (5 g) was added to a co-solvent of tetrahydrofuran (40 ml) and methylene chloride (60 ml) and with the successive addition of 1,3-dicyclohexylcarbodimide (11.5 g) and 1-hydroxybenzotriazole (4.1 g) at 15° C.~20° C., the mixture was reacted for 2 hours. After being cooled, 1-(2-hydroxyethyl)piperazine (3.8 g) was added to the mixture at 10° C. and stirred at the same temperature for 2 hours. The reaction mixture was heated and further stirred at 20° C.~25° C. for 30 minutes. With the addition of methylene chloride (90 ml), the mixture was washed with water three times, dried over magnesium sulfate and concentrated under reduced pressure. The concentrated residue was treated with ether for crystallization and recrystallized with ethyl acetate and tetrahydrofuran to give a desired compound of 6.3 g (yield: 78%).

m.p.: 95~96° C.

$^1$H-NMR(CDCl$_3$), ppm: δ2.65(m, 4H), 2.72(m, 2H), 3.67 (m, 4H), 3.77(m, 2H), 3.96(s, 3H), 7.72(d, 1H), 8.38(m, 1H), 9.16(d, 1H)

EXAMPLE 1

5-[N-(2-hydroxyethyl)carbamoyl]-2-[1-[3-(isopropylamino)-2-pyridyl]piperazin-4-yl-carbonyl]pyridine Triethylamine (0.54 ml) was added to 6-[1-[3-(isopropylamino)-2-pyridyl]piperazine-4-yl-carbonyl] nicotinic acid (1.3 g) in methylene chloride (40 ml) for dissolution and cooled. With the slow addition of pivaloyl chloride (0.45 ml) at 0° C.~5° C., the reaction mixture was stirred at 5° C. for 2 hours. With the addition of triethylamine (0.6 ml) and ethanolamine (0.25 ml), the mixture was stirred at 5° C.~10° C. for 3 hours. The solution was washed with aqueous sodium bicarbonate and water twice. The separated organic layer was concentrated under reduced pressure. The concentrated residue was treated with ether for crystallization and recrystallized with ethanol and isopropyl ether to give a desired compound of 1.2 g (yield: 83%).

m.p.: 163~165° C.

$^1$H-NMR(CDCl$_3$), ppm: δ1.22(d, 6H), 3.08(m, 2H), 3.18 (m, 2H), 3.63(m, 5H), 3.84(m, 2H), 3.93(m, 2H), 4.13(m, 1H), 6.85(m, 1H), 6.96(m, 1H), 7.48–7.65 (m, 3H), 8.10(m, 1H), 8.89(m, 1H)

EXAMPLE 2

5-[N-(3-Hydroxypropyl)carbamoyl]-2-[1-[3-(isopropylamino)-2-pyridyl]piperazine-4-yl-carbonyl]pyridine 6-[1-[3-(Isopropylamino)-2-pyridyl]piperazine-4-yl-carbonyl]nicotinic acid methyl ester (2.5 g) was dissolved in methanol (40 ml) and with the addition of 3-amino-1-propanol (0.95 g), the mixture was heated to reflux for 12 hours and cooled. The excess of water was added slowly at 25° C. for precipitation, the mixture was stirred for 2 hours and filtered. The filtered solid was recrystallized with isopropanol and ether, filtered and dried to give a desired compound of 2.17 g (yield: 78%).

m.p.: 139~140° C.

$^1$H-NMR(CDCl$_3$), ppm: δ1.23(d, 6H), 1.84(m, 2H), 3.08 (m, 2H), 3.16(m, 2H), 3.52(m, 1H), 3.62(m, 4H), 3.75(m, 2H), 3.94(m, 2H), 4.13(m, 1H), 6.84(m, 1H), 6.94(m, 1H), 7.50(m, 1H), 7.65(m, 2H), 8.13(m, 1H), 8.91(m, 1H)

EXAMPLE 3

5-[N-[(1R)-2-hydroxy-1-methylethyl]carbamoyl]-2-[1-[3-(isopropylamino)-2-pyridyl]piperazin-4-yl-carbonyl]pyridine By the same procedure as described in the example 1, synthesis was carried out starting with 6-[1-[3-(isopropylamino)-2-pyridyl]piperazine-4-yl-carbonyl] nicotinic acid and using (R)-(−)-2-amino-1-propanol. Then, the product was recrystallized with ethanol and hexane to give a desired compound.

Yield: 80% m.p.: 129~130° C.

$^1$H-NMR(CDCl$_3$), ppm: δ1.22(d, 6H), 1.28(d, 3H), 3.05 (m, 2H), 3.21(m, 2H), 3.63(m, 4H), 3.85(m, 2H), 4.01(m, 1H), 4.11(m, 1H), 4.25(m, 1H), 6.83(m, 1H), 6.94(m, 1H), 7.28(m, 1H), 7.41(m, 1H), 7.65(m, 1H), 8.03(m, 1H), 8.85 (m, 1H)

EXAMPLE 4

5-[N-[(1S)-2-hydroxy-1-methylethyl]carbamoyl]-2-[1-[3-(isopropylamino)-2-pyridyl]piperazin-4-yl-carbonyl]pyridine By the same procedure as described in the example 3, synthesis was carried out using (S)-(+)-2-amino-1-propanol.

Yield: 76% m.p.: 129~130° C.

$^1$H-NMR(CDCl$_3$), ppm: δ1.22(d, 6H), 1.30(d, 3H), 3.04 (m, 2H), 3.20(m, 2H), 3.60(m, 4H), 3.83(m, 2H), 4.01(m, 1H), 4.11(m, 1H), 4.25(m, 1H), 6.82(m, 1H), 6.94(m, 1H), 7.31(m, 1H), 7.39(m, 1H), 7.64(m, 1H), 8.04(m, 1H), 8.84 (m, 1H)

EXAMPLE 5

5-[N-(2-hydroxy-1-methylethyl)carbamoyl]-2-[1-[3-(isopropylamino)-2-pyridyl]piperazin-4-yl-carbonyl]pyridine By the same procedure as described in the example 3, synthesis was carried out using 2-amino-1-propanol.

Yield: 82%

$^1$H-NMR(CDCl$_3$), ppm: δ1.22(d, 6H), 1.30(d, 3H), 3.05 (m, 2H), 3.21(m, 2H), 3.62(m, 4H), 3.84(m, 2H), 4.00(m, 1H), 4.11(m, 1H), 4.26(m, 1H), 6.82(m, 1H), 6.95(m, 1H), 7.30(m, 1H), 7.41(m, 1H), 7.95(m, 1H), 8.03(m, 1H), 8.84 (m, 1H)

EXAMPLE 6

5-[N-(1,1-dimethyl-2-hydroxyethyl)carbamoyl]-2-[1-[3-(isopropylamino)-2-pyridyl]piperazin-4-yl-carbonyl]pyridine By the same procedure as described in the example 1, synthesis was carried out starting with 6-[1-[3-(isopropylamino)-2-pyridyl]piperazin-4-yl-carbonyl] nicotinic acid and using 2-amino-2-methyl-1-propanol. Then, the product was recrystallized with ethyl acetate and ether to give a desired compound.

Yield: 74% m.p.: 145~146° C.

$^1$H-NMR(CDCl$_3$), ppm: δ1.21(d, 6H), 1.43(d, 6H), 3.08 (m, 2H), 3.17(m, 2H), 3.54(m, 1H), 3.63(m, 2H), 3.69(m, 2H), 3.94(m, 2H), 4.14(m, 1H), 6.68(m, 1H), 6.86(m, 1H), 6.94(m, 1H), 7.55(m, 1H), 7.67(m, 1H), 8.09(m, 1H), 8.88 (m, 1H)

EXAMPLE 7

5-[N-[(1R)-1-ethyl-2-hydroxyethyl]carbamoyl]-2-[1-[3-(isopropylamino)-2-pyridyl]piperazin-4-yl-carbonyl]pyridine By the same procedure as described in the example 1, synthesis was carried out starting with 6-[1-[3-(isopropylamino)-2-pyridyl]piperazin-4-yl-carbonyl] nicotinic acid and using (R)-(−)-2-amino-1-butanol. Then, the product was recrystallized with ethanol and petroleum ether to give a desired compound.

Yield: 83% m.p.: 85~88° C.

$^1$H-NMR(CDCl$_3$), ppm: δ0.99(t, 3H), 1.22(d, 6H), 1.68 (m, 2H), 3.06(m, 2H), 3.17(m, 2H), 3.52(m, 3H), 3.68(m, 1H), 3.82(m, 2H), 4.01(m, 3H), 6.85(m, 1H), 6.96(m, 1H), 7.30(m, 1H), 7.38(m, 1H), 7.65(m, 1H), 8.03(m, 1H), 8.85 (m, 1H)

EXAMPLE 8

5-[N-[(1S)-1-ethyl-2-hydroxyethyl]carbamoyl]-2-11-[3-(isopropylamino)-2-pyridyl]piperazin-4-yl-carbonyl]pyridine By the same procedure as described in the example 7, synthesis was carried out using (S)-(+)-2-amino-1-butanol.

Yield: 81%

$^1$H-NMR(CDCl$_3$), ppm: δ0.99(t, 3H), 1.21(d, 6H), 1.67 (m, 2H), 3.06(m, 2H), 3.17(m, 2H), 3.52(m, 3H), 3.67(m, 1H), 3.81(m, 2H), 4.01(m, 3H), 6.84(m, 1H), 6.96(m, 1H), 7.30(m, 1H), 7.37(m, 1H), 7.65(m, 1H), 8.05(m, 1H), 8.86 (m, 1H)

EXAMPLE 9

5-[N-(1-ethyl-2-hydroxyethyl)carbamoyl]-2-[1-[3-(isopropylamino)- 2-pyridyl]piperazin-4-yl-carbonyl]pyridine By the same procedure as described in the example 7, synthesis was carried out using 2-amino-1-butanol.

Yield: 77%

¹H-NMR(CDCl₃), ppm: δ0.98(t, 3H), 1.22(d, 6H), 1.67 (m, 2H), 3.06(m, 2H), 3.16(m, 2H), 3.53(m, 3H), 3.68(m, 1H), 3.82(m, 2H), 4.02(m, 3H), 6.85(m, 1H), 6.97(m, 1H), 7.29(m, 1H), 7.38(m, 1H), 7.65(m, 1H), 8.03(m, 1H), 8.85 (m, 1H)

EXAMPLE 10

5-[N-[(1R)-2-hydroxy-1-isopropylethyl]carbamoyl]-2-[1-[3-(isopropylamino)-2-pyridyl]piperazin-4-yl-carbonyl]pyridine By the same procedure as described in the example 1, synthesis was carried out starting with 6-[1-[3-(isopropylamino)-2-pyridyl]piperazin-4-yl-carbonyl] nicotinic acid and using (R)-(−)-2-amino-3-methyl-1-butanol. Then, the product was recrystallized with acetone and hexane to give a desired compound.

Yield: 73%

¹H-NMR(CDCl₃), ppm: δ1.01(d, 6H), 1.22(d, 6H), 2.00 (m, 1H), 3.10(m, 4H), 3.50(m, 4H), 3.83(m, 2H), 4.00(m, 3H), 6.82(m, 1H), 6.93(m, 1H), 7.29(m, 1H), 7.40(m, 1H), 7.65(m, 1H), 8.02(m, 1H), 8.85(m, 1H)

EXAMPLE 11

5-[N-[(1S)-2-hydroxy-1-isopropylethyl]carbamoyl]-2-[1-[3-(isopropylamino)-2-pyridyl]piperazin-4-yl-carbonyl]pyridine By the same procedure as described in the example 10, synthesis was carried out using (S)-(+)-2-amino-3-methyl-1-butanol.

Yield: 75%

¹H-NMR(CDCl₃), ppm: δ1.00(d, 6H), 1.23(d, 6H), 2.01 (m, 1H), 3.13(m, 4H), 3.52(m, 4H), 3.83(m, 2H), 4.00(m, 3H), 6.83(m, 1H), 6.94(m, 1H), 7.29(m, 1H), 7.39(m, 1H), 7.66(m, 1H), 8.00(m, 1H), 8.85(m, 1H)

EXAMPLE 12

5-[N-(2-hydroxy-1-isopropylethyl)carbamoyl]-2-[1-[3-(isopropylamino)-2-pyridyl]piperazin-4-yl-carbonyl]pyridine By the same procedure as described in the example 10, synthesis was carried out using 2-amino-3-methyl-1-butanol.

Yield: 80%

¹H-NMR(CDCl₃), ppm: δ1.01(d, 6H), 1.23(d, 6H), 2.01 (m, 1H), 3.12(m, 4H), 3.52(m, 4H), 3.82(m, 2H), 4.01(m, 3H), 6.82(m, 1H), 6.95(m, 1H), 7.28(m, 1H), 7.39(m, 1H), 7.66(m, 1H), 8.01(m, 1H), 8.84(m, 1H)

EXAMPLE 13

5-[N-[Bis(hydroxymethyl)methyl]carbamoyl]-2-[1-[3-(isopropylamino)-2-pyridyl]piperazin-4-yl-carbonyl]pyridine By the same procedure as described in the example 2, synthesis was carried out starting with 6-[1-[3-(isopropylamino)-2-pyridyl]piperazin-4-yl-carbonyl] nicotinic acid methyl ester and using 2-amino-1,3-propandiol. Then, the product was recrystallized with ethyl acetate and hexane to give a desired compound.

Yield: 78% m.p.: 90~93° C.

¹H-NMR(CDCl₃), ppm: δ1.21(d, 6H), 3.07(m, 4H), 3.51 (m, 4H), 3.85(m, 6H), 4.16(m, 2H), 6.85(m, 1H), 6.93(m, 1H), 7.48(m, 1H), 7.62(m, 1H), 7.85(m, 1H), 8.13(m, 1H), 8.92(m, 1H)

EXAMPLE 14

5-[N-ethyl-N-(2-hydroxyethyl)carbamoyl]-2-[1-[3-(isopropylamino)-2-pyridyl]piperazin-4-yl-carbonyl]pyridine By the same procedure as described in the example 1, synthesis was carried out starting with 6-[1-[3-(isopropylamino)-2-pyridyl]piperazin-4-yl-carbonyl] nicotinic acid and using 2-(ethylamino)ethanol. And then, the product was recrystallized with isopropanol and hexane to give a desired compound.

Yield: 74% m.p.: 134~135° C.

¹H-NMR(CDCl₃), ppm: δ1.15(t, 3H), 1.22(d, 6H), 3.14 (m, 4H), 3.33(m, 2H), 3.54(m, 1H), 3.71(m, 4H), 3.92(m, 4H), 4.14(m, 1H), 6.85(m, 1H), 6.93(m, 1H), 7.68(m, 2H), 7.84(m, 1H), 8.64(m, 1H)

EXAMPLE 15

5-[N-(2-hydroxyethyl)-N-methylcarbamoyl]-2-[1-[3-(isopropylamino)-2-pyridyl]piperazin-4-yl-carbonyl]pyridine By the same procedure as described in the example 14, synthesis was carried out using 2-(methylamino)ethanol.

Yield: 82%

¹H-NMR(CDCl₃), ppm: δ1.22(d, 6H), 3.02(s, 3H), 3.12 (m, 4H), 3.54(m, 1H), 15 3.72(m, 4H), 3.93(m, 4H), 4.13(m, 1H), 6.85(m, 1H), 6.93(m, 1H), 7.68(m, 1H), 7.84(m, 1H), 8.64(m, 1H)

EXAMPLE 16

5-[N,N-bis(2-hydroxyethyl)carbamoyl]-2-[1-[3-(isopropylamino)-2-pyridyl]piperazin-4-yl-carbonyl]pyridine By the same procedure as described in the example 1, synthesis was carried out starting with 6-[1-[3-(isopropylamino)-2-pyridyl]piperazin-4-yl-carbonyl] nicotinic acid and using diethanolamine. And then, the product was recrystallized with isopropanol and ether to give a desired compound.

Yield: 77% m.p.: 130~132° C.

¹H-NMR(CDCl₃), ppm: δ1.22(d, 6H), 3.05(m, 2H), 3.13 (m, 2H), 3.55(m, 1H), 3.61(m, 6H), 3.90(m, 2H), 4.05(m, 4H), 4.21(m, 1H), 6.91(m, 1H), 7.02(m, 1H), 7.64(m, 1H), 7.69(m, 1H), 8.20(m, 1H), 8.95(s, 1H)

EXAMPLE 17

5-[N-(2-hydroxyethyl)-N-phenylcarbamoyl]-2-11-[3-(isopropylamino)-2-pyridyl]piperazin-4-yl-carbonyl]pyridine By the same procedure as described in the example 1, synthesis was carried out starting with 6-[1-[3-(isopropylamino)-2-pyridyl]piperazin-4-yl-carbonyl] nicotinic acid and using N-phenylethanolamine. Ane then, the product was recrystallized with isopropylether to give a desired compound.

Yield: 65% m.p.: 127~130° C.

$^1$H-NMR(CDCl$_3$), ppm: δ1.23(d, 6H), 3.06(m, 2H), 3.14 (m, 2H), 3.55(m, 1H), 3.62(m, 2H), 3.88(m, 4H), 4.16(m, 3H), 6.86(m, 1H), 6.95(m, 1H), 7.13(m, 2H), 7.23(m, 1H), 7.30(m, 2H), 7.50(m, 1H), 7.68(m, 1H), 7.74(m, 1H), 8.51(s, 1H)

EXAMPLE 18

2-[1-[3-(ethylamino)-2-pyridyl]piperazin-4-yl-carbonyl]-5-[N-(2-hydroxyethyl)carbamoyl]pyridine By the same procedure as described in the example 2, synthesis was carried out starting with 6-[1-[3-(ethylamino)-2-pyridyl]piperazin-4-yl-carbonyl]nicotinic acid methyl ester and using ethanolamine. And then, the product was recrystallized with ethanol and hexane to give a desired compound.

Yield: 73% m.p.: 178~180° C.

$^1$H-NMR(CDCl$_3$), ppm: δ1.31(t, 3H), 3.13(m, 4H), 3.21 (m, 2H), 3.63(m, 4H), 3.84(m, 2H), 3.96(m, 2H), 4.22(m, 1H), 6.86(m, 1H), 6.96(m, 1H), 7.51(m, 1H), 7.64(m, 1H), 7.69(m, 1H), 8.10(m, 1H), 8.91(s, 1H)

EXAMPLE 19

5-[N-(1,1-dimethyl-2-hydroxyethyl)carbamoyl]-2-[1-[3-(ethylamino)-2-pyridyl]piperazin-4-yl-carbonyl]pyridine By the same procedure as described in the example 1, synthesis was carried out starting with 6-[1-[3-(ethylamino)-2-pyridyl]piperazin-4-yl-carbonyl]nicotinic acid and using 2-amino-2-methyl-1-propanol. And then, the product was recrystallized to give a desired compound.

Yield: 70% m.p.: 128~130° C.

$^1$H-NMR(CDCl$_3$), ppm: δ1.30(t, 3H), 1.46(s, 6H), 3.16 (m, 4H), 3.23(m, 2H), 3.96(m, 4H), 3.97(m, 2H), 6.70(s, 1H), 6.90(m, 1H), 6.99(m, 1H), 7.61(m, 1H), 7.71(m, 1H), 8.12(m, 1H), 8.91(s, 1H)

EXAMPLE 20

2-[1-(3-Amino-2-pyridyl)piperazine4-yl-carbonyl]-5-[N-(2-hydroxyethyl)carbamoyl]pyridine 6-[1-(3-Amino-2-pyridyl)piperazine-4-yl-carbonyl]nicotinic acid (0.5 g) was added to a co-solvent of tetrahydrofuran (10 ml) and methylene chloride (10 ml) and with the successive addition of 1,3-dicyclohexylcarbodimide (0.65 g) and 1-hydroxybenzotriazole (0.23 g) at 15~20° C., the mixture was stirred for 2 hours. With the addition of ethanolamine (0.18 ml), the mixture was stirred again at 20~25° C. for 2 hours. Methylene chloride (30 ml) was added again to the mixture, washed with water 3 times, dried over magnesium sulfate and concentrated under reduced pressure. The concentrated residue was treated with ether for crystallization. The solid was recrystallized with ethanol and hexane to give a desired compound of 0.44 g (yield: 78%).

m.p.: 197~199° C.

$^1$H-NMR(CDCl$_3$+CD$_3$OD), ppm: δ3.16(m, 2H), 3.25(m, 2H), 3.59(m, 2H), 3.68(s, 2H), 3.77(m, 2H), 3.98(m, 2H), 6.94(m, 1H), 7.09(m, 1H), 7.74(m, 2H), 8.30(m, 1H), 9.30(s, 1H)

EXAMPLE 21

2-[1-(3-amino-2-pyridyl)piperazin-4-yl-carbonyl]-5-[N-(1,1-dimethyl-2-hydroxyethyl)carbamoyl]pyridine By the same procedure as described in the example 20, synthesis was carried out using 2-amino-2-methyl-1-propanol.

Yield: 67% m.p.: 120~122° C.

$^1$H-NMR(CDCl$_3$), ppm: δ1.46(s, 6H), 3.16(m, 2H), 3.26 (m, 2H), 3.67(m, 2H), 3.71(s, 2H), 3.97(m, 2H), 6.67(s, 1H), 6.89(m, 1H), 7.01(m, 1H), 7.60(m, 1H), 7.79(m, 1H), 8.11 (m, 1H), 8.90(s, 1H)

EXAMPLE 22

5-[N-(2-hydroxyethyl)carbamoyl]-2-[1-13-(isobutylamino)-2-pyridyl]piperazin-4-yl-carbonyl]pyridine By the same procedure as described in the example 1, synthesis was carried out starting with 6-[1-[3-(isobutylamino)-2-pyridyl]piperazin-4-yl-carbonyl] nicotinic acid to give a desired compound.

Yield: 80% m.p.: 136~139° C.

$^1$H-NMR(CDCl$_3$), ppm: δ0.99(d, 6H), 1.90(m, 1H), 2.88 (m, 2H), 3.06(m, 2H), 3.18(m, 2H), 3.60(m, 4H), 3.82(m, 2H), 3.94(m, 2H), 4.32(m, 1H), 6.78(m, 1H), 6.91(m, 1H), 7.46(m, 1H), 7.55(m, 1H), 7.65(m, 1H), 8.05(m, 1H), 8.86(s, 1H)

EXAMPLE 23

5-[N-(1,1-dimethyl-2-hydroxyethyl)carbamoyl]-2-[1-[3-(isobutylamino)-2-pyridyl]piperazin-4-yl-carbonyl]pyridine By the same procedure as described in the example 6, synthesis was carried out starting with 6-[1-[3-(isobutylamino)-2-pyridyl]piperazin-4-yl-carbonyl] nicotinic acid to give a desired compound.

Yield: 71% m.p.: 140~143° C.

$^1$H-NMR(CDCl$_3$), ppm: δ0.99(d, 6H), 1.43(s, 6H), 1.90 (m, 1H), 2.88(m, 2H), 3.05(m, 2H), 3.17(m, 2H), 3.62(m, 2H), 3.68(s, 2H), 3.94(m, 2H), 4.32(m, 1H), 6.65(s, 1H), 6.79(m, 1H), 6.81(m, 1H), 7.53(m, 1H), 7.65(m, 1H), 8.05 (m, 1H), 8.86(s, 1H)

EXAMPLE 24

2-[1-[3-(isopropylamino)-2-pyridyl]piperazin-4-yl-carbonyl]-5-(N-isopropylcarbamoyl)pyridine Triethylamine (1.6 ml) was added to 6-[1-[3-(isopropylamino)-2-pyridyl]piperazin-4-yl-carbonyl] nicotinic acid (4 g) in methylene chloride (50 ml) for dissolution and cooled. With the slow addition of pivaloyl chloride (1.4 ml) at 0° C.~5° C., the mixture was stirred at 5 C for 1 hour. With the addition of triethylamine (1.7 ml) and isopropylamine (1.2 ml), the mixture was stirred at 10° C. for 2 hours. The solution was washed with aqueous sodium bicarbonate and water twice. The separated organic layer was dried over magnesium sulfate and concentrated under reduced pressure. Isopropanol (40 ml) was added to the concentrated residue, stirred and filtered. The solid was recrystallized with ethyl acetate and ether to give a desired compound of 3.6 g (yield: 81%).

m.p.: 175~176° C.

$^1$H-NMR(CDCl$_3$), ppm: δ1.21(d, 6H), 1.28(d, 6H), 3.07 (m, 2H), 3.15(m, 2H), 3.54(m, 1H), 3.67(m, 2H), 3.94(m, 2H), 4.13(m, 1H), 4.28(m, 1H), 6.33(m, 1H), 6.84(m, 1H), 6.93(m, 1H), 7.65(m, 2H), 8.11(m, 1H), 8.90(m, 1H)

EXAMPLE 25

2-[1-[3-(ethylamino)-2-pyridyl]piperazin-4-yl-carbonyl]-5-(N-isopropylcarbamoyl)pyridine 6-[1-[3-(ethylamino)-2-pyridyl]piperazin-4-yl-carbonyl] nicotinic acid methyl ester (2 g) was dissolved in methanol (25 ml) and with the addition of isopropylamine (5 ml), the mixture was heated to reflux for 12 hours. The mixture was concentrated under reduced pressure to remove the solvent. The residue was treated with ether for crystallization, and the solid was recrystallized with chloroform and hexane to give a desired compound of 1.59 g (yield: 74%).

m.p.: 188~190° C.

$^1$H-NMR(CDCl$_3$), ppm: δ1.29(m, 9H), 3.16(m, 6H), 3.70 (m, 2H), 3.97(m, 2H), 4.20(m, 1H), 4.32(m, 1H), 6.27(m, 1H), 6.87(m, 1H), 6.96(m, 1H), 7.71(m, 2H), 8.14(m, 1H), 8.93(m, 1H)

EXAMPLE 26

2-[1-[3-(isobutylamino)-2-pyridyl]piperazin-4-yl-carbonyl]-5-(N-isopropylcarbamoyl)pyridine By the same procedure as described in the example 24, synthesis was carried out starting with 6-[1-[3-(isobutylamino)-2-pyridyl]piperazin-4-yl-carbonyl] nicotinic acid to give a desired compound.

Yield: 76% m.p.: 132~134° C.

$^1$H-NMR(CDCl$_3$), ppm: δ1.02(d, 6H), 1.30(d, 6H), 1.93 (m, 1H), 2.91(m, 2H), 3.08(m, 2H), 3.19(m, 2H), 3.69(m, 2H), 3.98(m, 2H), 4.31(m, 2H), 6.21(d, 1H), 6.83(m, 1H), 6.93(m, 1H), 7.68(m, 2H), 8.15(m, 1H), 8.93(s, 1H)

EXAMPLE 27

2-[1-(3-amino-2-pyridyl)piperazin-4-yl-carbonyl]-5-(N-isopropylcarbamoyl)pyridine Step (1): Preparation of 5-(N-isopropylcarbamoyl)-2-[1-(3-nitro-2-pyridyl)piperazin-4-yl-carbonyl]pyridine Triethylamine (0.85 ml) was added to 6-[1-(3-nitro-2-pyridyl)piperazin-4-yl-carbonyl]nicotinic acid (2 g) in methylene chloride (25 ml) for dissolution and cooled. With the slow addition of pivaloyl chloride (0.7 ml) at 0° C.~5° C., the mixture was stirred at 5° C.~10° C. for 2 hours. With the addition of N,N-diisopropylethylamine (1.1 ml) and isopropylamine (0.55 ml), the mixture was stirred at 10° C.~15° C. for 3 hours. The reaction mixture was washed with an aqueous sodium bicarbonate and water twice. The separated organic layer was dried over magnesium sulfate and concentrated under reduced pressure. The residue was dissolved in chloroform (15 ml) and with the slow addition of ether, crystals were precipitated. For 2-hours stirring, the precipitate was filtered, washed (ether) and dried to give a desired compound of 1.74 g (yield: 78%).

m.p.: 143~145° C.

$^1$H-NMR(CDCl$_3$), ppm: δ1.28(d, 6H), 3.46(m, 2H), 3.63 (m, 2H), 3.75(m, 2H), 3.97(m, 2H), 4.32(m, 1H), 6.28(m, 1H), 6.85(m, 1H), 7.72(m, 1H), 8.18(m, 1H), 8.37(m, 1H), 8.94(m, 1H)

Step (2): Preparation of 2-[1-(3-amino-2-pyridyl)piperazin-4-yl-carbonyl]-5-(N-isopropylcarbamoyl)pyridine A mixture of 5-(N-isopropylcarbamoyl)-2-[1-(3-nitro-2-pyridyl)piperazin-4-yl-carbonyl]pyridine (1.5 g), so obtained from the Step (1) and about 0.3 ml of Raney-nickel (50% slurry in water) was added to methanol (30 ml) in a pressurized reactor and the reaction mixture was filled with hydrogen gas and reduced at 50~60 psi for 3 hours. After completion of the reduction, reaction mixture was filtered through celite and concentrated under reduced pressure. The concentrated residue was treated with ether for crystalization and recrystallized with ethyl acetate and isopropyl ether to give a desired compound of 1.05 g (yield: 75%).

m.p.: 142~143° C.

$^1$H-NMR(CDCl$_3$), ppm: δ1.29(d, 2H), 3.13(m, 2H), 3.24 (m, 2H), 3.67(m, 2H), 3.98(m, 2H), 4.32(m, 1H), 6.40(m, 1H), 6.86(m, 1H), 6.99(m, 1H), 7.63(m, 1H), 7.80(m, 1H), 8.15(m, 1H), 8.92(m, 1H)

EXAMPLE 28

5-[N-(1,1-dimethylethyl)carbamoyl]-2-[1-[3-(isopropylamino)-2-pyridyl]piperazin-4-yl-carbonyl] pyridine By the same procedure as described example 24, the synthesis was carried out starting with 6-[1-[3-(isopropylamino)-2-pyridyl]piperazin-4-yl-carbonyl] nicotinic acid and using 2-methyl-2-propaneamine. And then, the product was recrystallized with isopropanol to give a desired compound.

Yield: 82% m.p.: 161~162° C.

$^1$H-NMR(CDCl$_3$), ppm: δ1.27(d, 6H), 1.49(s, 9H), 3.11 (m, 2H), 3.20(m, 2H), 3.54(m, 1H), 3.71(m, 2H), 3.97(m, 2H), 4.16(m, 1H), 6.05(m, 1H), 6.87(m, 1H), 6.97(m, 1H), 7.70(m, 2H), 8.14(m, 1H), 8.90(m, 1H)

EXAMPLE 29

5-[N-(1,1-dimethylethyl)carbamoyl]-2-[1-[3-(ethylamino)-2-pyridyl]piperazin-4-yl-carbonyl] pyridine By the same procedure as described example 25, the synthesis was carried out using 2-methyl-2-propaneamine.

Yield: 70%

$^1$H-NMR(CDCl$_3$), ppm: δ1.28(t, 3H), 1.50(s, 9H), 3.15 (m, 6H), 3.71(m, 2H), 3.97(m, 2H), 4.15(m, 1H), 6.05(m, 1H), 6.88(m, 1H), 6.98(m, 1H), 7.70(m, 2H), 8.14(m, 1H), 8.91(m, 1H)

EXAMPLE 30

2-[1-[3-(isopropylamino)-2-pyridyl]piperazin-4-yl-carbonyl]-5-[N-(2-methylpropyl)carbamoyl]pyridine By the same procedure as described example 24, the synthesis was carried out using isobutylamine.

Yield: 82% m.p.: 131~134° C.

$^1$H-NMR(CDCl$_3$), ppm: δ1.01(d, 6H), 1.25(d, 6H), 1.95 (m, 1H), 3.13(m, 2H), 3.21(m, 2H), 3.33(m, 2H), 3.57(m, 1H), 3.72(m, 2H), 3.98(m, 2H), 4.16(m, 1H), 6.40(m, 1H), 6.89(m, 1H), 6.98(m, 1H), 7.70(m, 2H), 8.19(m, 1H), 8.95 (m, 1H)

EXAMPLE 31

2-[1-[3-(ethylamino)-2-pyridyl]piperazin-4-yl-carbonyl]-5-[N-(2-methylpropyl)carbamoyl]pyridine By the same procedure as described example 24, the synthesis was carried out starting with 6-[1-[3-(ethylamino)-

2-pyridyl]piperazin-4-yl-carbonyl]nicotinic acid and using isobutylamine. And then, the product was recrystallized with ethanol and hexane to give a desired compound.

Yield: 77%

$^1$H-NMR(CDCl$_3$), ppm: δ1.01(d, 6H), 1.28(t, 3H), 1.96 (m, 1H), 3.14(m, 4H), 3.23(m, 2H), 3.34(m, 2H), 3.72(m, 2H), 3.98(m, 2H), 4.16(m, 1H), 6.39(m, 1H), 6.90(m, 1H), 6.98(m, 1H), 7.71(m, 2H), 8.19(m, 1H), 8.96(m, 1H)

EXAMPLE 32

2-[1-(3-amino-2-pyridyl)piperazin-4-yl-carbonyl]-5-[N-(2-methylpropyl)carbamoyl]pyridine Step (1): Preparation of 5-[N-(2-methylpropyl)carbamoyl]-2-[1-(3-nitro-2-pyridyl)piperazin-4-yl-carbonyl]pyridine By the same procedure as described Step (1) of example 27, the synthesis was carried out using isobutylamine.

Yield: 80%

$^1$H-NMR(CDCl$_3$), ppm: δ1.02(d, 6H), 1.96(m, 1H), 3.13 (m, 2H), 3.21(m, 2H), 3.33(m, 2H), 3.72(m, 2H), 3.98(m, 2H), 6.89(m, 1H), 6.98(m, 1H), 7.70(m, 2H), 8.20(m, 1H), 8.94(m, 1H)

Step (2): Preparation of 2-[1-(3-amino-2-pyridyl)piperazin-4-yl-carbonyl]-5-[N-(2-methylpropyl)carbamoyl]pyridine By the same procedure as described in the step (2) of example 27, the synthesis was carried out starting with 5-[N-(2-methylpropyl)carbamoyl]-2-[1-(3-nitro-2-pyridyl)piperazin-4-yl-carbonyl]pyridine, so prepared by Step (1) and using isobutylamine. And then, the product was recrystallized with ethanol and ether to give a desired compound.

Yield: 72%

$^1$H-NMR(CDCl$_3$), ppm: δ1.01(d, 6H), 1.96(m, 1H), 3.12 (m, 2H), 3.22(m, 2H), 3.34(m, 2H), 3.73(m, 2H), 3.98(m, 2H), 6.39(m, 1H), 6.89(m, 1H), 6.97(m, 1H), 7.65(m, 1H), 7.78(m, 1H), 8.19(m, 1H), 8.97(m, 1H)

EXAMPLE 33

5-(N,N-diethylcarbamoyl)-2-[1-[3-(isopropylamino)-2-pyridyl]piperazin-4-yl-carbonyl]pyridine By the same procedure as described in the example 24, the synthesis was carried out starting with 6-[1-[3-(isopropylamino)-2-pyridyl]piperazin-4-yl-carbonyl] nicotinic acid. And then, the product was recrystallized with ethanol and tetrahydrofuran to give a desired compound.

Yield: 78% m.p.: 100~102° C.

$^1$H-NMR(CDCl$_3$), ppm: δ1.13(m, 3H), 1.24(m, 9H), 3.10 (m, 2H), 3.18(m, 2H), 3.27(m, 2H), 3.56(m, 3H), 3.74(m, 2H), 3.97(m, 2H), 4.17(m, 1H), 6.86(m, 1H), 6.96(m, 1H), 7.70(m, 2H), 7.81(m, 1H), 8.63(m, 1H)

EXAMPLE 34

5-(N,N-diisopropylcarbamoyl)-2-[1-[3-(ethylamino)-2-pyridyl]piperazin-4-yl-carbonyl]pyridine By the same procedure as described in the example 24, the synthesis was carried out starting with 6-[1-[3-(ethylamino)-2-pyridyl]piperazin-4-yl-carbonyl]nicotinic acid and using diisopropylamine. And then, the product was recrystallized with acetone and hexane to give a desired compound.

Yield: 72%

$^1$H-NMR(CDCl$_3$), ppm: δ1.15(m, 6H), 1.24(m, 12H), 3.10(m, 2H), 3.18(m, 2H), 3.53(m, 3H), 3.60(m, 2H), 3.95 (m, 2H), 6.87(m, 1H), 6.96(m, 1H), 7.71(m, 2H), 7.81(m, 1H), 8.64(m, 1H)

EXAMPLE 35

5-(N-cyclopropylcarbamoyl)-2-[1-[3-(isopropylamino)-2-pyridyl]piperazin-4-yl-carbonyl] pyridine By the same procedure as described in the example 25, the synthesis was carried out starting with 6-[1-[3-(isopropylamino)-2-pyridyl]piperazin-4-yl-carbonyl] nicotinic acid methyl ester and using cyclopropylamine. And then, the product was recrystallized with isopropanol and petroleum ether to give a desired compound.

Yield: 77% m.p.: 188~190° C.

$^1$H-NMR(CDCl$_3$), ppm: δ0.71(m, 2H), 0.84(m, 2H), 1.25 (d, 6H), 2.93(m, 1H), 3.05(m, 2H), 3.16(m, 2H), 3.55(m, 1H), 3.63(m, 2H), 3.95(m, 2H), 4.15(m, 1H), 6.83(m, 1H), 6.93(m, 1H), 7.38(m, 1H), 7.49(m, 1H), 7.67(m, 1H), 8.09 (m, 1H), 8.87(m, 1H)

EXAMPLE 36

5-(N-cyclopropylcarbamoyl)-2-[1-[3-(isopropylamino)-2-pyridyl]piperazin-4-yl-carbonyl] pyridine By the same procedure as described in the example 25, the synthesis was carried out starting with 6-[1-[3-(isopropylamino)-2-pyridyl]piperazin-4-yl-carbonyl] nicotinic acid methyl ester and using cyclopropylamine. And then, the product was recrystallized with ethanol and hexane to give a desired compound.

Yield: 69% m.p.: 164~165° C.

$^1$H-NMR(CDCl$_3$), ppm: δ0.65(m, 2H), 0.87(m, 2H), 0.98 (d, 6H), 1.90(m, 1H), 2.89(m, 3H), 3.04(m, 2H), 3.16(m, 2H), 3.64(m, 2H), 3.94(m, 2H), 4.32(m, 1H), 5 6.78(m, 2H), 6.89(m, 1H), 7.57(m, 1H), 7.65(m, 1H), 8.08(m, 1H), 8.86(s, 1H)

EXAMPLE 37

5-(N-cyclopentylcarbamoyl)-2-[1-[3-(isopropylamino)-2-pyridyl]piperazin-4-yl-carbonyl] pyridine By the same procedure as described in the example 24, the synthesis was carried out using cyclopentylamine.

Yield: 83% m.p.: 197~199° C.

$^1$H-NMR(CDCl$_3$), ppm: δ1.25(d, 6H), 1.56(m, 2H), 1.67–1.76(m, 4H), 2.13(m, 2H), 3.12(m, 2H), 3.20(m, 2H), 3.56(m, 1H), 3.71(m, 2H), 3.97(m, 2H), 4.17(m, 1H), 4.43 (m, 1H), 6.39(m, 1H), 6.89(m, 1H), 6.96(m, 1H), 7.68(m, 2H), 8.16(m, 1H), 8.92(m, 1H)

EXAMPLE 38

5-(N-cyclopentylcarbamoyl)-2-[1-[3-(ethylamino)-2-pyridyl]piperazin-4-yl-carbonyl]pyridine By the same procedure as described in the example 24, the synthesis was carried out starting with 6-[1-[3-(ethylamino)-2-pyridyl]piperazin-4-yl-carbonyl]nicotinic acid and using cyclopentylamine. And then, the product was recrystallized with isopropanol and ether to give a desired compound.

Yield: 76%

$^1$H-NMR(CDCl$_3$), ppm: δ1.28(t, 3H), 1.56(m, 2H), 1.68–1.77(m, 4H), 2.14(m, 2H), 3.17(m, 6H), 3.70(m, 2H), 3.98(m, 2H), 4.16(m, 1H), 4.44(m, 1H), 6.30(m, 1H), 6.87 (m, 1H), 6.95(m, 1H), 7.66(m, 2H), 8.16(m, 1H), 8.90(m, 1H)

EXAMPLE 39

2-[1-[3-(isopropylamino)-2-pyridyl]piperazin-4-yl-carbonyl]-5-[N-(2-methoxyethyl)carbamoyl]pyridine By the same procedure as described in the example 25, the synthesis was carried out starting with 6-[1-[3-(isopropylamino)-2-pyridyl]piperazin-4-yl-carbonyl] nicotinic acid methyl ester and using 2-methoxyethylamine. And then, the product was recrystallized with methylene chloride and hexane to give a desired compound.

Yield: 73% m.p.: 122~124° C.

$^1$H-NMR(CDCl$_3$), ppm: δ1.23(d, 6H), 3.09(m, 2H), 3.16 (m, 2H), 3.38(s, 3H), 3.55(m, 3H), 3.67(m, 4H), 3.95(m, 2H), 4.13(m, 1H), 6.67(m, 1H), 6.84(m, 1H), 6.95(m, 2H), 7.69(m, 2H), 8.17(m, 1H), 8.94(m, 1H)

EXAMPLE 40

2-[1-[3-(ethylamino)-2-pyridyl]piperazin-4-yl-carbonyl]-5-[N-(2-methoxyethyl)carbamoyl]-pyridine By the same procedure as described in the example 25, the synthesis was carried out using 2-methoxyethylamine.

Yield: 70.5% m.p.: 115~116° C.

$^1$H-NMR(CDCl$_3$), ppm: δ1.31(t, 3H), 3.14(m, 4H), 3.21 (m, 2H), 3.40(s, 3H), 3.57(m, 2H), 3.70(m, 4H), 3.98(m, 2H), 4.21(m, 1H), 6.71(m, 1H), 6.86(m, 1H), 6.96(m, 1H), 7.72(m, 2H), 8.20(m, 1H), 8.98(m, 1H)

EXAMPLE 41

2-[1-[3-(isobutylamino)-2-pyridyl]piperazin-4-yl-carbonyl]-5-[N-(2-methoxyethyl)carbamoyl]-pyridine By the same procedure as described in the example 25, the synthesis was carried out starting with 6-[1-[3-(isobutylamino)-2-pyridyl]piperazin-4-yl-carbonyl] nicotinic acid methyl ester and using 2-methoxyethylamine. And then, the product was recrystallized with isopropanol to give a desired compound.

Yield: 65% m.p.: 123~125° C.

$^1$H-NMR(CDCl$_3$), ppm: δ0.99(d, 6H), 1.89(m, 1H), 2.88 (m, 2H), 3.07(m, 2H), 3.16(m, 2H), 3.37(s, 3H), 3.55(m, 2H), 3.65(m, 4H), 3.95(m, 2H), 4.33(m, 1H), 6.79(m, 2H), 6.90(m, 1H), 7.67(m, 2H), 8.16(m, 1H), 8.94(s, 1H)

EXAMPLE 42

5-[N,N-bis(2-methoxyethyl)carbamoyl]-2-[1-[3-(isopropylamino)-2-pyridyl]piperazin-4-yl-carbonyl]pyridine.HCl Triethylamine (0.8 ml) was added to 6-[1-[3-(isopropylamino)-2-pyridyl]piperazin-4-yl-carbonyl] nicotinic acid (2 g) in methylene chloride (30 ml) for dissolution and cooled. With the slow addition of pivaloyl chloride (0.7 ml) at 0° C.~5° C., the mixture was stirred at 5° C. for 1 hour. With the addition of N,N-diisopropylethylamine (1 ml) and bis(2-methoxyethyl) amine (0.85 ml), the mixture was stirred at 10° C. for 3 hours. The reaction mixture was washed with an aqueous sodium bicarbonate and water twice. The separated organic layer was dried over magnesium sulfate and concentrated under reduced pressure. The residue was dissolved in chloroform and with the slow addition of 4.5 ml of anhydrous 1N-hydrochloric acid (solution in isopropanol), crystals were precipitated. After mixture was stirred for 1 hour, and then filtered. The crystals, so separated, was recrystallized with methylene chloride and hexane to give a desired compound of 1.92 g (yield: 68%) as a hydrochloride salt.

$^1$H-NMR(CDCl$_3$), ppm: δ1.33(d, 6H), 3.31–3.39(m, 6H), 3.48(m, 2H), 3.54(m, 6H), 3.66(m, 3H), 3.78(m, 2H), 3.95 (m, 2H), 4.04(m, 2H), 7.28(m, 2H), 7.79(m, 1H), 7.88(m, 1H), 7.97(m, 1H), 8.67(m, 1H)

EXAMPLE 43

2-[1-[3-(isopropylamino)-2-pyridyl]piperazin-4-yl-carbonyl]-5-[N-( 2-methoxy-1-methylethyl) carbamoyl]pyridine By the same procedure as described in the example 24, the synthesis was carried out using 2-methoxyisopropylamine.

Yield: 79% m.p.: 134~135° C.

$^1$H-NMR(CDCl$_3$), ppm: δ1.24(d, 6H), 1.33(d, 3H), 3.10 (m, 2H), 3.18(m, 2H), 3.40(s, 3H), 3.46(m, 1H), 3.54(m, 2H), 3.72(m, 2H), 3.97(m, 2H), 4.15(m, 1H), 4.37(m, 1H), 6.54(m, 1H), 6.86(m, 1H), 6.95(m, 1H), 7.69(m, 2H), 8.17 (m, 1H), 8.96(m, 1H)

EXAMPLE 44

2-[1-[3-(ethylamino)-2-pyridyl]piperazin-4-yl-carbonyl]-5-[N-(2-methoxy-1-methylethyl) carbamoyl]pyridine By the same procedure as described in the example 24, the synthesis was carried out starting with 6-[1-[3-(ethylamino)-2-pyridyl]piperazin-4-yl-carbonyl]nicotinic acid and using 2-methoxyisopropylamine. And then, the product was recrystallized with isopropanol and hexane to give a desired compound.

Yield: 82%

$^1$H-NMR(CDCl$_3$), ppm: δ1.30(t, 3H), 1.34(d, 3H), 3.14 (m, 4H), 3.19(m, 2H), 3.41(s, 3H), 3.52(m, 2H), 3.72(m, 2H), 3.96(m, 2H), 4.15(m, 1H), 4.38(m, 1H), 6.56(m, 1H), 6.86(m, 1H), 6.97(m, 1H), 7.70(m, 2H), 8.16(m, 1H), 8.98 (m, 1H)

EXAMPLE 45

2-[1-[3-(isopropylamino)-2-pyridyl]piperazin-4-yl-carbonyl]-5-[N-(3-methoxypropyl)carbamoyl] pyridine By the same procedure as described in the example 24, the synthesis was carried out using 3-methoxypropylamine. And then, the product was recrystallized with ethanol and isopropyl ether to give a desired compound.

Yield: 77% m.p.: 95~96° C.

$^1$H-NMR(CDCl$_3$), ppm: δ1.25(d, 6H), 1.93(m, 2H), 3.15–3.21(m, 4H), 3.40(s, 3H), 3.62(m, 5H), 3.73(m, 2H), 3.98(m, 2H), 4.17(m, 1H), 6.89(m, 1H), 6.99(m, 1H), 7.27 (m, 1H), 7.73(m, 2H), 8.19(m, 1H), 8.94(m, 1H)

EXAMPLE 46

2-[1-[3-(ethylamino)-2-pyridyl]piperazin-4-yl-carbonyl]-5-[N-(3-methoxypropyl)carbamoyl]pyridine By the same procedure as described in the example 25, the synthesis was carried out using 3-methoxypropylamine. And then, the product was recrystallized with acetonitrile and ether to give a desired compound.

Yield: 72%

$^1$H-NMR(CDCl$_3$), ppm: δ1.29(t, 3H), 1.93(m, 2H), 3.15–3.20(m, 6H), 3.41(s, 3H), 3.60(m, 4H), 3.73(m, 2H), 3.98(m, 2H), 4.17(m, 1H), 6.89(m, 1H), 6.98(m, 1H), 7.27(m, 1H), 7.73(m, 2H), 8.19(m, 1H), 8.94(m, 1H)

EXAMPLE 47

2-[1-[3-(isobutylamino)-2-pyridyl]piperazin-4-yl-carbonyl]- 5-[N-(3-methoxypropyl)carbamoyl]pyridine By the same procedure as described in the example 25, the synthesis was carried out starting with 6-[1-[3-(isobutylamino)-2-pyridyl]piperazin-4-yl-carbonyl]nicotinic acid methyl ester and using 3-methoxypropylamine. And then, the product was recrystallized with methanol and isopropyl ether to give a desired compound.

Yield: 64% m.p.: 109~110° C.

$^1$H-NMR(TFA-d$_1$), ppm: δ1.25(d, 6H), 2.19(m, 1H), 2.33(m, 2H), 3.28(d, 2H), 3.74(s, 3H), 3.82(m, 4H), 3.94(m, 2H), 4.02(m, 2H), 4.21(m, 2H), 4.42(m, 2H), 7.65(m, 1H), 7.73(m, 1H), 7.80(m, 1H), 8.62(m, 1H), 9.42(m, 1H), 9.78(s, 1H)

EXAMPLE 48

5-[N-[2-(2-hydroxyethoxy)ethyl]carbamoyl]-2-[1-[3-(isopropylamino)-2-pyridyl]piperazin-4-yl-carbonyl]pyridine By the same procedure as described in the example 25, the synthesis was carried out starting with 6-[1-[3-(isopropylamino)-2-pyridyl]piperazin-4-yl-carbonyl]nicotinic acid methyl ester and using 2-(2-aminoethoxy)ethanol. And then, the product was recrystallized with acetone and hexane to give a desired compound.

Yield: 79% m. p.: 93~95° C.

$^1$H-NMR(CDCl$_3$), ppm: δ1.25(d, 6H), 3.10(m, 2H), 3.21(m, 2H), 3.52(m, 1H), 3.67(m, 8H), 3.77(m, 2H), 3.96(m, 2H), 4.17(m, 1H), 6.86(m, 1H), 6.95(m, 1H), 7.49(m, 1H), 7.68(m, 2H), 8.18(m, 1H), 8.97(m, 1H)

EXAMPLE 49

2-[1-[3-(ethylamino)-2-pyridyl]piperazin-4-yl-carbonyl]-5-[N-[2-(2-hydroxyethoxy)ethyl]carbamoyl]pyridine By the same procedure as described in the example 25, the synthesis was carried out using 2-(2-aminoethoxy)ethanol.

Yield: 75%

$^1$H-NMR(CDCl$_3$), ppm: δ1.30(t, 3H), 3.14(m, 4H), 3.21(m, 2H), 3.67(m, 8H), 3.76(m, 2H), 3.96(m, 2H), 4.16(m, 1H), 6.87(m, 1H), 6.95(m, 1H), 7.49(m, 1H), 7.68(m, 2H), 8.18(m, 1H), 8.97(m, 1H)

EXAMPLE 50

5-[N-(2,2-dimethoxyethyl)-N-methylcarbamoyl]-2-[1-[3-(isopropylamino)-2-pyridyl]piperazin-4-yl-carbonyl]pyridine.HCl By the same procedure as described in the example 42, the synthesis was carried out starting with 6-[1-[3-(isopropylamino)-2-pyridyl]piperazin-4-yl-carbonyl]nicotinic acid and using methylaminoacetaldehyde dimethyl acetal to give a desired compound as a hydrochloride salt.

Yield: 70%

$^1$H-NMR(CDCl$_3$), ppm: δ1.33(d, 6H), 3.15(s, 3H), 3.50(m, 8H), 3.66(m, 1H), 3.94(m, 4H), 4.10(m, 4H), 4.70(m, 2H), 7.34(m, 2H), 7.85(m, 2H), 8.76(m, 1H), 9.72(m, 1H)

EXAMPLE 51

5-[N-(2,2-dimethoxyethyl)carbamoyl]-2-[1-[3-(isopropylamino)-2-pyridyl]piperazin-4-yl-carbonyl]pyridine By the same procedure as described in the example 24, the synthesis was carried out starting with 6-[1-[3-(isopropylamino)-2-pyridyl]piperazin-4-yl-carbonyl]nicotinic acid and using 2,2-dimethoxyethylamine. And then, the product was crystallized with ethanol and hexane to give a desired compound.

Yield: 78% m.p.: 167~169° C.

$^1$H-NMR(CDCl$_3$), ppm: δ1.16(d, 6H), 3.01(m, 2H), 3.10(m, 2H), 3.38(s, 6H), 3.48(m, 1H), 3.57(m, 2H), 3.64(m, 2H), 3.90(m, 2H), 4.08(m, 1H), 4.44(m, 1H), 6.44(m, 1H), 6.78(m, 1H), 6.86(m, 1H), 7.61(m, 2H), 8.12(m, 1H), 8.90(s, 1H)

EXAMPLE 52

5-[N-[(1,3-Dioxolan-2-yl)methyl]-N-methylcarbamoyl]-2-[1-[3-(isopropylamino)-2-pyridyl]piperazin-4-yl-carbonyl]pyridine By the same procedure as described in the example 24, the synthesis was carried using 2-methylaminomethyl-1,3-dioxolan.

Yield: 67% m.p.: 108~110° C.

$^1$H-NMR(TFA-d$_1$), ppm: δ1.53(d, 6H), 3.62(s, 3H), 3.70(m, 2H), 3.79(m, 2H), 3.94(m, 2H), 4.11(m, 2H), 4.41(m, 3H), 4.79(m, 1H), 4.92(t, 4H), 7.65(m, 1H), 7.78(m, 2H), 8.53(m, 1H), 9.04(m, 1H), 9.54(s, 1H)

EXAMPLE 53

2-[1-[3-(isopropylamino)-2-pyridyl]piperazin-4-yl-carbonyl]-5-[N-(tetrahydrofuran-2-yl-methyl)carbamoyl]pyridine By the same procedure as described in the example 24, the synthesis was carried out starting with 6-[1-[3-(isopropylamino)-2-pyridyl]piperazin-4-yl-carbonyl]nicotinic acid and using tetrahydrofurfurilamine. And then, the product was crystallized with ethanol and hexane to give a desired compound.

Yield: 83% m.p.: 108~110° C.

$^1$H-NMR(CDCl$_3$), ppm: δ1.26(d, 6H), 1.63(m, 1H), 1.98(m, 2H), 2.07(m, 1H), 3.18–3.23(m, 4H), 3.38(m, 1H), 3.57(m, 1H), 3.78(m, 4H), 3.83(m, 1H), 3.91(m, 2H), 4.09 (m, 1H), 4.11(m, 1H), 6.66(m, 1H), 6.93(m, 1H), 6.99(m, 1H), 7.73(m, 2H), 8.19(m, 1H), 8.98(m, 1H)

EXAMPLE 54

2-[1-[3-(Ethylamino)-2-pyridyl]piperazin-4-yl-carbonyl]-5-[N-(tetrahydrofuran-2-yl-methyl) carbamoyl]pyridine By the same procedure as described in the example 24, the synthesis was carried out starting with 6-[1-[3-(ethylamino)-2-pyridyl]piperazin-4-yl-carbonyl]nicotinic acid and using tetrahydrofurfurilamine. And then, the product was crystallized with ethyl acetate and hexane to give a desired compound.

Yield: 77%

$^1$H-NMR(CDCl$_3$), ppm: δ1.29(t, 3H), 1.63(m, 1H), 1.99 (m, 2H), 2.06(m, 1H), 3.18 3.22(m, 6H), 3.38(m, 1H), 3.78(m, 4H), 3.82(m, 1H), 3.92(m, 2H), 4.09(m, 1H), 4.11 (m, 1H), 6.67(m, 1H), 6.92(m, 1H), 6.98(m, 1H), 7.73(m, 1H), 8.19(m, 1H), 8.99(m, 1H)

EXAMPLE 55

2-[1-[3-(Isopropylamino)-2-pyridyl]piperazin-4-yl-carbonyl]-5-[N-(tetrahydro-2-fuanon-3-yl) carbamoyl]pyridine Triethylamine (0.8 ml) was added to 6-[1-[3-(isopropylamino)-2-pyridyl]piperazin-4-yl-carbonyl] nicotinic acid (2 g) in methylene chloride (40 ml) for dissolution and cooled. With the slow addition of pivaloyl chloride (0.7 ml) at 0° C.~5° C., the mixture was stirred at 5° C for 1 hour. With the addition of triethylamine (2.2 ml) and α-amino-γ-butylrolactone hydrobromide (1.4 g), the mixture was stirred at 10° C. for 3 hours. The reaction mixture was washed with an aqueous sodium bicarbonate and water twice. The separated organic layer was dried over magnesium sulfate and concentrated under reduced pressure. The residue was dissolved in a small amount of chloroform and with the addition of ether, crystals were precipitated. The mixture was stirred for 1 hour and filtered. The solid was recrystallized with acetonitrile and hexane to give a desired compound of 1.84 g (yield: 75%).

m.p.: 199~201° C.

$^1$H-NMR(CDCl$_3$), ppm: δ1.25(d, 6H), 2.42(m, 1H), 2.83 (m, 1H), 3.10(m, 2H), 3.18(m, 2H), 3.56(m, 1H), 3.67(m, 2H), 3.96(m, 2H), 4.13(m, 1H), 4.36(m, 1H), 4.55(m, 1H), 4.81(m, 1H), 6.86(m, 1H), 6.95(m, 1H), 7.68(m, 2H), 7.81 (m, 1H), 8.19(m, 1H), 8.97(m, 1H)

EXAMPLE 56

2-[1-(3-amino-2-pyridyl)piperazin-4-yl-carbonyl]-5-[N-(tetrahydro-2-furanon-3-yl)carbamoyl]pyridine 6-[1-(3-amino-2-pyridyl)piperazin-4-yl-carbonyl] nicotinic acid (1 g) was added to a co-solvent of tetrahydrofuran (25 ml) and methylene chloride (15 ml) and with the successive addition of 1.3-dicyclohexylcarbodimide (1.3 g) and 1-hydroxybenzotriazole (0.46 g) at 15° C.~20° C., the mixture was stirred for 2 hours. A mixture of α-amino-γ-butyrolactone hydrobromide (1.1 g) and triethylamine (0.9 ml) was added again to the mixture at 20° C. and stirred at 20° C.~25° C. for 3 hours. With the addition of methylene chloride (50 ml), the mixture was washed with water 3 times, dried over magnesium sulfate and concentrated under reduced pressure. The concentrated residue was treated with ether for crystallization and recrystallized with chloroform and tetrahydrofuran to give a desired compound of 1.07 g (yield: 71%).

$^1$H-NMR(CDCl$_3$), ppm: δ2.44(m, 1H), 2.67(m, 1H), 3.18 (m, 2H), 3.26(m, 2H), 3.70(m, 2H), 3.98(m, 2H), 4.35(m, 1H), 4.53(m, 1H), 4.87(m, 1H), 6.92(m, 1H), 7.12(m, 1H), 7.72(m, 2H), 8.38(m, 1H), 9.14(m, 2H)

EXAMPLE 57

2-[1-[3-(isopropylamino)-2-pyridyl]piperazin-4-yl-carbonyl]-5-[N-(tetrahydro-2-thiophenon-3-yl) carbamoyl]pyridine By the same procedure as described in the example 55, synthesis was carried out using homocysteine thiolactone hydrochloride.

Yield: 68% m.p.: 195~196° C.

$^1$H-NMR(CDCl$_3$), ppm: δ1.26(d, 6H), 2.21(m, 1H), 2.96 (m, 1H), 3.08(m, 2H), 3.17(m, 2H), 3.32(m, 1H), 3.41(m, 1H), 3.54(m, 1H), 3.64(m, 2H), 3.96(m, 2H), 4.12(m, 1H), 4.81(m, 1H), 6.84(m, 1H), 6.95(m, 1H), 7.47(m, 1H), 7.68 (m, 2H), 8.17(m, 1H), 8.96(m, 1H)

EXAMPLE 58

2-[1-[3-(isopropylamino)-2-pyridyl]piperazin-4-yl-carbonyl]-5-[N-[3-(2-pyrrolidinon-1-yl)propyl] carbamoyl]pyridine.HCl By the same procedure as described in the example 42, synthesis was carried out starting with 6-[1-[3-(isopropylamino)-2-pyridyl]piperazin-4-yl-carbonyl] nicotinic acid and using 1-(3-aminopropyl)-2-pyrrolidinone.

Yield: 63%

$^1$H-NMR(TFA-d$_1$), ppm: δ1.64(d, 6H), 2.43(m, 2H), 2.63 (m, 2H), 3.28(m, 2H), 3.95(m, 8H), 4.10(m, 3H), 4.30(m, 2H), 4.51(m, 2H), 7.79(m, 1H), 7.93(m, 2H), 8.76(m, 1H), 9.56(m, 1H), 9.92(s, 1H)

EXAMPLE 59

2-[1-[3-(isopropylamino)-2-pyridyl]piperazin-4-yl-carbonyl]-5-[N-[2-(morpholin-4-yl) ethyl] carbamoyl]pyridine By the same procedure as described in the example 24, synthesis was carried out using 4-(2-aminoethyl) morpholine.

Yield: 75%

$^1$H-NMR(CDCl$_3$), ppm: δ1.24(d, 6H), 2.62(m, 4H), 2.72 (m, 2H), 3.08(m, 2H), 3.18(m, 2H), 3.53(m, 1H), 3.63(m, 2H), 3.72(m, 2H), 3.80(m, 4H), 3.98(m, 2H), 4.15(m, 1H), 6.84(m, 1H), 6.94(m, 1H), 7.67(m, 1H), 7.76(m, 1H), 8.26 (m, 1), 8.99(m, 1H)

EXAMPLE 60

2-[1-[3-(ethylamino)-2-pyridyl]piperazin-4-yl-carbonyl]-5-[N-[2-(morpholin4-yl)ethyl]carbamoyl] pyridine.HCl By the same procedure as described in the example 42, synthesis was carried out starting with 6-[1-[3-(ethylamino)-2-pyridyl]piperazin-4-yl-carbonyl]nicotinic acid and using 4-(2-aminoethyl)morpholine.

Yield: 70% m.p.: 223~225° C.

$^1$H-NMR(TFA-d$_1$), ppm: δ1.48(t, 3H), 3.45(m, 4H), 3.82 (m, 6H), 4.02(m, 2H), 4.13(m, 2H), 4.30(m, 6H), 4.47(m, 2H), 7.56(m, 1H), 7.67(m, 1H), 7.77(m, 1H), 8.59(m, 1H), 9.43(m, 1H), 9.80(m, 1H)

EXAMPLE 61

2-[1-(3-amino-2-pyridyl)piperazin-4-yl-carbonyl]-5-[N-[2-(morpholin-4-yl)ethyl]carbamoyl]pyridine By the same procedure as described in the example 56, synthesis was carried out using 4-(2-aminoethyl) morpholine. And then, the product was recrystallized with ethyl acetate and ether to give a desired compound.

Yield: 73%

$^1$H-NMR(CDCl$_3$), ppm: δ2.63(m, 4H), 2.74(m, 2H), 3.08 (m, 2H), 3.18(m, 2H), 3.64(m, 2H), 3.73(m, 2H), 3.83–3.96 (m, 6H), 6.84(m, 1H), 6.95(m, 1H), 7.67(m, 1H), 7.76(m, 1H), 8.26(m, 1H), 8.98(m, 1H)

EXAMPLE 62

5-[N-[2-(dimethylamino)ethyl]carbamoyl]-2-[1-[3-(isopropylamino)-2-pyridyl]piperazin-4-yl-carbonyl] pyridine.HCl By the same procedure as described in the example 42, synthesis was carried out using N,N-dimethylethylenediamine. And then, the product was recrystallized with acetone and petroleum ether to give a desired compound as hydrochloride salt.

Yield: 72%

$^1$H-NMR(CDCl$_3$), ppm: δ1.24(d, 6H), 2.84(s, 6H), 3.10 (m, 4H), 3.26(m, 2H), 3.54(m, 3H), 3.95(m, 4H), 4.16(m, 1H), 6.83(m, 1H), 6.92(m, 1H), 7.67(m, 2H), 8.49(m, 1H), 8.96(m, 1H), 9.26(m, 1H)

EXAMPLE 63

5-[N-[2-(dimethylamino)ethyl]carbamoyl]-2-[1-[3-(ethylamino)-2-pyridyl]piperazin-4-yl-carbonyl] pyridine.HCl By the same procedure as described in the example 42, synthesis was carried out starting with 6-[1-[3-(ethylamino)-2-pyridyl]piperazin-4-yl-carbonyl]nicotinic acid and using N,N-dimethylethylenediamine. And then, the product was recrystallized with acetone and ether to give a desired compound as a hydrochloride salt.

Yield: 67%

$^1$H-NMR(CDCl$_3$), ppm: δ1.28(t, 3H), 2.79(s, 6H), 3.10 (m, 6H), 3.26(m, 2H), 3.54(m, 2H), 3.93(m, 4H), 4.16(m, 1H), 6.82(m, 1H), 6.93(m, 1H), 7.67(m, 2H), 8.46(m, 1H), 8.97(m, 1H), 9.26(m, 1H)

EXAMPLE 64

5-[N-[2-(diethylamino)ethyl]carbamoyl]-2-[1-[3-(isopropylamino)-2-pyridyl]piperazin-4-yl-carbonyl] pyridine.HCl By the same procedure as described in the example 42, synthesis was carried out using 2-(diethylamino)ethylamine.

Yield: 76%

$^1$H-NMR(CDCl$_3$), ppm: δ1.02(m, 6H), 1.25(d, 6H), 3.10 (m, 8H), 3.27(m, 2H), 3.53(m, 3H), 3.95(m, 4H), 4.16(m, 1H), 6.83(m, 1H), 6.94(m, 1H), 7.67(m, 2H), 8.47(m, 1H), 8.97(m, 1H), 9.27(m, 1H)

EXAMPLE 65

5-[N-[3-(dimethylamino)propyl]-N-methylcarbamoyl]-2-[1-[3-(isopropylamino)-2-pyridyl]piperazin-4-yl-carbonyl]pyridine By the same procedure as described in the example 24, synthesis was carried out using N,N,N'-trimethyl-1,3-propanediamine. And then, the product was recrystallized with acetonitrile and isopropyl ether to give a desired compound.

Yield: 70%

$^1$H-NMR(CDCl$_3$), ppm: δ1.25(d, 6H), 2.80(s, 6H), 3.01(s, 3H), 3.10(m, 4H), 3.26(m, 2H), 3.54(m, 3H), 3.95(m, 4H), 4.16(m, 1H), 6.83(m, 1H), 6.92(m, 1H), 7.67(m, 2H), 8.96 (m, 1H), 9.26(m, 1H)

EXAMPLE 66

6-[1-[3-(isopropylamino)-2-pyridyl]piperazin-4-yl-carbonyl]-N-(5-methyl-1H-pyrazol-3-yl) nicotinamide Triethylamine (0.8 ml) was added to 6-[1-[3-(isopropylamino)-2-pyridyl]piperazin-4-yl-carbonyl] nicotinic acid (2 g) in methylene chloride (30 ml) for dissolution and cooled. With the slow addition of pivaloyl chloride (0.7 ml) at 0° C.~5° C., the mixture was stirred at 5° C. for 1 hour. With the addition of triethylamine (0.9 ml) and 3-amino-5-methylpyrazole (0.56 g), the mixture was stirred at 5° C.~10° C. for 3 hours. The solution was slowly heated and stirred at 15° C.~20° C. for 30 minutes. The solution was washed with an aqueous sodium bicarbonate and water twice. The separated organic layer was concentrated under reduced pressure. The concentrated residue was chromatographed on column (chloroform/isopropanol=10/1, v/v). The purified solution was recovered and concentrated under reduced pressure. The residue was treated with ether for crystallization and with the addition of isopropyl ether (20 ml), and stirred for 2 hours, filtered and washed to give a desired compound of 1.77 g (yield: 73%).

m.p.: 116~117° C.

$^1$H-NMR(CDCl$_3$), ppm: δ1.26(d, 6H), 2.17(s, 3H), 3.12 (m, 2H), 3.21(m, 2H), 3.55(m, 1H), 3.78(m, 2H), 3.99(m, 2H), 4.16(m, 1H), 5.34(s, 1H), 5.63(bs, 1H), 6.86(m, 1H), 6.96(m, 1H), 7.70(m, 1H), 7.76(m, 1H), 8.53(m, 1H), 9.25 (m, 1H)

EXAMPLE 67

6-[1-[3-(isopropylamino)-2-pyridyl]piperazin-4-yl-carbonyl]-N-(5-methylisoxazol-3-yl)nicotinamide By the same procedure as described in the example 66, synthesis was carried out using 3-amino-5-methylisoxazole.

Yield: 75%

$^1$H-NMR(CDCl$_3$), ppm: δ1.25(d, 6H), 2.44(s, 3H), 3.16 (m, 4H), 3.55(m, 1H), 3.75(m, 2H), 3.98(m, 2H), 4.15(m, 1H), 6.87(m, 2H), 6.96(m, 1H), 7.68(m, 1H), 7.77(m, 1H), 8.39(m, 1H), 9.15(m, 1H), 10.40(s, 1H)

EXAMPLE 68

6-[1-[3-(isopropylamino)-2-pyridyl)piperazin-4-yl-carbonyl]-N-(4-methyl-1,3-thiazol-2-yl)nicotinamide By the same procedure as described in the example 66, synthesis was carried out using 2-amino-4-methylthiazole.

Yield: 69% m.p.: 128~130° C.

$^1$H-NMR(CDCl$_3$), ppm: δ1.25(d, 6H), 2.21(s, 3H), 3.14 (m, 4H), 3.56(m, 1H), 3.73(m, 2H), 4.01(m, 2H), 4.16(m, 1H), 6.61(s, 1H), 6.88(m, 1H), 6.96(m, 1H), 7.70(m, 1H), 7.76(m, 1H), 8.35(m, 1H), 9.13(m, 1H)

EXAMPLE 69

6-[1-[3-(isopropylamino)-2-pyridyl]piperazin-4-yl-carbonyl]-N-(1,3,4-thiadiazol-2-yl)nicotinamide By the same procedure as described in the example 66, synthesis was carried out using 2-amino-1,3,4-thiadiazole. And then, the product was recrystallized with ethyl acetate and hexane to give a desired compound.

Yield: 64% m.p.: 260~262° C.

$^1$H-NMR(TFA-d$_1$), ppm: δ1.45(d, 6H), 3.67(m, 4H), 3.86 (m, 1H), 4.09(m, 2H), 4.34(m, 2H), 7.56(m, 1H), 7.72(m, 2H), 8.61(m, 1H), 9.53(m, 1H), 9.92(m, 2H)

EXAMPLE 70

6-[1-[3-(isopropylamino)-2-pyridyl]piperazin-4-yl-carbonyl]-N-(2-pyridyl)nicotinamide Thionyl chloride (0.3 ml) was added to 6-[1-[3-(isopropylamino-2-pyridyl]piperazin-4-yl-carbonyl] nicotinic acid (1 g) in methylene chloride (25 ml), and the mixture was heated and stirred at 35° C. for 2 hours. With the addition of 2-aminopyridine (1 g) and acetonitrile (5 ml), the mixture was stirred at 30° C.~35° C. ° C. for 5 hours. The mixture was cooled to room temperature and washed with water and an aqueous sodium bicarbonate. The separated organic layer was concentrated under reduced pressure. The concentrated residue was chromatographed on column (hexane/chloroform/methanol=5/4/2, v/v/v). The purified solution was recovered and concentrated under reduced pressure. The residue was treated with ether (25 ml) for crystallization. After a 1-hour stirring, the residue was filtered and washed to give a desired compound of 0.86 g (yield: 71%).

m.p.: 164~165° C.

$^1$H-NMR(CDCl$_3$), ppm: δ1.23(d, 6H), 3.14(m, 4H), 3.52 (m, 1H), 3.71(m, 2H), 3.96(m, 2H), 4.15(m, 1H), 6.83(m, 1H), 6.92(m, 1H), 7.08(m, 1H), 7.65(m, 1H), 7.76(m, 2H), 8.22(m, 1H), 8.34(m, 2H), 9.10(m, 2H)

EXAMPLE 71

6-[1-[3-(isopropylamino)-2-pyridyl]piperazin-4-yl-carbonyl]-N-(6-methoxy-3-pyridyl)nicotinamide By the same procedure as described in the example 70, synthesis was carried out using 5-amino-2-methoxypyridine.

Yield: 63% m.p.: 173~176° C.

$^1$H-NMR(CDCl$_3$), ppm: δ1.25(d, 6H), 3.11(m, 2H), 3.21 (m, 2H), 3.56(m, 1H), 3.76(m, 2H), 3.92(m, 3H), 3.99(m, 2H), 4.16(m, 1H), 6.78(m, 1H), 6.89(m, 1H), 6.97(m, 1H), 7.51(m, 1H), 7.69(m, 1H), 8.16(m, 2H), 8.49(m, 1H), 8.99(s, 1H), 9.36(s, 1H)

EXAMPLE 72

6-[1-[3-(isopropylamino)-2-pyridyl]piperazin-4-yl-carbonyl]-N-(pyrazine-2-yl)nicotinamide By the same procedure as described in the example 70, synthesis was carried out using aminopyrazine.

Yield: 68% m.p.: 209~210° C. $^1$H-NMR(CDCl$_3$), ppm: δ1.23(d, 6H), 3.18(m, 4H), 3.56(m, 1H), 3.72(m, 2H), 3.98(m, 2H), 4.13 (m, 1H), 6.92(m, 2H), 7.67(m, 1H), 7.75(m, 1H), 8.32(m, 2H), 8.42(m, 1H), 8.95(s, 1H), 9.12(m, 1H), 9.67(s, 1H)

EXAMPLE 73

6-[1-[3-(isopropylamino)-2-pyridyl]piperazin-4-yl-carbonyl]-N-(2-pyridylmethyl)nicotinamide.HCl Triethylamine (0.8 ml) was added to 6-[1-[3-(isopropylamino)-2-pyridyl]piperazin-4-yl-carbonyl] nicotinic acid (2 g) in methylene chloride (30 ml) for dissolution and cooled. With the slow addition of pivaloyl chloride (0.7 ml) at 0° C.~5° C., the mixture was stirred at 5° C. for 1 hour. With the addition of N,N-diisopropylethylamine (1 ml) and 2-(aminomethyl)pyridine (0.65 g), the mixture was stirred at 10° C. for 2 hours. The solution was washed with an aqueous sodium bicarbonate and water. The separated organic layer was dried over magnesium sulfate and concentrated under reduced pressure. The concentrated residue was chromatographed on column (chloroform/isopropanol=7/1, v/v). The purified solution was recovered and concentrated under reduced pressure. The residue was dissolved in methylene chloride (20 ml) and with the addition of 1.9 ml of anhydrous hydrochloric acid (2N-ethanol solution), the residue was concentrated under reduced pressure. The residue was dissolved again in methylene chloride (10 ml) and concentrated under reduced pressure. Then, the residue was treated with ether (20 ml) for crystallization and concentrated under reduced pressure to give a desired compound of 1.75 g (yield: 65%) as a hydrochloride salt.

$^1$H-NMR(CDCl$_3$), ppm: δ1.27(d, 6H), 3.25(m, 4H), 3.58 (m, 1H), 3.75(m, 2H), 3.98(m, 2H), 4.15(m, 1H), 4.86(m, 2H), 7.01(m, 2H), 7.43(m, 1H), 7.56(m, 1H), 7.76(m, 2H), 7.92(m, 1H), 8.36(m, 2H), 8.61(m, 1H), 9.12(m, 1H)

EXAMPLE 74

6-[1-[3-(ethylamino)-2-pyridyl]piperazin-4-yl-carbonyl]-N-(2-pyridylmethyl)nicotinamide By the same procedure as described in the example 73, synthesis was carried out starting with 6-[1-[3-(ethylamino)-2-pyridyl]piperazin-4-yl-carbonyl]nicotinic acid and using 2-(aminomethyl)pyridine. And then, the product was chromatographed on column (hexane/methylene chloride/ethyl acetate=2/1/1, v/v/v) and crystallized with ether to give a desired compound.

Yield: 70% m.p.: 129~131° C.

$^1$H-NMR(CDCl$_3$), ppm: δ1.28(t, 3H), 3.21(m, 6H), 3.73 (m, 2H), 3.98(m, 2H), 4.21(m, 1H), 4.80(m, 2H), 6.85(m, 1H), 6.96(m, 1H), 7.25(m, 1H), 7.37(m, 1H), 7.75(m, 3H), 7.98(s, 1H), 8.29(m, 1H), 8.57(m, 1H), 9.10(m, 1H)

EXAMPLE 75

6-[1-(3-amino-2-pyridyl)piperazin-4-yl-carbonyl]-N-(2-pyridylmethyl)nicotinamide.HCl By the same procedure as described in the example 73, synthesis was carried out using 6-[1-(3-amino-2-pyridyl) piperazin-4-yl-carbonyl]nicotinic acid.

Yield: 60%

$^1$H-NMR(TFA-d$_1$), ppm: δ3.92(m, 4H), 4.22(m, 2H), 4.43(m, 2H), 5.37(d, 2H), 7.56(m, 1H), 7.98(m, 2H), 8.19

(m, 1H), 8.38(m, 1H), 8.69(m, 1H), 8.80(m, 1H), 8.98(m, 1H), 9.51(m, 1H), 9.88(s, 1H)

EXAMPLE 76

6-[1-[3-(isopropylamino)-2-pyridyl]piperazin-4-yl-carbonyl]-N-(3-pyridylmethyl)nicotinamide 6-[1-[3-(isopropylamino)-2-pyridyl]piperazin-4-yl-carbonyl]nicotinic acid (2 g) was added to a co-solvent of tetrahydrofuran (30 ml) and methylene chloride (30 ml) and with the successive addition of 1,3-dicyclohexylcarbodimide (2.4 g) and 1-hydroxybenzotriazole (0.85 g) at 15° C.~20° C., the mixture was reacted at the same temperature for 2 hours. With the addition of 3-(aminomethyl)pyridine (0.65 g) at 20° C., the reaction mixture was stirred at 20° C.~25° C. for 2 hours. With the addition of methylene chloride (60 ml). The mixture was washed with water 3 times, dried over magnesium sulfate and concentrated under reduced pressure. The concentrated residue was chromatographed on column (hexane/chloroform/ethanol=5/2/1, v/v/v). The purified solution was concentrated under reduced pressure, and then, the residue was treated with ether for crystallization to give a desired compound of 1.87 g (yield: 75%).

m.p.: 164~166° C.

$^1$H-NMR(CDCl$_3$), ppm: δ1.24(d, 6H), 3.08(m, 2H), 3.16(m, 2H), 3.55(m, 1H), 3.66(m, 2H), 3.92(m, 2H), 4.14(m, 1H), 4.68(m, 2H), 6.84(m, 1H), 6.94(m, 1H), 7.35(m, 1H), 7.62(m, 1H), 7.68(m, 2H), 7.84(m, 1H), 8.19(m, 1H), 8.53(m, 1H), 8.65(m, 1H), 9.01(s, 1H)

EXAMPLE 77

6-[1-[3-(isopropylamino)-2-pyridyl]piperazin-4-yl-carbonyl]-N-(4-pyridylmethyl)nicotinamide By the same procedure as described in the example 76, synthesis was carried out using 4-(aminomethyl)pyridine.

Yield: 72% m.p.: 171~173° C.

$^1$H-NMR(CDCl$_3$), ppm: δ1.24(d, 6H), 3.05(m, 2H), 3.12(m, 2H), 3.55(m, 1H), 3.65(m, 2H), 3.89(m, 2H), 4.15(m, 1H), 4.67(d, 2H), 6.83(m, 1H), 6.94(m, 1H), 7.27(m, 2H), 7.57(m, 1H), 7.66(m, 2H), 8.15(m, 1H), 8.58(m, 2H), 8.97(m, 1H)

EXAMPLE 78

N-[[3-hydroxy-5-(hydroxymethyl)-2-methyl-4-pyridnyl]-6-[1-[3-(isopropylamino)-2-pyridyl]piperazin-4-yl-carbonyl]nicotinamide By the same procedure as described in the example 76, synthesis was carried out using 4-(aminomethyl)-5-hydroxy-6-methyl-3-pyridinemethanol.dihydrochloride and triethylamine (2 equivalents).

Yield: 64% m.p.: 118~122° C.

$^1$H-NMR(CDCl$_3$), ppm: δ1.24(d, 6H), 2.46(s, 3H), 3.04(m, 2H), 3.14(m, 1H), 3.61(m, 3H), 3.92(m, 2H), 4.14(m, 1H), 4.63(d, 2H), 4.73(s, 2H), 6.83(m, 1H), 6.93(m, 2H), 7.50(m, 1H), 7.65(m, 1H), 7.77(s, 1H), 8.13(m, 1H), 8.28(m, 1H), 8.67(s, 1H)

EXAMPLE 79

N-(2-Furylmethyl)-6-[1-[3-(isopropylamino)-2-pyridyl]piperazin-4-yl-carbonyl]nicotinamide.HCl By the same procedure as described in the example 73, synthesis was carried out using Furfurylamine.

Yield: 61% m.p.: 173~176° C.

$^1$H-NMR(CDCl$_3$), ppm: δ1.33(d, 6H), 3.50(m, 4H), 3.64(m, 1H), 3.86(m, 2H), 4.02(m, 2H), 4.68(d, 2H), 6.34(s, 2H), 7.25(m, 2H), 7.38(s, 1H), 7.70(m, 2H), 7.81(m, 1H), 8.28(m, 1H), 8.99(s, 1H)

EXAMPLE 80

N-[2-(1H-imidazol4-yl)ethyl]-6-[1-[3-(isopropylamino)-2-pyridyl]piperazin-4-yl-carbonyl] nicotinamide By the same procedure as described in the example 76, synthesis was carried out using histamine.

Yield: 72% m.p.: 98~102° C.

$^1$H-NMR(CDCl$_3$), ppm: δ1.24(d, 6H), 2.96(m, 2H), 3.07(m, 2H), 3.15(m, 2H), 3.53(m, 1H), 3.67(m, 2H), 3.74(m, 2H), 3.95(m, 2H), 4.15(m, 1H), 6.83(m, 1H), 6.94(m, 2H), 7.67(m, 2H), 7.81(m, 1H), 8.28(m, 1H), 8.46(m, 1H), 9.08(s, 1H)

EXAMPLE 81

6-[1-[3-(isopropylamino)-2-pyridyl]piperazin-4-yl-carbonyl]-N-[2-(2-thienyl)ethyl]nicotinamide Triethylamine (0. 8 ml) was added to 6-[1-[3-(isopropylamino)-2-pyridyl]piperazin-4-yl-carbonyl] nicotinic acid (2g) in methylene chloride (30 ml) for dissolution and cooled. With the slow addition of pivaloyl chloride (0. 7 ml) at 0° C.~5° C., the mixture was stirred at 5° C for 1 hour. With the successive addition of triethylamine (0.9 ml) and 2-thiophenethylamine (0.75 g), the mixture was stirred at 5° C.~10° C. for 2 hours. The solution was washed with an aqueous sodium bicarbonate and water. The separated organic layer was dried over magnesium sulfate and concentrated under reduced pressure. The concentrated residue was treated with ether for crystallization. The solid, so obtained, was recrystallized with ethanol and hexane to give a desired compound of 1.92 g (yield: 74%).

m.p.: 131~134° C.

$^1$H-NMR(CDCl$_3$), ppm: δ1.22(d, 6H), 3.03(m, 2H), 3.16(m, 4H), 3.53(m, 1H), 3.64(m, 2H), 3.73(m, 2H), 3.91(m, 2H), 4.14(m, 1H), 6.87(m, 5H), 7.16(m, 1H), 7.55(m, 1H), 7.63(m, 1H), 8.08(m, 1H), 8.85(m, 1H)

EXAMPLE 82

6-[1-[3-(isopropylamino)-2-pyridyl]piperazin-4-yl-carbonyl]-N-[2-(2-pyridyl)ethyl]nicotinamide By the same procedure as described in the example 81, synthesis was carried out using 2-(2-aminoethyl)pyridine.

Yield: 68% m.p.: 79~82° C.

$^1$H-NMR(CDCl$_3$), ppm: δ1.22(d, 6H), 3.07(m, 6H), 3.52(m, 1H), 3.66(m, 2H), 3.84(m, 2H), 3.94(m, 2H), 4.14(m, 1H), 6.81(m, 1H), 6.88(m, 1H), 7.20(m, 2H), 7.65(m, 3H), 8.15(m, 1H), 8.21(m, 1H), 8.54(m, 1H), 8.96(m, 1H)

EXAMPLE 83

N-[3- (1H-imidazol-1-yl)propyl]-6-[1-[3-(isopropylamino)-2-pyridyl]piperazin-4-yl-carbonyl] nicotinamide By the same procedure as described in the example 81, synthesis was carried out using 1-(3-aminopropyl)

imidazole. And then, the product was crystallized with methylene chloride and ether to give a desired compound.

Yield: 71% m.p.: 105~108° C.

$^1$H-NMR(CDCl$_3$), ppm: δ1.23(d, 6H), 2.16(m, 2H), 3.05 (m, 2H), 3.16(m, 2H), 3.48(m, 2H), 3.54(m, 1H), 3.64(m, 2H), 3.94(m, 2H), 4.13(m, 2H), 6.82(m, 1H), 6.94(m, 1H), 7.06(m, 2H), 7.57(m, 1H), 7.65(m, 1H), 7.76(m, 1H), 7.89 (m, 1H), 8.18(m, 1H), 8.99(s, 1H)

EXAMPLE 84

N-[3-(1H-imidazol-1-yl)propyl]-6-[1-[3-(isobutylamino)-2-pyridyl]piperazin-4-yl-carbonyl]nicotinamide By the same procedure as described in the example 81, synthesis was carried out starting with 6-[1-[3-(isobutylamino)-2-pyridyl]piperazin-4-yl-carbonyl]nicotinic acid and using 1-(3-aminopropyl)imidazole. And then, the product was recrystallized with isopropanol to give a desired compound.

Yield: 66%

$^1$H-NMR(TFA-d$_1$), ppm: δ1.23(d, 6H), 2.17(m, 1H), 2.58 (m, 2H), 3.26(m, 2H), 1891 3.84(m, 6H), 4.18(m, 2H), 4.40(m, 2H), 4.60(m, 2H), 7.65(m, 4H), 7.78(m, 1H), 8.62 (m, 1H), 8.92(m, 1H), 9.39(m, 1H), 9.78(s, 1H)

EXAMPLE 85

N-(3-hydroxy-2-pyridyl)-6-[1-[3-(isopropylamino)-2-pyridyl]piperazin-4-yl-carbonyl]nicotinamide By the same procedure as described in the example 70, synthesis was carried out using 2-amino-3-hydroxypyridine.

Yield: 62% m.p.: 116~119° C.

$^1$H-NMR(DMSO-d$_6$) ppm: δ1.17(d, 6H), 2.94(m, 2H), 3.03(m, 2H), 3.55(m, 3H), 3.86(m, 2H), 4.45(m, 1H), 6.91 (m, 2H), 7.21(m, 1H), 7.34(m, 1H), 7.55(m, 1H), 7.73(m, 1H), 7.95(m, 1H), 8.43(m, 1H), 9.14(s, 1H), 9.87(s, 1H), 10.73(s, 1H)

EXAMPLE 86

N-(3-hydroxy-2-pyridyl)-6-[-3-(isobutylamino)-2-pyridyl]piperazin-4-yl-carbonyl]nicotinamide By the same procedure as described in the example 70, synthesis was carried out starting with 6-[1-[3-(isobutylamino)-2-pyridyl]piperazin-4-yl-carbonyl]nicotinic acid and using 1-(3-aminopropyl)imidazole.

Yield: 60% m.p.: 165~167° C.

$^1$H-NMR(TFA-d$_1$), ppm: δ1.85(d, 6H), 2.14(m, 1H), 3.23 (d, 2H), 3.74(m, 4H), 4.12(m, 2H), 4.39(m, 2H), 7.72(m, 4H), 8.25(m, 2H), 8.61(m, 1H), 9.49(m, 1H), 9.87(s, 1H)

EXAMPLE 87

6-[1-(2-hydroxyethyl)piperazin-4-yl-carbonyl]-N-isopropylnicotinamide.HCl

6-[1-(2-hydroxyethyl)piperazin-4yl-carbonyl]nicotinic acid methyl ester (3 g) was dissolved in methanol (40 ml) and with the addition of isopropylamine (6 ml), the mixture was heated to reflux for 12 hours. The mixture was concentrated under reduced pressure to remove the solvent and the excess of isopropylamine. The concentrated residue was chromatographed on column (hexane/chloroform/methanol=7/5/1). The purified solution was recovered and concentrated under reduced pressure, and was dissolved in chloroform. To this solution, 2N-hydrochloride solution in isopropanol (4.3 ml) was added, and ether was added gradually for precipitation. After a 1-hour stirring, the precipitate was filtered and washed (ether) to give a desired compound of 2.74 g (yield: 75%) as hydrochloride salt.

$^1$H-NMR(TFA-d$_1$), ppm: δ1.52(d, 6H), 3.81(m, 4H), 4.10 (m, 1H), 4.22(m, 2H), 4.46(m, 4H), 4.58(m, 1H), 5.22(m, 1H), 8.65(d, 1H), 9.41(d, 1H), 9.80(s, 1H)

EXAMPLE 88

6-[1-(2-hydroxyethyl)piperazin-4-yl-carbonyl]-N-isobutylnicotinamide.HCl

By the same procedure as described in the example 87, the synthesis was carried out using isobutylamine.

Yield: 70%

$^1$H-NMR(TFA-d$_1$), ppm: δ1.20(d, 6H), 2.18(m, 1H), 3.60 (m, 2H), 3.80(m, 4H), 4.01(m, 1H), 4.21(m, 2H), 4.45(m, 4H), 5.15(m, 1H), 8.64(d, 1H), 9.41(d, 1H), 9.79(s, 1H)

EXAMPLE 89

N-ethyl-6-[1-(2-hydroxyethyl)piperazin-4-yl-carbonyl]nicotinamide.HCl

6-[1-(2-hydroxyethyl)piperazin-4-yl-carbonyl]nicotinic acid methyl ester (3 g) was dissolved in ethanol (25 ml) and with the addition of 70% ethylamine solution (8 ml), the mixture was heated to reflux for 6 hours. The mixture was concentrated under reduced pressure to remove the solvent and the excess of ethylamine, dissolved in chloroform and dried over magnesium sulfate. The residue was chromatographed on column (hexane/chloroform/methanol=10/5/2). The purified solution was recovered and concentrated under reduced pressure, and was dissolved in isopropanol. To this solution, 2N-hydrochloride solution in isopropanol (4.3 ml) was added, and ether was added gradually for precipitation. The precipitate was filtered and isolated to give a desired compound of 2.38 g (yield: 68%) as hydrochloride salt.

$^1$H-NMR(CDCl$_3$), ppm: δ1.28(t, 3H), 2.56(m, 2H), 2.64 (m, 4H), 3.50(m, 2H), 3.57(m, 2H), 3.67(m, 2H), 3.85(m, 2H), 6.57(m, 1H), 7.63(d, 2H), 8.14(m, 1H), 8.92(s, 1H)

EXAMPLE 90

6-[1-(2-hydroxyethyl)piperazin-4-yl-carbonyl]-N-propylnicotinamide.HCl

By the same procedure as described in the example 87, the synthesis was carried out using propylamine.

Yield: 65%

$^1$H-NMR(CDCl$_3$), ppm: δ0.98(t, 3H), 1.92(m, 2H), 2.51 (m, 2H), 2.65(m, 4H), 3.51(m, 5H), 3.68(m, 2H), 3.83(m, 2H), 6.58(m, 1H), 7.64(d, 2H), 8.14(m, 1H), 8.93(m, 1H)

EXAMPLE 91

N-cyclopropyl-6-[1-(2-hydroxyethyl)piperazin-4-yl-carbonyl]nicotinamide.HCl

By the same procedure as described in the example 87, the synthesis was carried out using cyclopropylamine.

Yield: 69%

¹H-NMR(TFA-d₁), ppm: δ0.71(m, 2H), 0.87(m, 2H), 2.91(m, 1H), 3.72(m, 4H), 4.12(m, 3H), 4.46(m, 4H), 4.59 (m, 1H), 8.65(d, 1H), 9.42(d, 1H), 9.81(s, 1H),

EXAMPLE 92

N-cyclopropylmethyl-6-[1-(2-hydroxyethyl) piperazin-4-yl-carbonyl]nicotinamide. HCl By the same procedure as described in the example 87, the synthesis was carried out using (aminomethyl) cyclopropane.

Yield: 76%

¹H-NMR(TFA-d₁), ppm: δ0.31(m, 1H), 0.72(m, 2H), 0.87(m, 2H), 3.61(m, 2H), 3.81(m, 4H), 4.01(m, 1H), 4.21 (m, 2H), 4.45(m, 4H), 5.15(m, 1H), 8.64(d, 1H), 9.41(d, 1H), 9.79(s, 1H)

EXAMPLE 93

N-(2-hydroxyethyl)-6-[1-(2-hydroxyethyl)piperazin-4-yl-carbonyl]nicotinamide

6-[1-(2-hydroxyethyl)piperazin-4-yl-carbonyl]nicotinic acid methyl ester (2 g) was dissolved in methanol (20 ml) and with the addition of ethanolamine (2 ml), the mixture was heated to reflux for 8 hours and concentrated under reduced pressure. The concentrated residue was dissolved in isopropanol (14 ml), and with the addition of isopropyl ether to precipitate. After 2-hours stirring, the filtered solid was recrystallized with ethyl acetate and hexane to give a desired compound of 1.74 g (yield: 79%).

m.p.: 126~128° C.

¹H-NMR(TFA-d₁), ppm: δ3.71(m, 4H), 4.01(m, 3H), 4.23(m, 5H), 4.41(m, 3H), 5.13(m, 1H), 8.57(d, 1H), 9.38 (m, 1H), 9.78(s, 1H)

EXAMPLE 94

6-[1-(2-hydroxyethyl)piperazin-4-yl-carbonyl]-N-[(1R)-1-(hydroxymethyl)propyl]nicotinamide.HCl 6-[1-(2-hydroxyethyl)piperazin-4-yl-carbonyl]nicotinic acid methyl ester (3 g) was dissolved in ethanol (30 ml) and with the addition of (R)-(−)-2-amino-1-butanol (4 ml), the mixture was heated to reflux for 10 hours and concentrated under reduced pressure. The residue was chromatographed on column (hexane/ethyl acetate/ethanol=5/3/1). The purified solution was recovered and concentrated under reduced pressure, and was dissolved in methylene chloride. To this solution, 2N-hydrochloride solution in isopropanol (4.2ml) was added, and ether was added gradually for precipitation. After 2-hours stirring, the mixture was filtered to give a desired compound of 2.85 g (yield: 72%) as a hydrochloride salt.

¹H-NMR(TFA-d₁), ppm: δ1.21(t, 3H), 1.91(m, 2H), 3.77 (m, 4H), 4.01(m, 1H), 4.25(m, 4H), 4.43(m, 3H), 4.53(m, 1H), 5.18(m, 1H), 8.62(d, 1H), 9.42(d, 1H), 9.81(s, 1H)

EXAMPLE 95

6-[1-(2-hydroxyethyl)piperazin-4-yl-carbonyl]-N-[(1S)-1-(hydroxymethyl)propyl]nicotinamide.HCl By the same procedure as described in the example 94, the synthesis was carried out using (S)-(+)-2-amino-1-butanol.

Yield: 67%

¹H-NMR(TFA-d₁), ppm: δ1.22(t, 3H), 1.92(m, 2H), 3.77 (m, 4H), 3.99(m, 1H), 4.23(m, 4H), 4.43(m, 1H), 4.53(m, 1H), 5.16(m, 1H), 8.63(d, 1H), 9.43(d, 1H), 9.81(s, 1H)

EXAMPLE 96

6-[1-(2-hydroxyethyl)piperazin-4-yl-carbonyl]-N-[1-(hydroxymethyl)propyl]nicotinamide.HCl By the same procedure as described in the example 94, the synthesis was carried out using DL-2-amino-1-butanol.

Yield: 69%

¹H-NMR(TFA-d₁), ppm: δ1.21(t, 3H), 1.93(m, 2H), 3.78 (m, 4H), 4.01(m, 1H), 4.22(m, 4H), 4.43(m, 1H), 4.53(m, 1H), 5.15(m, 1H), 8.63(d, 1H), 9.43(d, 1H), 9.80(s, 1H)

EXAMPLE 97

N-[2-hydroxy-1-(hydroxymethyl)ethyl]-6-[1-(2-hydroxyethyl)piperazin-4-yl-carbonyl]nicotinamide.HCl By the same procedure as described in the example 94, synthesis was carried out using 2-amino-1,3-propandiol.

Yield: 64%

¹H-NMR(TFA-d₁), ppm: δ3.67(m, 4H), 4.11 4.25(m, 8H), 4.43(m, 3H), 4.53(m, 1H), 5.22(m, 1H), 8.63(d, 1H), 9.43(d, 1H), 9.81(s, 1H)

EXAMPLE 98

6-[1-(2-hydroxyethyl)piperazin-4-yl-carbonyl]-N-(2-methoxyethyl)nicotinamide.HCl 6-[1-(2-hydroxyethyl)piperazin-4-yl-carbonyl]nicotinic acid methyl ester (3 g) was dissolved in methanol (18 ml) and with the addition of 2-methoxyethylamine (4 ml), the mixture was heated to reflux for 12 hours and concentrated under reduced pressure. The residue was chromatographed on column (hexane/methylene chloride/methanol=7/4/1). The purified solution was recovered and concentrated under reduced pressure, and was dissolved in isopropanol. To this solution, 2N-hydrochloride solution in isopropanol (4.4 ml) was added, and ether (20 ml) was added, and the mixture was stirred for 1 hour. The mixture was filtered, washed (ether) and dried to give a desired compound of 3.05 g (yield: 80%) as hydrochloride salt.

m.p.: 150~152° C.

¹H-NMR(CDCl₃), ppm: δ2.84–2.92(m, 7H), 3.13–3.30 (m, 7H), 3.48(m, 1H), 3.57(m, 2H), 3.87(m, 1H), 4.31(m, 1H), 7.33(d, 1H), 7.95(m, 1H), 8.16(s, 1H), 8.64(s, 1H)

EXAMPLE 99

6-[1-(2-hydroxyethyl)piperazin-4-yl-carbonyl]-N-(3-methoxypropyl)nicotinamide

By the same procedure as described in the example 93, synthesis was carried out using 3-methoxypropylamine.

Yield: 73% m.p.: 88~90° C.

¹H-NMR(CDCl₃), ppm: δ1.87(m, 2H), 2.63(m, 6H), 3.38 (s, 3H), 3.56(m, 6H), 3.66(m, 2H), 3.86(m, 2H), 7.23(m, 1H), 7.68(d, 2H), 8.15(m, 1H), 8.89(d, 1H),

EXAMPLE 100

N,N-bis(2-methoxyethyl)-6-[1-(2-hydroxyethyl) piperazin-4-yl-carbonyl]nicotinamide.HCl By the same procedure as described in the example 94, synthesis was carried out using bis(2-methoxyethyl)amine.

Yield: 58%

¹H-NMR(TFA-d₁), ppm: δ3.68(m, 3H), 3.76(m, 2H), 3.84(s, 6H), 3.94(m, 4H), 4.06(m, 1H), 4.15(m, 1H), 4.17(m, 6H), 4.41(m, 1H), 4.47(m, 2H), 5.19(m, 1H), 8.55(d, 1H), 9.08(d, 1H), 9.51(s, 1H)

EXAMPLE 101

N-(2,2-dimethoxyethyl)-6-[1-(2-hydroxyethyl)piperazin-4-yl-carbonyl]nicotinamide By the same procedure as described in the example 93, synthesis was carried out using 2,2-dimethoxyethylamine.

Yield: 65% m.p.: 107~109° C.

¹H-NMR(TFA-d₁), ppm: δ3.78(m, 2H), 4.15(m, 3H), 4.23–4.45(m, 13H), 4.90(d, 1H), 5.09(m, 2H), 5.21(m, 1H), 8.67(d, 1H), 9.45(d, 1H), 9.87(s, 1H)

EXAMPLE 102

6-[1-(2-hydroxyethyl)piperazin-4-yl-carbonyl]-N-[2-(morpholin-4-yl)-ethyl]nicotinamide.HCl By the same procedure as described in the example 94, synthesis was carried out using 4-(2-aminoethyl)morpholine.

Yield: 70%

¹H-NMR(TFA-d₁), ppm: 6 3.86(m, 4H), 4.01(m, 5H), 4.10(m, 1H), 4.22(m, 2H), 4.34~4.43(m, 7H), 4.54(m, 5H), 5.19(m, 1H), 8.60(d, 1H), 9.06(d, 1H), 9.51 (s, 1H)

EXAMPLE 103

N-(2-Furylmethyl)-6-[1-(2-hydroxyethyl)piperazin-4-yl-carbonyl]nicotinamide.HCl

By the same procedure as described in the example 94, synthesis was carried out using furfurylamine.

Yield: 64%

¹H-NMR(TFA-d₁), ppm: δ3.69(m, 2H), 3.87(m, 4H), 4.23(m, 2H), 4.37(m, 4H), 4.54(m, 2H), 5.21(m, 1H), 7.78 (m, 2H), 8.60(d, 1H), 9.01(d, 1H), 9.36(d, 1H), 9.51(s, 1H)

Experiment 1: Inhibitory Activities Against HBV Polymerase in vitro

Recently, the inventors of the present invention have produced a recombinant HBV polymerase that is expressed from *E.coli* transformant, measured its enzyme activity and filed patent applications threrof [Korean Pat. Appl. Nos. 94-3918 and 96-33998].

The inventors have also established a method of measuring the reverse transcriptase activity of HBV polymerase in vitro. The fundamental principle is the same as the ELISA method, and after reacting the substrate with biotin- and DIG-modified nucleotide, a method of recognizing the polymerized substrate as anti-DIG antibody with peroxidase was used.

20 μl of HBV polymerase, 20 μl of reaction mixture and 20 μl of test compound was mixed and reacted at 14° C.~30° C. for 18~24 hours. Then, the inhibitory effect of the test compound against reverse transcriptase activity in the HBV polymerase was examined, compared with the results of control tests without the test compound.

The inhibitory activities of each test compound were shown in the following tables 1a~1g and table 2.

TABLE 1a

The inhibitory effects of reverse transcriptase (RT) enzyme activity of HBV.

(1a)

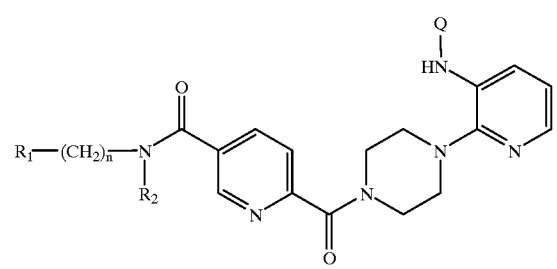

| | | | | | Inhibitory activity of HBV-RT (%) | | |
|---|---|---|---|---|---|---|---|
| Example | $R_1$ | $R_2$ | Q | n | 1 μg/ml | 0.1 μg/ml | 0.01 μg/ml |
| Exam. 1 | HO— | H | i-Pr | 2 | 54 | 51 | 30 |
| Exam. 2 | HO— | H | i-Pr | 3 | 71 | 60 | 49 |
| Exam. 3 | (R)- 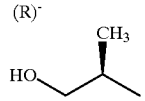 | H | i-Pr | 0 | 74 | 57 | 41 |

TABLE 1a-continued

The inhibitory effects of reverse transcriptase (RT) enzyme activity of HBV.

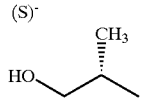

(1a)

| | | | | | Inhibitory activity of HBV-RT (%) | | |
|---|---|---|---|---|---|---|---|
| Example | R₁ | R₂ | Q | n | 1 μg/ml | 0.1 μg/ml | 0.01 μg/ml |
| Exam. 4 | (S)- 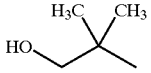 | H | i-Pr | 0 | 56 | 39 | 30 |
| Exam. 6 | 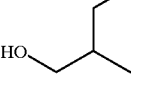 | H | i-Pr | 0 | 80 | 65 | 62 |
| Exam. 7 | (R)- 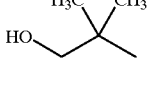 | H | i-Pr | 0 | 70 | 64 | 53 |
| Exam. 13 | (R)- 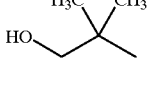 | H | i-Pr | 0 | 72 | 56 | 51 |
| Exam. 14 | HO— | CH₃CH₂— | i-Pr | 2 | 35 | 10 | — |
| Exam. 16 | HO— | HOCH₂CH₂— | i-Pr | 2 | 70 | 60 | 51 |

TABLE 1b

| | | | | | Inhibitory activity Of HBV-RT (%) | | |
|---|---|---|---|---|---|---|---|
| Example | R₁ | R₂ | Q | N | 1 μg/ml | 0.1 μg/ml | 0.01 μg/ml |
| Exam. 17 | HO— | Ph— | i-Pr | 2 | 66 | 53 | 42 |
| Exam. 18 | HO— | H | Et | 2 | 84 | 69 | 52 |
| Exam. 19 | 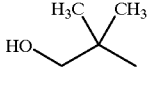 | H | Et | 0 | 72 | 56 | 32 |
| Exam. 20 | HO— | H | H | 2 | 74 | 67 | 54 |
| Exam. 21 | H₃C CH₃ HO | H | H | 0 | 70 | 62 | 38 |
| Exam. 22 | HO— | H | i-Bu | 0 | 86 | 60 | 54 |

TABLE 1b-continued

| Example | R₁ | R₂ | Q | N | Inhibitory activity Of HBV-RT (%) 1 μg/ml | 0.1 μg/ml | 0.01 μg/ml |
|---|---|---|---|---|---|---|---|
| Exam. 23 | 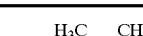 | H | i-Bu | 0 | 90 | 71 | 63 |
| Exam. 24 | (CH₃)₂CH— | H | i-Pr | 0 | 65 | 51 | 23 |
| Exam. 25 | (CH₃)₂CH— | H | Et | 0 | 85 | 67 | 54 |
| Exam. 26 | (CH₃)₂CH— | H | i-Bu | 0 | 90 | 66 | 58 |
| Exam. 27 | (CH₃)₂CH— | H | H | 0 | 79 | 62 | 43 |
| Exam. 28 | (CH₃)₃C— | H | i-Pr | 0 | 88 | 72 | 61 |
| Exam. 30 | (CH₃)₂CH— | H | i-Pr | 1 | 83 | 65 | 61 |
| Exam. 33 | CH₃— | CH₃CH₂— | i-Pr | 1 | 73 | 62 | 20 |

TABLE 1c

| Example | R₁ | R₂ | Q | N | Inhibitory activity of HBV-RT (%) 1 μg/ml | 0.1 μg/ml | 0.01 μg/ml |
|---|---|---|---|---|---|---|---|
| Exam. 35 | cyclopropyl | H | i-Pr | 0 | 62 | 51 | 5 |
| Exam. 36 | cyclopropyl | H | i-Bu | 0 | 87 | 71 | 60 |
| Exam. 37 | cyclopentyl | H | i-Pr | 0 | 75 | 65 | 39 |
| Exam. 39 | CH₃O— | H | i-Pr | 2 | 80 | 68 | 60 |
| Exam. 40 | CH₃O— | H | Et | 2 | 75 | 57 | 36 |
| Exam. 41 | CH₃O— | H | i-Bu | 2 | 85 | 70 | 52 |
| Exam. 42 | CH₃O— | CH₃O—(CH₂)₂— | i-Pr | 2 | 70 | 52 | 15 |
| Exam. 43 | CH₃OCH₂CH(CH₃)— | H | i-Pr | 0 | 68 | 61 | 50 |
| Exam. 45 | CH₃O— | H | i-Pr | 3 | 63 | 53 | 28 |
| Exam. 47 | CH₃O— | H | i-Bu | 3 | 72 | 51 | 20 |
| Exam. 48 | HO—(CH₂)₂O— | H | i-Pr | 2 | 79 | 66 | 52 |
| Exam. 50 | (CH₃O)₂CH— | CH₃ | i-Pr | 1 | 60 | 51 | 15 |
| Exam. 51 | (CH₃O)₂CH— | H | i-Pr | 1 | 87 | 65 | 57 |
| Exam. 52 | 1,3-dioxolan-2-yl | CH₃ | i-Pr | 1 | 76 | 60 | 39 |

TABLE 1d

| Example | R₁ | R₂ | Q | N | Inhibitory activity of HBV-RT (%) 1 μg/ml | 0.1 μg/ml | 0.01 μg/ml |
|---|---|---|---|---|---|---|---|
| Exam. 53 |  | H | i-Pr | 1 | 74 | 60 | 52 |

TABLE 1d-continued
| | | | | | Inhibitory activity of HBV-RT (%) | | |
|---|---|---|---|---|---|---|---|
| Example | R₁ | R₂ | Q | N | 1 μg/ml | 0.1 μg/ml | 0.01 μg/ml |
| Exam. 55 | 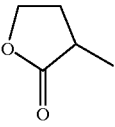 | H | i-Pr | 0 | 79 | 69 | 55 |
| Exam. 56 | 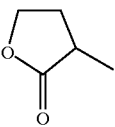 | H | H | 0 | 82 | 70 | 65 |
| Exam. 57 | 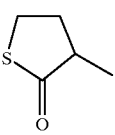 | H | i-Pr | 0 | 72 | 53 | 23 |
| Exam. 58 | 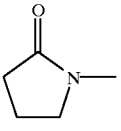 | H | i-Pr | 3 | 84 | 72 | 63 |
| Exam. 59 | 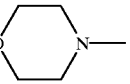 | H | i-Pr | 2 | 70 | 60 | 49 |
| Exam. 60 | 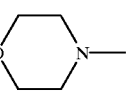 | H | Et | 2 | 66 | 52 | 30 |
| Exam. 62 | (CH₃)₂N— | H | i-Pr | 2 | 69 | 58 | 47 |
| Exam. 66 | 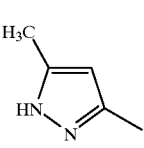 | H | i-Pr | 0 | 70 | 53 | 20 |
TABLE 1e
| | | | | | Inhibitory activity of HBV-RT (%) | | |
|---|---|---|---|---|---|---|---|
| Example | R₁ | R₂ | Q | N | 1 μg/ml | 0.1 μg/ml | 0.01 μg/ml |
| Exam. 67 | 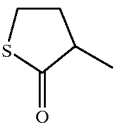 | H | i-Pr | 0 | 72 | 50 | 25 |

TABLE 1e-continued

| | | | | | Inhibitory activity of HBV-RT (%) | | |
|---|---|---|---|---|---|---|---|
| Example | R₁ | R₂ | Q | N | 1 µg/ml | 0.1 µg/ml | 0.01 µg/ml |
| Exam. 68 | 4-methyl-2-thiazolyl (H₃C-thiazole) | H | i-Pr | 0 | 81 | 69 | 30 |
| Exam. 69 | 2-methyl-1,3,4-thiadiazolyl | H | i-Pr | 0 | 64 | 47 | 12 |
| Exam. 70 | 2-pyridyl | H | i-Pr | 0 | 74 | 55 | 26 |
| Exam. 71 | 6-methoxy-3-pyridyl (CH₃O-pyridyl) | H | i-Pr | 0 | 83 | 70 | 59 |
| Exam. 72 | 2-pyrazinyl | H | i-Pr | 0 | 64 | 53 | 16 |
| Exam. 73 | 2-pyridyl | H | i-Pr | 1 | 77 | 62 | 53 |
| Exam. 74 | 2-pyridyl | H | Et | 1 | 70 | 56 | 19 |

TABLE 1f

| | | | | | Inhibitory activity of HBV-RT (%) | | |
|---|---|---|---|---|---|---|---|
| Example | R₁ | R₂ | Q | N | 1 µg/ml | 0.1 µg/ml | 0.01 µg/ml |
| Exam. 75 | 2-pyridyl | H | H | 1 | 72 | 55 54 | 22 |
| Exam. 76 | 3-pyridyl | H | i-Pr | 1 | 62 | 53 | 30 |

TABLE 1f-continued
| Example | R₁ | R₂ | Q | N | Inhibitory activity of HBV-RT (%) | | |
|---|---|---|---|---|---|---|---|
| | | | | | 1 µg/ml | 0.1 µg/ml | 0.01 µg/ml |
| Exam. 77 | 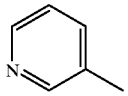 | H | i-Pr | 1 | 79 | 65 | 39 |
| Exam. 78 | 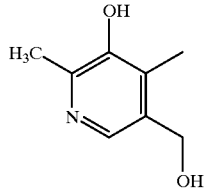 | H | i-Pr | 1 | 62 | 58 | 15 |
| Exam. 79 | 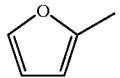 | H | i-Pr | 1 | 78 | 63 | 54 |
| Exam. 80 | 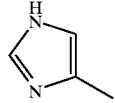 | H | i-Pr | 2 | 70 | 61 | 52 |
| Exam. 81 | 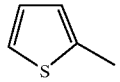 | H | i-Pr | 2 | 80 | 60 | 44 |
TABLE 1g
| Example | R₁ | R₂ | Q | N | Inhibitory activity of BV-RT (%) | | |
|---|---|---|---|---|---|---|---|
| | | | | | 1 µg/ml | 0.1 µg/ml | 0.01 µg/ml |
| Exam. 82 | 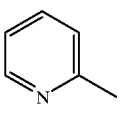 | H | i-Pr | 2 | 67 | 53 | 24 |
| Exam. 83 | 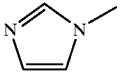 | H | i-Pr | 3 | 89 | 72 | 65 |
| Exam. 84 | 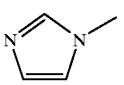 | H | i-Bu | 3 | 88 | 72 | 60 |
| Exam. 85 | 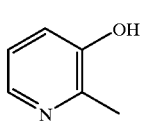 | H | i-Pr | 0 | 88 | 70 | 61 |
| Exam. 86 | 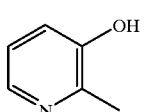 | H | i-Bu | 0 | 71 | 46 | 13 |

TABLE 2

(1b)

Structure: R₁—(CH₂)ₙ—N(R₂)—C(=O)—[pyridine]—C(=O)—N[piperazine]N—CH₂CH₂—OH

| Example | R₁ | R₂ | n | Inhibitory activity of HBV-RT (%) 1 μg/ml | 0.1 μg/ml | 0.01 μg/ml |
|---|---|---|---|---|---|---|
| Exam. 87 | (CH$_3$)$_2$CH— | H | 0 | 75 | 58 | 52 |
| Exam. 88 | (CH$_3$)$_2$CH— | H | 1 | 81 | 67 | 55 |
| Exam. 89 | CH$_3$— | H | 1 | 68 | 50 | 35 |
| Exam. 93 | HO— | H | 2 | 73 | 59 | 30 |
| Exam. 94 | (R)- HO-CH$_2$-CH(CH$_3$)- | H | 0 | 72 | 51 | 20 |
| Exam. 98 | CH$_3$O— | H | 2 | 85 | 70 | 57 |
| Exam. 99 | CH$_3$O— | H | 3 | 68 | 60 | 15 |
| Exam. 100 | CH$_3$O— | CH$_3$OCH$_2$CH$_2$— | 2 | 77 | 49 | 20 |
| Exam. 101 | (CH$_3$O)$_2$CH— | H | 1 | 85 | 63 | 55 |
| Exam. 102 | morpholinyl | H | 2 | 70 | 56 | 32 |
| Exam. 103 | 2-furyl | H | 1 | 72 | 54 | 20 |

Experiment 2: The in vitro Inhibition Test Against HIV Reverse Transcriptase

The inhibitory activity in vitro was measured using a non-radioactive reverse transcriptase assay Kit (Boehringer Mannheim).

At first, 20 μl(40 ng) of HIV-RT was added to the wells, coated with streptavidin and with the addition of 20 μl reaction mixture containing template/primer hybrid poly(A)/oligo(dT)$_{15}$ and DIG-(digoxigenin)-dUTP, biotin-dUTP and TTP, 20 μl of test compound was added and reacted at 37° C. for 1 hour. The control without test compound was used for the comparison of related activity. Since DNA containing nucleotide labeled with digoxigenin and biotine was prepared by the action of HIV-RT, it was combined with streptavidin coated at the bottom of the wells. After the reaction was completed, remaining impurities were removed by washing each well with 250 μl buffer solution (pH 7.0) for 30 seconds 5 times and with the addition of 200 μl anti-DIG-POD antibody, the mixture was reacted at 37° C. for 1 hour. For the removal of remaining impurities again, the reacting solution was washed with a buffer solution and with the addition of 200 μl ABTS™ each, a substrate of POD(peroxidase), the solution was reacted at room temperature for 30 minutes. The absorbance was read by ELISA reader at 405 nm for the assay of reverse transcriptase activity and its inhibition activity.

The results of inhibitory activities for each sample were shown in the following tables 3a~3f and table 4.

TABLE 3a (1a)

[Structure: R₁—(CH₂)ₙ—N(R₂)—C(=O)—pyridine—C(=O)—N-piperazine-N—pyridine—NH—Q]

| Example | R₁ | R₂ | Q | N | Inhibitory activity of HIV-RT (%) 1 μg/ml | 0.1 μg/ml |
|---|---|---|---|---|---|---|
| Exam. 6 | HOCH₂C(CH₃)₂— | H | i-Pr | 0 | 70 | 48 |
| Exam. 13 | (R)- HOCH₂CH(CH₃)— with CH₂OH | H | i-Pr | 0 | 80 | 61 |
| Exam. 16 | HO— | HOCH₂CH₂ | i-Pr | 2 | 68 | 47 |
| Exam. 22 | HO— | H | i-Bu | 2 | 60 | 50 |
| Exam. 23 | HOCH₂C(CH₃)₂— | H | i-Bu | 0 | 62 | 46 |
| Exam. 24 | (CH₃)₂CH— | H | i-Pr | 0 | 66 | 30 |
| Exam. 25 | (CH₃)₂CH— | H | Et | 0 | 75 | 52 |
| Exam. 26 | (CH₃)₂CH— | H | i-Bu | 0 | 60 | 45 |
| Exam. 27 | (CH₃)₂CH— | H | H | 0 | 70 | 54 |
| Exam. 28 | (CH₃)₃C— | H | i-Pr | 0 | 55 | 45 |

TABLE 3b

| Example | R₁ | R₂ | Q | N | Inhibitory activity of HIV-RT (%) 1 μg/ml | 0.1 μg/ml |
|---|---|---|---|---|---|---|
| Exam. 30 | (CH₃)₂CH— | H | i-Pr | 1 | 58 | 32 |
| Exam. 33 | CH₃— | CH₃CH₂— | i-Pr | 1 | 80 | 64 |
| Exam. 35 | cyclopropyl | H | i-Pr | 0 | 68 | 30 |
| Exam. 36 | cyclopropyl | H | i-Bu | 0 | 73 | 60 |
| Exam. 37 | cyclopentyl | H | i-Pr | 0 | 51 | 25 |
| Exam. 39 | CH₃O— | H | i-Pr | 2 | 72 | 65 |

TABLE 3b-continued

| Example | R₁ | R₂ | Q | N | Inhibitory activity of HIV-RT (%) 1 μg/ml | 0.1 μg/ml |
|---|---|---|---|---|---|---|
| Exam. 40 | CH₃O— | H | Et | 2 | 70 | 52 |
| Exam. 41 | CH₃O— | H | i-Bu | 2 | 55 | 34 |
| Exam. 42 | CH₃O— | CH₃O—(CH₂)₂— | i-Pr | 2 | 54 | 20 |
| Exam. 43 | CH₃OCH₂CH(CH₃)— | H | i-Pr | 0 | 56 | 44 |
| Exam. 45 | CH₃O— | H | i-Pr | 3 | 68 | 47 |
| Exam. 47 | CH₃O— | H | i-Bu | 3 | 69 | 53 |
| Exam. 48 | HO—(CH₂)₂O— | H | i-Pr | 2 | 52 | 41 |
| Exam. 50 | (CH₃O)₂CH— | CH₃ | i-Pr | 1 | 55 | 40 |

TABLE 3c

| Example | R₁ | R₂ | Q | N | Inhibitory activity of HIV-RT(%) 1 μg/ml | 0.1 μg/ml |
|---|---|---|---|---|---|---|
| Exam. 51 | (CH₃O)₂CH— | H | i-Pr | 1 | 51 | 30 |
| Exam. 52 | 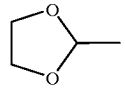 | CH₃ | i-Pr | 1 | 62 | 50 |
| Exam. 53 | 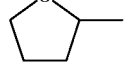 | H | i-Pr | 1 | 78 | 59 |
| Exam. 55 | 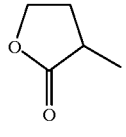 | H | i-Pr | 0 | 62 | 31 |
| Exam. 56 | 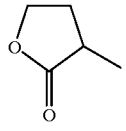 | H | H | 0 | 74 | 45 |
| Exam 57 | 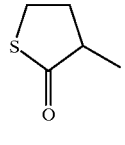 | H | i-Pr | 0 | 70 | 61 |
| Exam. 58 | 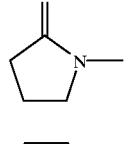 | H | i-Pr | 3 | 63 | 45 |
| Exam. 59 | 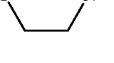 | H | i-Pr | 2 | 61 | 15 |
| Exam. 60 | 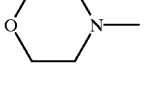 | H | Et | 2 | 73 | 55 |
| Exam. 62 | (CH₃)₂N— | H | i-Pr | 2 | 79 | 63 |

TABLE 3d

| Example | R₁ | R₂ | Q | N | Inhibitory activity of HIV-RT(%) 1 μg/ml | 0.1 μg/ml |
|---|---|---|---|---|---|---|
| Exam. 66 | 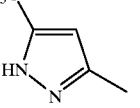 | H | i-Pr | 0 | 76 | 52 |
| Exam. 67 | 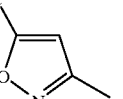 | H | i-Pr | 0 | 58 | 30 |
| Exam. 68 | 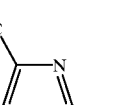 | H | i-Pr | 0 | 70 | 53 |
| Exam. 69 | 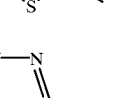 | H | i-Pr | 0 | 67 | 35 |
| Exam. 70 | 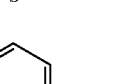 | H | i-Pr | 0 | 74 | 55 |
| Exam. 71 | 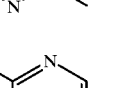 | H | i-Pr | 0 | 74 | 48 |
| Exam. 72 | 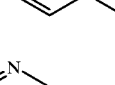 | H | i-Pr | 0 | 83 | 66 |
| Exam. 73 | 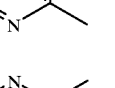 | H | i-Pr | 1 | 73 | 57 |

TABLE 3e

| Example | R₁ | R₂ | Q | N | 1 μg/ml | 0.1 μg/ml |
|---|---|---|---|---|---|---|
| Exam. 74 | 2-methylpyridine | H | Et | 1 | 80 | 61 |
| Exam. 75 | 2-methylpyridine | H | H | 1 | 72 | 53 |
| Exam. 76 | 3-methylpyridine | H | i-Pr | 1 | 82 | 57 |
| Exam. 77 | 4-methylpyridine | H | i-Pr | 1 | 79 | 59 |
| Exam. 78 | 3-hydroxy-2-methyl-5-(hydroxymethyl)-4-methylpyridine | H | i-Pr | 1 | 70 | 52 |
| Exam. 79 | 2-methylfuran | H | i-Pr | 1 | 54 | 20 |
| Exam. 80 | 4-methylimidazole | H | i-Pr | 2 | 48 | 21 |

Inhibitory activity of HIV-RT(%)

TABLE 3f

| Example | R₁ | R₂ | R₃ | N | 1 μg/ml | 0.1 μg/ml |
|---|---|---|---|---|---|---|
| Exam. 81 | 2-methylthiophene | H | i-Pr | 2 | 75 | 54 |
| Exam. 82 | 2-methylpyridine | H | i-Pr | 2 | 80 | 65 |
| Exam. 83 | 1-methylimidazole-CH₂- | H | i-Pr | 3 | 62 | 30 |
| Exam. 84 | 1-methylimidazole | H | i-Bu | 3 | 62 | 50 |
| Exam. 85 | 3-hydroxy-2-methylpyridine | H | i-Pr | 0 | 70 | 47 |

HIV-RT inhibitory activity(%)

TABLE 4

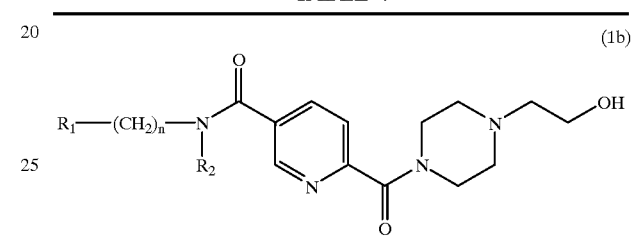

(1b)

| Example | R₁ | R₂ | N | 1 μg/ml | 0.1 μg/ml |
|---|---|---|---|---|---|
| Exam. 87 | (CH₃)₂CH— | H | 0 | 81 | 60 |
| Exam. 88 | (CH₃)₂CH— | H | 1 | 70 | 50 |
| Exam. 89 | CH₃— | H | 1 | 62 | 35 |
| Exam. 93 | HO— | H | 2 | 50 | 25 |
| Exam. 94 | (R)-HOCH₂CH(CH₃)— | H | 0 | 62 | 30 |
| Exam. 98 | CH₃O— | H | 2 | 76 | 61 |
| Exam. 99 | CH₃O— | H | 3 | 75 | 65 |
| Exam. 100 | CH₃O— | CH₃OCH₂CH₂— | 2 | 64 | 40 |
| Exam. 101 | (CH₃)₂CH— | H | 1 | 56 | 41 |
| Exam. 102 | morpholinyl— | H | 2 | 40 | 25 |
| Exam. 103 | 2-furyl | H | 1 | 80 | 65 |

Inhibitory activity of HIV-RT(%)

Experiment 3: Cytotoxicity Test

The cytotoxicity test was carried out using HepG2 cell in vitro. As a result, 2,5-pyridinedicarboxylic acid derivatives and its pharmaceutically acceptable salts proven not to have cytotoxicity with $CC_{50} \geq 200$ μM, thus being quite effective in terms of safety.

As discussed in the above, the compounds of the formula 1 according to the present invention, and its pharmaceutically acceptable salts are effective as active ingredients of inhibiting the proliferation of virus including HBV and HIV in that without any cytotoxicty.

What is claimed is:

1. A 2,5-pyridinedicarboxylic acid derivative, and pharmaceutically acceptable salts thereof, of the formula 1

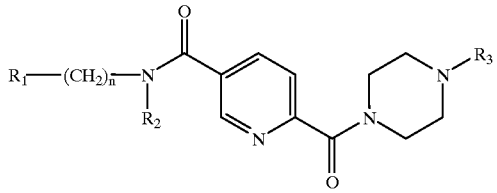

(1)

wherein $R_1$ is selected from the group consisting of:
  a hydroxy group,
  a straight or branched alkyl group of 1 to 6 carbon atoms,
  a cycloalkyl group of 3 to 6 carbon atoms unsubstituted or substituted with an alkyl group of 1 to 3 carbon atoms,
  an alkyl group of 1 to 3 carbon atoms substituted with a cycloalkyl group of 3 to 6 carbon atoms,
  a straight or branched hydroxyalkyl group of 1 to 6 carbon atoms,
  a straight or branched dihydroxyalkyl group of 3 to 6 carbon atoms,
  a straight or branched alkoxy group of 1 to 4 carbon atoms,
  a hydroxyalkoxy group of 2 to 4 carbon atoms,
  a straight or branched alkoxyalkyl group of 2 to 6 carbon atoms,
  a dialkoxyalkyl group of 3 to 6 carbon atoms,
  a dialkylamino group of 2 to 4 carbon atoms,
  an acetylamino group,
  a vinyl group, and
  a saturated or unsaturated five or six membered heterocyclic ring having 1 to 3 hetero-atoms selected from the group consisting of nitrogen, oxygen and sulfur, said heterocyclic ring being unsubstituted or substituted with same or different substituents selected from the group consisting of an alkyl group of 1 to 3 carbon atoms, an alkoxy group of 1 to 3 carbon atoms, a hydroxyalkyl group of 1 to 3 carbon atoms, a phenyl group, a carbamoyl group and a hydroxy group;

$R_2$ is selected form the group consisting of:
  a hydrogen atom,
  a phenyl group,
  a straight or branched alkyl group of 1 to 4 carbon atoms,
  a straight or branched hydroxyalkyl group of 2 to 4 carbon atoms, and
  an alkoxyalkyl group of 2 to 4 carbon atoms;

$R_3$ is selected form the group consisting of:
  a 2-hydroxyethyl group, and
  a 3-amino-2-pyridyl group having the formula

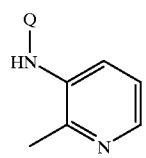

in which Q is a hydrogen atom or a straight or branched alkyl group of 1 to 4 carbon atoms; and
  n is 0 to 4.

2. The 2,5-pyridinedicarboxylic acid derivative, and pharmaceutically acceptable salts thereof, according to claim 1, wherein $R_3$ is a 3-amino-2-pyridyl group.

3. The 2,5-pyridinedicarboxylic acid derivative, and pharmaceutically acceptable salts thereof, according to claim 2, wherein
$R_1$ is selected from the group consisting of:
  a hydroxy group,
  a branched hydroxyalkyl group of 3 to 5 carbon atoms, and
  a branched dihydroxyalkyl group of 3 to 5 carbon atoms;
$R_2$ is selected from the group consisting of:
  a hydrogen atom,
  a methyl group,
  an ethyl group,
  a 2-hydroxyethyl group, and
  a phenyl group; and
n is 0, 2 or 3.

4. The 2,5-pyridinedicarboxylic acid derivative, and pharmaceutically acceptable salts thereof, according to claim 2, wherein
$R_1$ is selected from the group consisting of
  a straight or branched alkyl group of 2 to 4 carbon atoms,
  a cyclopropyl group,
  a cyclopentyl group,
  a methoxy group,
  an ethoxy group,
  a 2-hydroxyethoxy group,
  a branched alkoxyalkyl group of 4 to 5 carbon atoms,
  a dialkoxyalkyl group of 3 to 5 carbon atoms, and
  a dialkylamino group of 2 to 4 carbon atoms;
$R_2$ is selected from the group consisting of:
  a hydrogen atom,
  a methyl group,
  an ethyl group,
  an isopropyl group, and
  a 2-methoxyethyl group; and
n is 1 to 3.

5. The 2,5-pyridinedicarboxylic acid derivative, and pharmaceutically acceptable salts thereof, according to claim 1, wherein
$R_3$ is a 2-hydroxyethyl group.

6. The 2,5-pyridinedicarboxylic acid derivative, and pharmaceutically acceptable salts thereof, according to claim 5, wherein
$R_2$ is a hydrogen atom;
$R_1$ is selected from the group consisting of:
  a straight or branched alkyl group of 2 to 4 carbon atoms, and
  a straight or branched alkoxyalkyl group of 2 to 5 carbon atoms; and n is 0.

7. A method for treating a disease caused by a virus, wherein the virus is hepatitis B virus or human immunodeficiency virus comprising administering a patient in need thereof an effective amount of compound, and pharmaceutical pharmaceutically acceptable salts thereof, having the formula 1

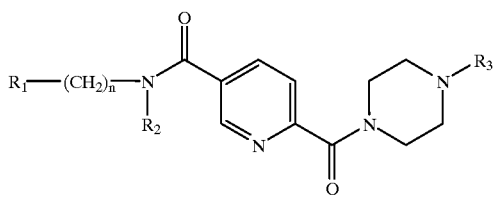
(1)

wherein $R_1$ is selected from the group consisting of:
a hydroxy group,
a straight or branched alkyl group of 1 to 6 carbon atoms,
a cycloalkyl group of 3 to 6 carbon atoms unsubstituted or substituted with an alkyl group of 1 to 3 carbon atoms,
an alkyl group of 1 to 3 carbon atoms substituted with a cycloalkyl group of 3 to 6 carbon atoms,
a straight or branched hydroxyalkyl group of 1 to 6 carbon atoms,
a straight or branched dihydroxyalkyl group of 3 to 6 carbon atoms,
a straight or branched alkoxy group of 1 to 4 carbon atoms,
a hydroxyalkoxy group of 2 to 4 carbon atoms,
a straight or branched alkoxyalkyl group of 2 to 6 carbon atoms,
a dialkoxyalkyl group of 3 to 6 carbon atoms,
a dialkylamino group of 2 to 4 carbon atoms,
an acetylamino group,
a vinyl group, and
a saturated or unsaturated five or six membered heterocyclic ring having 1 to 3 hetero-atoms selected from the group consisting of nitrogen, oxygen and sulfur, said heterocyclic ring being unsubstituted or substituted with same or different substituents selected from the group consisting of an alkyl group of 1 to 3 carbon atoms, an alkoxy group of 1 to 3 carbon atoms, a hydroxyalkyl group of 1 to 3 carbon atoms, a phenyl group, a carbamoyl group and a hydroxy group;

$R_2$ is selected form the group consisting of:
a hydrogen atom,
a phenyl group,
a straight or branched alkyl group of 1 to 4 carbon atoms,
a straight or branched hydroxyalkyl group of 2 to 4 carbon atoms, and
an alkoxyalkyl group of 2 to 4 carbon atoms;

$R_3$ is selected form the group consisting of:
a 2-hydroxyethyl group, and
a 3-amino-2-pyridyl group having the formula

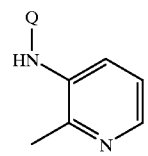

in which Q is a hydrogen atom or a straight or branched alkyl group of 1 to 4 carbon atoms; and
n is 0 to 4.

8. The 2,5-Pyridinedicarboxylic acid derivative according to claim 1, wherein the acid derivative is a stereospecific compound of either (R)- or (S)-type, when the $R_1$ is branched hydroxyalkyl group of 1 to 6 carbon atoms.

9. A process for preparing 2,5-pyridinedicarboxylic acid derivative of formula 1

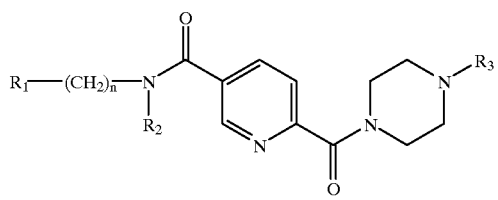
(1)

wherein $R_1$ is selected from the group consisting of:
a hydroxy group,
a straight or branched alkyl group of 1 to 6 carbon atoms,
a cycloalkyl group of 3 to 6 carbon atoms unsubstituted or substituted with an alkyl group of 1 to 3 carbon atoms,
an alkyl group of 1 to 3 carbon atoms substituted with a cycloalkyl group of 3 to 6 carbon atoms,
a straight or branched hydroxyalkyl group of 1 to 6 carbon atoms,
a straight or branched dihydroxyalkyl group of 3 to 6 carbon atoms,
a straight or branched alkoxy group of 1 to 4 carbon atoms,
a hydroxyalkoxy group of 2 to 4 carbon atoms,
a straight or branched alkoxyalkyl group of 2 to 6 carbon atoms,
a dialkoxyalkyl group of 3 to 6 carbon atoms,
a dialkylamino group of 2 to 4 carbon atoms,
an acetylamino group,
a vinyl group, and
a saturated or unsaturated five or six membered heterocyclic ring having 1 to 3 hetero-atoms selected from the group consisting of nitrogen, oxygen and sulfur, said heterocyclic ring being unsubstituted or substituted with same or different substituents selected from the group consisting of an alkyl group of 1 to 3 carbon atoms, an alkoxy group of 1 to 3 carbon atoms, a hydroxyalkyl group of 1 to 3 carbon atoms, a phenyl group, a carbamoyl group and a hydroxy group;

$R_2$ is selected form the group consisting of:
a hydrogen atom,
a phenyl group,
a straight or branched alkyl group of 1 to 4 carbon atoms, a straight or branched hydroxyalkyl group of 2 to 4 carbon atoms, and
an alkoxyalkyl group of 2 to 4 carbon atoms;
R_3 is selected form the group consisting of:
a 2-hydroxyethyl group, and
a 3-amino-2-pyridyl group having the formula

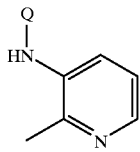

in which Q is a hydrogen atom or a straight or branched alkyl group of 1 to 4 carbon atoms; and
n is 0 to 4,
comprising the step of:
reacting nicotinic acid ester derivatives of formula 2

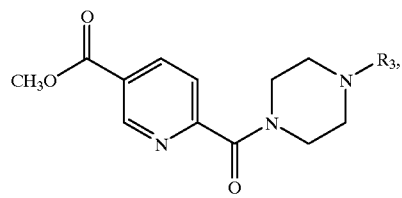

(2)

with an amine compound of formula 3

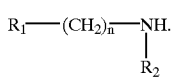

(3)

10. A process for preparing 2,5-pyridinedicarboxylic acid derivative of formula 1a (1a)

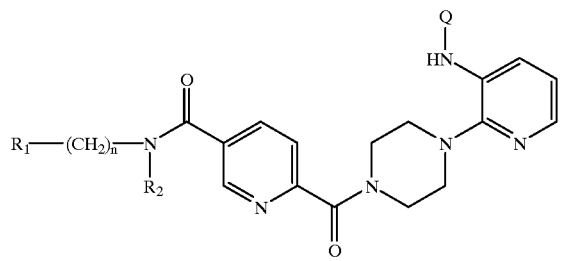

wherein
R_1 is selected from the group consisting of:
a hydroxy group,
a straight or branched alkyl group of 1 to 6 carbon atoms,
a cycloalkyl group of 3 to 6 carbon atoms unsubstituted or substituted with an alkyl group of 1 to 3 carbon atoms,
an alkyl group of 1 to 3 carbon atoms substituted with a cycloalkyl group of 3 to 6 carbon atoms,
a straight or branched hydroxyalkyl group of 1 to 6 carbon atoms,
a straight or branched dihydroxyalkyl group of 3 to 6 carbon atoms, a straight or branched alkoxy group of 1 to 4 carbon atoms,
a hydroxyalkoxy group of 2 to 4 carbon atoms,
a straight or branched alkoxyalkyl group of 2 to 6 carbon atoms,
a dialkoxyalkyl group of 3 to 6 carbon atoms,
a dialkylamino group of 2 to 4 carbon atoms,
an acetylamino group,
a vinyl group, and
a saturated or unsaturated five or six membered heterocyclic ring having 1 to 3 hetero-atoms selected from the group consisting of nitrogen, oxygen and sulfur, said heterocyclic ring being unsubstituted or substituted with same or different substituents selected from the group consisting of an alkyl group of 1 to 3 carbon atoms, an alkoxy group of 1 to 3 carbon atoms, a hydroxyalkyl group of 1 to 3 carbon atoms, a phenyl group, a carbamoyl group and a hydroxy group;
R_2 is selected form the group consisting of:
a hydrogen atom,
a phenyl group,
a straight or branched alkyl group of 1 to 4 carbon atoms,
a straight or branched hydroxyalkyl group of 2 to 4 carbon atoms, and
an alkoxyalkyl group of 2 to 4 carbon atoms;
Q is selected from the group consisting of:
a hydrogen atom and a straight or branched alkyl group of 1 to 4 carbon atoms; and
n is 0 to 4, comprising the step of:

reacting a compound of formula 2a

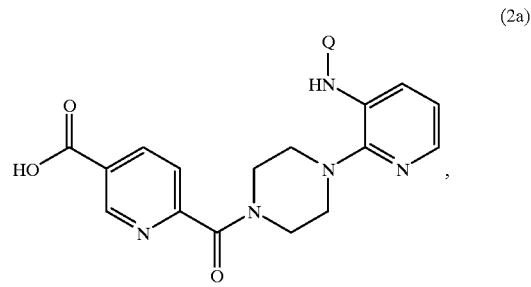

(2a)

with an amine compound of formula 3

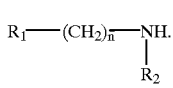

(3)

11. A process for preparing 2,5-pyridinedicarboxylic acid derivative of formula 1a

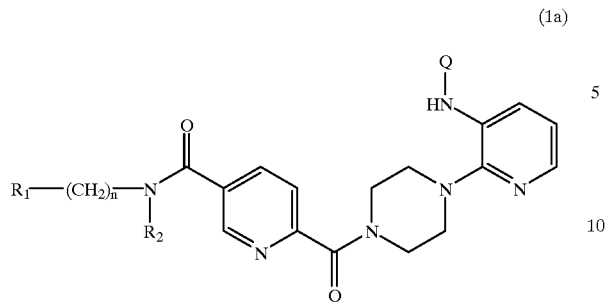

(1a)

wherein $R_1$ is selected from the group consisting of:
- a hydroxy group,
- a straight or branched alkyl group of 1 to 6 carbon atoms,
- a cycloalkyl group of 3 to 6 carbon atoms unsubstituted with an alkyl group of 1 to 3 carbon atoms,
- an alkyl group of 1 to 3 carbon atoms substituted with a cycloalkyl group of 3 to 6 carbon atoms,
- a straight or branched hydroxyalkyl group of 1 to 6 carbon atoms,
- a straight or branched dihydroxyalkyl group of 3 to 6 carbon atoms,
- a straight or branched alkoxy group of 1 to 4 carbon atoms,
- a hydroxyalkoxy group of 2 to 4 carbon atoms,
- a straight or branched alkoxyalkyl group of 2 to 6 carbon atoms,
- a dialkoxyalkyl group of 3 to 6 carbon atoms,
- a dialkylamino group of 2 to 4 carbon atoms,
- an acetylamino group,
- a vinyl group, and
- a saturated or unsaturated five or six membered heterocyclic ring having 1 to 3 hetero-atoms selected from the group consisting of nitrogen, oxygen and sulfur, said heterocyclic ring being unsubstituted or substituted with same or different substituents selected from the group consisting of an alkyl group of 1 to 3 carbon atoms, an alkoxy group of 1 to 3 carbon atoms, a hydroxyalkyl group of 1 to 3 carbon atoms, a phenyl group, a carbamoyl group and a hydroxy group;

$R_2$ is selected form the group consisting of:
- a hydrogen atom,
- a phenyl group,
- a straight or branched alkyl group of 1 to 4 carbon atoms,
- a straight or branched hydroxyalkyl group of 2 to 4 carbon atoms, and
- an alkoxyalkyl group of 2 to 4 carbon atoms;

Q is selected from the group consisting of:
- a hydrogen atom and a straight or branched alkyl group of 1 to 4 carbon atoms; and n is 0 to 4, comprising the step of:

(a) reacting nicotinic acid ester derivative including nitropyridyl group of formula 4

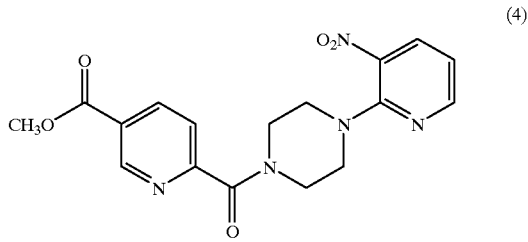

(4)

with an amine compound of formula 3

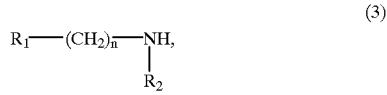

(3)

to form an intermediate of formula 6

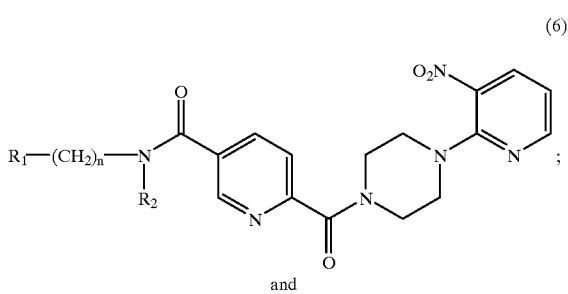

(6)

and (b) reducing the intermediate or reductively alkylating after reducing the intermediate to form the compound of formula 1a.

12. A process for preparing 2,5-pyridinedicarboxylic acid derivative of formula 1a

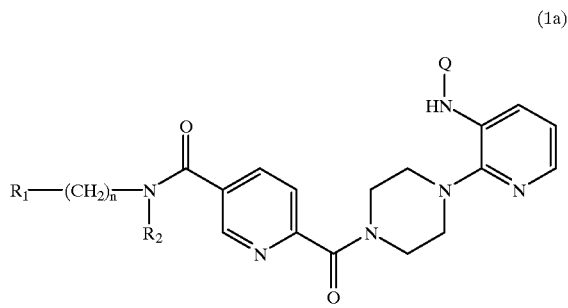

(1a)

wherein $R_1$ is selected from the group consisting of:
- a hydroxy group,
- a straight or branched alkyl group of 1 to 6 carbon atoms,
- a cycloalkyl group of 3 to 6 carbon atoms unsubstituted or substituted with an alkyl group of 1 to 3 carbon atoms,
- an alkyl group of 1 to 3 carbon atoms substituted with a cycloalkyl group of 3 to 6 carbon atoms,
- a straight or branched hydroxyalkyl group of 1 to 6 carbon atoms,
- a straight or branched dihydroxyalkyl group of 3 to 6 carbon atoms,
- a straight or branched alkoxy group of 1 to 4 carbon atoms, a hydroxyalkoxy group of 2 to 4 carbon atoms,
a straight or branched alkoxyalkyl group of 2 to 6 carbon atoms,
a dialkoxyalkyl group of 3 to 6 carbon atoms,
a dialkylamino group of 2 to 4 carbon atoms,
an acetylamino group,
a vinyl group, and
a saturated or unsaturated five or six membered heterocyclic ring having 1 to 3 hetero-atoms selected from the group consisting of nitrogen, oxygen and sulfur, said heterocyclic ring being unsubstituted or substituted with same or different substituents selected from the group consisting of an alkyl group of 1 to 3 carbon atoms, an alkoxy group of 1 to 3 carbon atoms, a hydroxyalkyl group of 1 to 3 carbon atoms, a phenyl group, a carbamoyl group and a hydroxy group;

$R_2$ is selected form the group consisting of:
a hydrogen atom,
a phenyl group,
a straight or branched alkyl group of 1 to 4 carbon atoms,
a straight or branched hydroxyalkyl group of 2 to 4 carbon atoms, and
an alkoxyalkyl group of 2 to 4 carbon atoms;

Q is selected from the group consisting of:
a hydrogen atom and a straight or branched alkyl group of 1 to 4 carbon atoms; and
n is 0 to 4, comprising the steps of:
(a) reacting nicotinic acid ester derivative including nitropyridyl group of formula 5

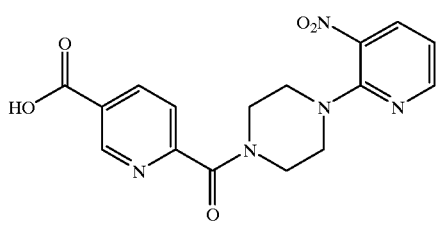

(5)

with a amine compound of formula 3

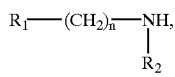

(3)

to form a intermediate of formula 6

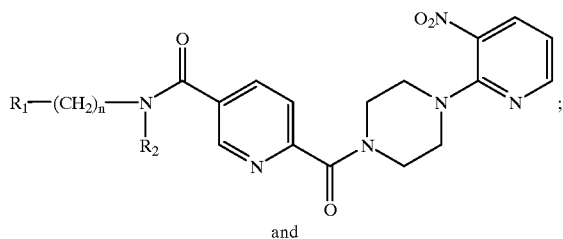

(6)

and (b) reducing the intermediate or reductively alkylating after reducing the intermediate to form the compound of formula 1a.

13. A process for preparing nicotinic acid derivative of formula 2a

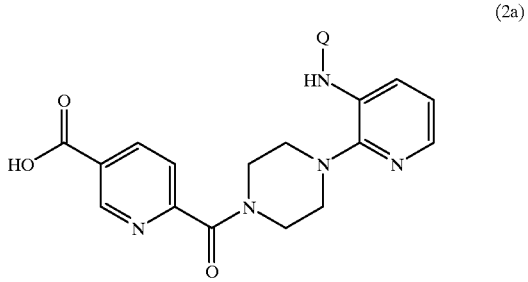

(2a)

wherein Q is selected from the group consisting of:

a hydrogen atom and a straight or branched alkyl group of 1 to 4 carbon atoms, comprising the steps of:

(a) reacting 5-(methoxycarbonyl)-2-pyridinecarboxylic acid of formula 7

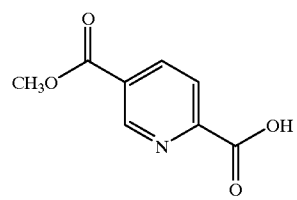

(7)

with an acid chloride derivative to form an acid anhydride derivative;

(b) reacting the acid anhydride derivative with 1-(3-nitro-2-pyridyl)piperazine of formula 8

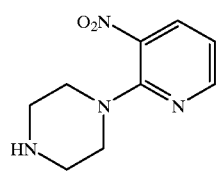

(8)

to form a nicotinic acid ester derivative of formula 4

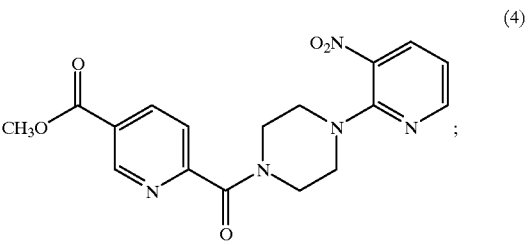

(4)

(c) reducing the nicotinic acid ester derivative to obtain an aminopyridyl group derivative of formula 9

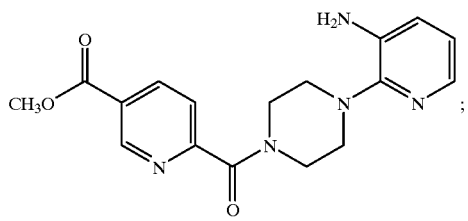

(9)

(d) reductively alkylating the aminopyridyl group derivative in the presence of a reducing agent under an acidic condition to obtain a nicotinic acid ester derivative of formula 2b

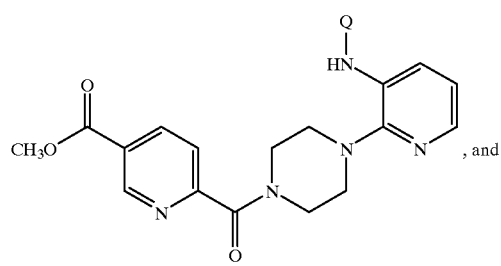

(2b)

, and (e) hydrolyzing the nicotinic acid ester derivative of formula 2b to give nicotinic acid derivative of the formula 2a.

14. A process for preparing ester derivative of the following formula 2b

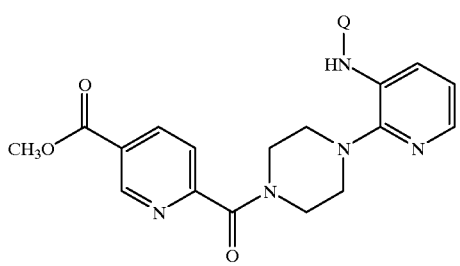

(2b)

wherein Q is selected from the group consisting of:
a hydrogen atom and a straight or branched alkyl group of 1 to 4 carbon atoms, comprising the step of:
reacting 5-(methoxycarbonyl)-2-pyridinecarboxylic acid of formula 7

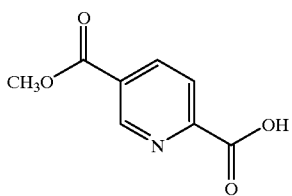

(7)

with 1-[3-(alkylamino)-2-pyridyl]piperazine of formula 10

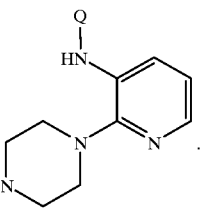

(10)

15. Nicotinic acid ester derivative of a formula 2

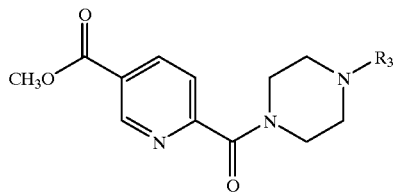

(2)

wherein $R_3$ is selected form the group consisting of:
a 2-hydroxyethyl group, and
a 3-amino-2-pyridyl group having the formula

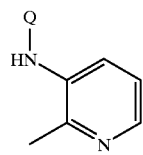

in which Q is a hydrogen atom or a straight or branched alkyl group of 1 to 4 carbon atoms.

* * * * *